US008766217B2

(12) United States Patent
Balakin

(10) Patent No.: US 8,766,217 B2
(45) Date of Patent: *Jul. 1, 2014

(54) MULTI-FIELD CHARGED PARTICLE CANCER THERAPY METHOD AND APPARATUS

(76) Inventor: Vladimir Yegorovich Balakin, Moscow (RU)

(*) Notice: Subject to any disclaimer, the term of this patent is extended or adjusted under 35 U.S.C. 154(b) by 42 days.

This patent is subject to a terminal disclaimer.

(21) Appl. No.: 12/994,130

(22) PCT Filed: May 21, 2009

(86) PCT No.: PCT/RU2009/000248
§ 371 (c)(1),
(2), (4) Date: Jun. 15, 2011

(87) PCT Pub. No.: WO2009/142546
PCT Pub. Date: Nov. 26, 2009

(65) Prior Publication Data
US 2011/0233423 A1    Sep. 29, 2011

Related U.S. Application Data

(60) Provisional application No. 61/055,395, filed on May 22, 2008, provisional application No. 61/055,409, (Continued)

(30) Foreign Application Priority Data

Mar. 4, 2009 (WO) ............... PCT/RU2009/000105

(51) Int. Cl.
*A61N 5/10* (2006.01)
(52) U.S. Cl.
USPC .................................. 250/492.3; 250/503.1
(58) Field of Classification Search
USPC ............................. 250/492.1, 503.1, 492.3
See application file for complete search history.

(56) References Cited

U.S. PATENT DOCUMENTS 2,306,875 A    12/1942    Fremlin
2,533,688 A    12/1950    Quam
(Continued)

FOREIGN PATENT DOCUMENTS

CN    1178667    4/1998
CN    1242594    1/2000
(Continued)

OTHER PUBLICATIONS

Adams, et al., "Electrostatic cylinder lenses II: Three element einzel lenses", Journal of Physics E: Sci. Intr., vol. 5, No. 2, Feb. 1972, pp. 150-155.

(Continued)

*Primary Examiner* — Jack Berman
*Assistant Examiner* — Wyatt Stoffa
(74) *Attorney, Agent, or Firm* — Michael A. Glenn; Perkins Coie LLP

(57) ABSTRACT

The invention comprises a multi-field charged particle irradiation method and apparatus. Radiation is delivered through an entry point into the tumor and Bragg peak energy is targeted to a distal or far side of the tumor from an ingress point. Delivering Bragg peak energy to the distal side of the tumor from the ingress point is repeated from multiple rotational directions. Preferably, beam intensity is proportional to radiation dose delivery efficiency. Preferably, the charged particle therapy is timed to patient respiration via control of charged particle beam injection, acceleration, extraction, and/or targeting methods and apparatus. Optionally, multi-axis control of the charged particle beam is used simultaneously with the multi-field irradiation. Combined, the system allows multi-field and multi-axis charged particle irradiation of tumors yielding precise and accurate irradiation dosages to a tumor with distribution of harmful irradiation energy about the tumor.

19 Claims, 27 Drawing Sheets

Related U.S. Application Data filed on May 22, 2008, provisional application No. 61/134,717, filed on Jul. 14, 2008, provisional application No. 61/134,707, filed on Jul. 14, 2008, provisional application No. 61/134,718, filed on Jul. 14, 2008, provisional application No. 61/137,574, filed on Aug. 1, 2008, provisional application No. 61/188,406, filed on Aug. 11, 2008, provisional application No. 61/188,407, filed on Aug. 11, 2008, provisional application No. 61/189,017, filed on Aug. 15, 2008, provisional application No. 61/189,815, filed on Aug. 25, 2008, provisional application No. 61/190,546, filed on Sep. 2, 2008, provisional application No. 61/190,613, filed on Sep. 2, 2008, provisional application No. 61/191,043, filed on Sep. 8, 2008, provisional application No. 61/192,245, filed on Sep. 17, 2008, provisional application No. 61/192,237, filed on Sep. 17, 2008, provisional application No. 61/197,971, filed on Nov. 3, 2008, provisional application No. 61/198,248, filed on Nov. 5, 2008, provisional application No. 61/198,508, filed on Nov. 7, 2008, provisional application No. 61/198,509, filed on Nov. 7, 2008, provisional application No. 61/199,405, filed on Nov. 17, 2008, provisional application No. 61/199,403, filed on Nov. 17, 2008, provisional application No. 61/199,404, filed on Nov. 17, 2008, provisional application No. 61/201,728, filed on Dec. 15, 2008, provisional application No. 61/201,732, filed on Dec. 15, 2008, provisional application No. 61/201,731, filed on Dec. 15, 2008, provisional application No. 61/203,308, filed on Dec. 22, 2008, provisional application No. 61/205,362, filed on Jan. 21, 2009, provisional application No. 61/208,182, filed on Feb. 23, 2009, provisional application No. 61/208,971, filed on Mar. 3, 2009, provisional application No. 61/209,529, filed on Mar. 9, 2009.

(56) References Cited

U.S. PATENT DOCUMENTS

| | | | |
|---|---|---|---|
| 2,790,902 A | 4/1957 | Wright | |
| 2,822,490 A | 2/1958 | Scag | |
| 3,128,405 A | 4/1964 | Lambertson | |
| 3,328,708 A | 6/1967 | Smith et al. | |
| 3,412,337 A | 11/1968 | Lothrop | |
| 3,461,410 A * | 8/1969 | Beth | 335/210 |
| 3,655,968 A | 4/1972 | Moore et al. | |
| 3,806,749 A | 4/1974 | Yntema | |
| 3,867,705 A | 2/1975 | Hudson | |
| 3,882,339 A | 5/1975 | Rate et al. | |
| 3,906,280 A | 9/1975 | Andelfinger | |
| 4,344,011 A * | 8/1982 | Hayashi et al. | 378/138 |
| 4,442,355 A * | 4/1984 | Tamura et al. | 250/310 |
| 4,607,380 A | 8/1986 | Oliver | |
| 4,612,660 A | 9/1986 | Huang et al. | |
| 4,622,687 A | 11/1986 | Whitaker et al. | |
| 4,705,955 A | 11/1987 | Mileikowsky | |
| 4,726,046 A * | 2/1988 | Nunan | 378/65 |
| 4,730,353 A | 3/1988 | Ono | |
| 4,868,844 A | 9/1989 | Nunan | |
| 4,870,287 A * | 9/1989 | Cole et al. | 250/492.3 |
| 4,992,746 A | 2/1991 | Martin | |
| H000909 H * | 4/1991 | Danby et al. | 315/501 |
| H0000909 H * | 4/1991 | Danby et al. | 315/501 |
| 5,017,789 A | 5/1991 | Young | |
| 5,039,867 A | 8/1991 | Nishihara | |
| 5,073,913 A * | 12/1991 | Martin | 378/34 |
| 5,117,829 A | 6/1992 | Miller et al. | |
| 5,168,241 A | 12/1992 | Hirota | |
| 5,177,448 A | 1/1993 | Ikeguchi | |
| 5,260,581 A | 11/1993 | Lesyna | |
| 5,285,166 A | 2/1994 | Hiramoto | |
| 5,349,198 A | 9/1994 | Takanaka | |
| 5,363,008 A | 11/1994 | Hiramoto | |
| 5,388,580 A | 2/1995 | Sullivan | |
| 5,402,462 A * | 3/1995 | Nobuta | 378/20 |
| 5,423,328 A | 6/1995 | Gavish | |
| 5,440,133 A | 8/1995 | Moyers | |
| 5,483,129 A | 1/1996 | Yamamoto | |
| 5,511,549 A | 4/1996 | Legg | |
| 5,538,494 A | 7/1996 | Matsuda | |
| 5,568,109 A | 10/1996 | Takayama | |
| 5,576,549 A | 11/1996 | Hell et al. | |
| 5,585,642 A | 12/1996 | Britton | |
| 5,600,213 A | 2/1997 | Hiramoto | |
| 5,626,682 A | 5/1997 | Kobari | |
| 5,633,907 A | 5/1997 | Gravelle | |
| 5,659,223 A * | 8/1997 | Goodman | 315/39 |
| 5,661,366 A | 8/1997 | Hirota | |
| 5,668,371 A | 9/1997 | Deasy et al. | |
| 5,698,954 A | 12/1997 | Hirota | |
| 5,760,395 A | 6/1998 | Johnstone | |
| 5,789,875 A | 8/1998 | Hiramoto | |
| 5,818,058 A | 10/1998 | Nakanishi | |
| 5,820,320 A | 10/1998 | Kobari | |
| 5,825,845 A | 10/1998 | Blair | |
| 5,854,531 A | 12/1998 | Young et al. | |
| 5,866,912 A | 2/1999 | Slater | |
| 5,895,926 A | 4/1999 | Britton | |
| 5,907,595 A | 5/1999 | Sommerer | |
| 5,917,293 A | 6/1999 | Saito | |
| 5,949,080 A | 9/1999 | Ueda et al. | |
| 5,969,367 A | 10/1999 | Hiramoto | |
| 5,986,274 A | 11/1999 | Akiyama | |
| 5,993,373 A | 11/1999 | Nonaka | |
| 6,008,499 A | 12/1999 | Hiramoto | |
| 6,034,377 A | 3/2000 | Pu | |
| 6,057,655 A | 5/2000 | Jongen | |
| 6,087,670 A | 7/2000 | Hiramoto | |
| 6,087,672 A | 7/2000 | Matsuda | |
| 6,148,058 A * | 11/2000 | Dobbs | 378/19 |
| 6,207,952 B1 | 3/2001 | Kan | |
| 6,218,675 B1 | 4/2001 | Akiyama | |
| 6,236,043 B1 | 5/2001 | Tadokoro | |
| 6,265,837 B1 | 7/2001 | Akiyama | |
| 6,282,263 B1 | 8/2001 | Arndt | |
| 6,292,538 B1 | 9/2001 | Hell et al. | |
| 6,316,776 B1 | 11/2001 | Hiramoto | |
| 6,322,249 B1 | 11/2001 | Wofford | |
| 6,333,966 B1 | 12/2001 | Schoen | |
| 6,335,535 B1 | 1/2002 | Miyake et al. | |
| 6,339,635 B1 | 1/2002 | Schardt | |
| 6,356,617 B1 | 3/2002 | Besch | |
| 6,365,894 B2 | 4/2002 | Tadokoro | |
| 6,403,967 B1 | 6/2002 | Chen et al. | |
| 6,421,416 B1 | 7/2002 | Sliski | |
| 6,433,336 B1 | 8/2002 | Jongen | |
| 6,433,349 B2 | 8/2002 | Akiyama | |
| 6,433,494 B1 | 8/2002 | Kulish | |
| 6,437,513 B1 | 8/2002 | Stelzer | |
| 6,444,990 B1 | 9/2002 | Morgan | |
| 6,462,348 B1 | 10/2002 | Gelbart | |
| 6,462,490 B1 | 10/2002 | Matsuda | |
| 6,470,068 B2 | 10/2002 | Cheng | |
| 6,472,834 B2 | 10/2002 | Hiramoto | |
| 6,476,403 B1 | 11/2002 | Dolinskii | |
| 6,545,436 B1 | 4/2003 | Gary | |
| 6,560,354 B1 | 5/2003 | Maurer, Jr. | |
| 6,580,084 B1 | 6/2003 | Hiramoto | |
| 6,597,005 B1 | 7/2003 | Badura | |
| 6,600,164 B1 | 7/2003 | Badura | |
| 6,614,038 B1 | 9/2003 | Brand | |
| 6,617,598 B1 | 9/2003 | Matsuda | |
| 6,626,842 B2 | 9/2003 | Oka | |
| 6,635,882 B1 | 10/2003 | Pavlovic et al. | |
| 6,639,234 B1 | 10/2003 | Badura | |
| 6,661,876 B2 | 12/2003 | Turner et al. | |
| 6,670,618 B1 | 12/2003 | Hartmann | |
| 6,683,318 B1 | 1/2004 | Haberer | |
| 6,683,426 B1 | 1/2004 | Kleeven | |

(56) References Cited

U.S. PATENT DOCUMENTS

| | | | |
|---|---|---|---|
| 6,710,362 B2 | 3/2004 | Kraft | |
| 6,717,162 B1 | 4/2004 | Jongen | |
| 6,730,921 B2 | 5/2004 | Kraft | |
| 6,736,831 B1 | 5/2004 | Hartmann | |
| 6,745,072 B1 | 6/2004 | Badura | |
| 6,774,383 B2 | 8/2004 | Norimine | |
| 6,777,700 B2 | 8/2004 | Yanagisawa | |
| 6,785,359 B2 | 8/2004 | Lemaitre | |
| 6,787,771 B2 | 9/2004 | Bashkirov | |
| 6,792,078 B2 | 9/2004 | Kato | |
| 6,799,068 B1 | 9/2004 | Hartmann | |
| 6,800,866 B2 | 10/2004 | Amemiya | |
| 6,803,591 B2 | 10/2004 | Muramatsu | |
| 6,809,325 B2 | 10/2004 | Dahl | |
| 6,819,743 B2 | 11/2004 | Kato | |
| 6,822,244 B2 | 11/2004 | Beloussov | |
| 6,823,045 B2 | 11/2004 | Kato | |
| 6,838,676 B1 | 1/2005 | Jackson | |
| 6,859,741 B2 | 2/2005 | Haberer | |
| 6,873,123 B2 | 3/2005 | Marchand | |
| 6,881,970 B2 | 4/2005 | Akiyama | |
| 6,891,177 B1 | 5/2005 | Kraft | |
| 6,897,451 B2 | 5/2005 | Kaercher | |
| 6,900,446 B2 | 5/2005 | Akiyama | |
| 6,903,351 B1 | 6/2005 | Akiyama | |
| 6,903,356 B2 | 6/2005 | Muramatsu | |
| 6,931,100 B2 | 8/2005 | Kato | |
| 6,936,832 B2 | 8/2005 | Norimine | |
| 6,937,696 B1 | 8/2005 | Mostafavi | |
| 6,953,943 B2 | 10/2005 | Yanagisawa | |
| 6,979,832 B2 | 12/2005 | Yanagisawa | |
| 6,984,835 B2 | 1/2006 | Harada | |
| 6,992,312 B2 | 1/2006 | Yanagisawa | |
| 7,006,594 B2 | 2/2006 | Chell et al. | |
| 7,012,267 B2 | 3/2006 | Moriyama | |
| 7,026,636 B2 | 4/2006 | Yanagisawa | |
| 7,030,396 B2 | 4/2006 | Muramatsu | |
| 7,045,781 B2 | 5/2006 | Adamec | |
| 7,049,613 B2 | 5/2006 | Yanagisawa | |
| 7,053,389 B2 | 5/2006 | Yanagisawa | |
| 7,054,801 B2 | 5/2006 | Sakamoto | |
| 7,058,158 B2 | 6/2006 | Sako | |
| 7,060,997 B2 | 6/2006 | Norimine | |
| 7,071,479 B2 | 7/2006 | Yanagisawa | |
| 7,081,619 B2 | 7/2006 | Bashkirov | |
| 7,084,410 B2 | 8/2006 | Beloussov | |
| 7,091,478 B2 | 8/2006 | Haberer | |
| 7,102,144 B2 | 9/2006 | Matsuda | |
| 7,109,505 B1 | 9/2006 | Sliski | |
| 7,122,811 B2 | 10/2006 | Matsuda | |
| 7,141,810 B2 | 11/2006 | Kakiuchi | |
| 7,154,107 B2 | 12/2006 | Yanagisawa | |
| 7,154,108 B2 | 12/2006 | Tadokoro | |
| 7,173,264 B2 | 2/2007 | Moriyama | |
| 7,173,265 B2 | 2/2007 | Miller | |
| 7,193,227 B2 | 3/2007 | Hiramoto | |
| 7,199,382 B2 | 4/2007 | Rigney | |
| 7,208,748 B2 | 4/2007 | Sliski | |
| 7,212,608 B2 | 5/2007 | Nagamine | |
| 7,212,609 B2 | 5/2007 | Nagamine | |
| 7,223,463 B2 | 5/2007 | Arakida | |
| 7,227,161 B2 | 6/2007 | Matsuda | |
| 7,247,869 B2 | 7/2007 | Tadokoro | |
| 7,252,745 B2 | 8/2007 | Gorokhovsky | |
| 7,259,529 B2 | 8/2007 | Tanaka | |
| 7,262,424 B2 | 8/2007 | Moriyama | |
| 7,274,018 B2 | 9/2007 | Adamec | |
| 7,274,025 B2 | 9/2007 | Berdermann | |
| 7,280,633 B2 | 10/2007 | Cheng | |
| 7,297,967 B2 | 11/2007 | Yanagisawa | |
| 7,301,162 B2 | 11/2007 | Matsuda | |
| 7,307,264 B2 | 12/2007 | Brusasco | |
| 7,310,404 B2 | 12/2007 | Tashiro | |
| 7,315,606 B2 | 1/2008 | Tsujii | |
| 7,319,231 B2 | 1/2008 | Moriyama | |
| 7,345,291 B2 | 3/2008 | Kats | |
| 7,345,292 B2 | 3/2008 | Moriyama | |
| 7,349,522 B2 | 3/2008 | Yan et al. | |
| 7,351,988 B2 | 4/2008 | Naumann | |
| 7,355,189 B2 | 4/2008 | Yanagisawa | |
| 7,356,112 B2 | 4/2008 | Brown | |
| 7,368,740 B2 | 5/2008 | Beloussov | |
| 7,372,053 B2 | 5/2008 | Yamashita | |
| 7,381,979 B2 | 6/2008 | Yamashita | |
| 7,385,203 B2 | 6/2008 | Nakayama | |
| 7,394,082 B2 | 7/2008 | Fujimaki | |
| 7,397,054 B2 | 7/2008 | Natori | |
| 7,397,901 B1 | 7/2008 | Johnsen | |
| 7,402,822 B2 | 7/2008 | Guertin | |
| 7,402,823 B2 | 7/2008 | Guertin | |
| 7,402,824 B2 | 7/2008 | Guertin | |
| 7,402,963 B2 | 7/2008 | Sliski | |
| 7,425,717 B2 | 9/2008 | Matsuda | |
| 7,432,516 B2 | 10/2008 | Peggs | |
| 7,439,528 B2 | 10/2008 | Nishiuchi | |
| 7,446,490 B2 | 11/2008 | Jongen | |
| 7,449,701 B2 | 11/2008 | Fujimaki | |
| 7,456,415 B2 | 11/2008 | Yanagisawa | |
| 7,456,591 B2 | 11/2008 | Jongen | |
| 7,465,944 B2 | 12/2008 | Ueno et al. | |
| 7,476,883 B2 * | 1/2009 | Nutt | 250/493.1 |
| 7,531,818 B2 | 5/2009 | Brahme | |
| 7,555,103 B2 | 6/2009 | Johnsen | |
| 7,560,717 B2 | 7/2009 | Matsuda | |
| 7,576,342 B2 | 8/2009 | Hiramoto | |
| 7,586,112 B2 | 9/2009 | Chiba | |
| 7,589,334 B2 | 9/2009 | Hiramoto | |
| 7,626,347 B2 | 12/2009 | Sliski | |
| 7,634,057 B2 | 12/2009 | Ein-Gal | |
| 7,659,521 B2 | 2/2010 | Pedroni | |
| 7,668,585 B2 | 2/2010 | Green | |
| 7,692,168 B2 | 4/2010 | Moriyama | |
| 7,701,677 B2 | 4/2010 | Schultz | |
| 7,709,818 B2 | 5/2010 | Matsuda | |
| 7,718,982 B2 | 5/2010 | Sliski | |
| 7,728,311 B2 | 6/2010 | Gall | |
| 7,729,469 B2 | 6/2010 | Kobayashi | |
| 7,741,623 B2 | 6/2010 | Sommer | |
| 7,755,305 B2 | 7/2010 | Umezawa | |
| 7,772,577 B2 | 8/2010 | Saito et al. | |
| 7,796,730 B2 | 9/2010 | Marash | |
| 7,801,277 B2 | 9/2010 | Zou | |
| 7,807,982 B2 | 10/2010 | Nishiuchi | |
| 7,817,778 B2 | 10/2010 | Nord | |
| 7,825,388 B2 | 11/2010 | Nihongi | |
| 7,826,593 B2 | 11/2010 | Svensson | |
| 7,834,336 B2 | 11/2010 | Boeh | |
| 7,838,855 B2 | 11/2010 | Fujii | |
| 7,848,488 B2 | 12/2010 | Mansfield | |
| 7,860,216 B2 | 12/2010 | Jongen | |
| 7,875,868 B2 | 1/2011 | Moriyama | |
| 7,894,574 B1 | 2/2011 | Nord | |
| 7,906,769 B2 | 3/2011 | Blasche | |
| 7,919,765 B2 | 4/2011 | Timmer | |
| 7,940,891 B2 | 5/2011 | Star-Lack | |
| 7,953,205 B2 | 5/2011 | Balakin | |
| 7,961,844 B2 | 6/2011 | Takeda | |
| 7,977,656 B2 | 7/2011 | Fujimaki | |
| 7,982,198 B2 | 7/2011 | Nishiuchi | |
| 7,987,053 B2 | 7/2011 | Schaffner | |
| 7,995,813 B2 | 8/2011 | Foshee | |
| 8,003,964 B2 | 8/2011 | Stark | |
| 8,009,804 B2 | 8/2011 | Siljamaki | |
| 8,045,679 B2 | 10/2011 | Balakin | |
| 8,093,564 B2 * | 1/2012 | Balakin | 250/396 R |
| 8,129,694 B2 | 3/2012 | Balakin | |
| 8,129,699 B2 * | 3/2012 | Balakin | 250/492.3 |
| 8,129,701 B2 * | 3/2012 | Al-Sadah et al. | 250/505.1 |
| 8,144,832 B2 | 3/2012 | Balakin | |
| 2001/0002208 A1 | 5/2001 | Matsushita et al. | |
| 2002/0183667 A1 | 12/2002 | Kitadou et al. | |
| 2003/0048080 A1 | 3/2003 | Amemiya et al. | |
| 2003/0104207 A1 | 6/2003 | Arakida | |
| 2003/0163015 A1 | 8/2003 | Yanagisawa | |

(56) References Cited

U.S. PATENT DOCUMENTS

| | | |
|---|---|---|
| 2003/0164459 A1* | 9/2003 | Schardt et al. ............ 250/492.3 |
| 2003/0188757 A1 | 10/2003 | Yanof et al. |
| 2004/0002641 A1 | 1/2004 | Sjogren et al. |
| 2004/0022361 A1 | 2/2004 | Lemaitre |
| 2004/0062354 A1 | 4/2004 | Kato et al. |
| 2004/0155206 A1 | 8/2004 | Marchand |
| 2004/0162457 A1 | 8/2004 | Maggiore et al. |
| 2004/0184583 A1 | 9/2004 | Nagamine et al. |
| 2004/0218725 A1 | 11/2004 | Radley et al. |
| 2005/0017193 A1* | 1/2005 | Jackson ................ 250/396 R |
| 2005/0134204 A1 | 6/2005 | Bechthold et al. |
| 2005/0161618 A1 | 7/2005 | Pedroni |
| 2005/0211905 A1 | 9/2005 | Stark |
| 2005/0226378 A1 | 10/2005 | Cocks et al. |
| 2005/0238134 A1 | 10/2005 | Brusasco |
| 2005/0258784 A1 | 11/2005 | Makita et al. |
| 2005/0269497 A1 | 12/2005 | Jongen |
| 2006/0050848 A1 | 3/2006 | Vilsmeier et al. |
| 2006/0076515 A1 | 4/2006 | Matsuda et al. |
| 2006/0106301 A1* | 5/2006 | Kats ....................... 600/415 |
| 2006/0163495 A1 | 7/2006 | Hiramoto et al. |
| 2006/0171508 A1 | 8/2006 | Noda et al. |
| 2006/0255285 A1 | 11/2006 | Jongen |
| 2007/0018121 A1 | 1/2007 | Leyman |
| 2007/0055124 A1 | 3/2007 | Viswanathan et al. |
| 2007/0093723 A1 | 4/2007 | Keall et al. |
| 2007/0121788 A1 | 5/2007 | Mildner et al. |
| 2007/0131876 A1* | 6/2007 | Brahme ................ 250/492.1 |
| 2007/0170994 A1* | 7/2007 | Peggs et al. ............... 331/34 |
| 2007/0181815 A1* | 8/2007 | Ebstein .................. 250/370.11 |
| 2007/0225603 A1* | 9/2007 | Jackson .................... 600/436 |
| 2008/0023644 A1 | 1/2008 | Pedroni |
| 2008/0043916 A1 | 2/2008 | Lemaitre |
| 2008/0049896 A1 | 2/2008 | Kuduvalli et al. |
| 2008/0067413 A1 | 3/2008 | Nutt |
| 2008/0093567 A1 | 4/2008 | Gall |
| 2008/0139955 A1 | 6/2008 | Hansmann et al. |
| 2008/0191142 A1* | 8/2008 | Pedroni ................ 250/396 ML |
| 2008/0258084 A1 | 10/2008 | Platzgummer et al. |
| 2009/0086905 A1 | 4/2009 | Boyden et al. |
| 2009/0096179 A1 | 4/2009 | Stark |
| 2009/0122961 A1 | 5/2009 | Ohsawa |
| 2009/0140672 A1 | 6/2009 | Gall |
| 2009/0168960 A1 | 7/2009 | Jongen |
| 2009/0189095 A1* | 7/2009 | Flynn et al. ............ 250/492.3 |
| 2009/0190719 A1 | 7/2009 | Barschdorf et al. |
| 2009/0200483 A1 | 8/2009 | Gall |
| 2009/0236545 A1 | 9/2009 | Timmer |
| 2009/0283704 A1 | 11/2009 | Nishiuchi |
| 2009/0289194 A1 | 11/2009 | Saito |
| 2009/0304153 A1 | 12/2009 | Amelia |
| 2009/0309046 A1* | 12/2009 | Balakin .................. 250/492.3 |
| 2010/0001212 A1 | 1/2010 | Nishiuchi |
| 2010/0008468 A1 | 1/2010 | Balakin |
| 2010/0008469 A1 | 1/2010 | Balakin |
| 2010/0020937 A1 | 1/2010 | Hautmann et al. |
| 2010/0027745 A1 | 2/2010 | Balakin |
| 2010/0033115 A1 | 2/2010 | Cleland |
| 2010/0045213 A1 | 2/2010 | Sliski |
| 2010/0059688 A1 | 3/2010 | Claereboudt |
| 2010/0060209 A1 | 3/2010 | Balakin |
| 2010/0128846 A1 | 5/2010 | Balakin |
| 2010/0176309 A1 | 7/2010 | Mackie et al. |
| 2010/0230617 A1 | 9/2010 | Gall |
| 2010/0272241 A1 | 10/2010 | Amelia |
| 2010/0308235 A1 | 12/2010 | Sliski |
| 2011/0073778 A1 | 3/2011 | Natori |
| 2011/0089329 A1 | 4/2011 | Jongen |
| 2011/0118530 A1 | 5/2011 | Balakin |
| 2011/0118531 A1 | 5/2011 | Balakin |
| 2011/0127443 A1 | 6/2011 | Comer |
| 2011/0137159 A1 | 6/2011 | Jongen |
| 2011/0150180 A1 | 6/2011 | Balakin |
| 2011/0168903 A1* | 7/2011 | Kyele et al. ............ 250/370.1 |
| 2011/0180720 A1 | 7/2011 | Balakin |
| 2011/0182410 A1 | 7/2011 | Balakin |
| 2011/0186720 A1 | 8/2011 | Jongen |
| 2012/0143051 A1 | 6/2012 | Balakin |

FOREIGN PATENT DOCUMENTS

| | | |
|---|---|---|
| EP | 1683545 A2 | 7/2006 |
| GB | 1270619 | 4/1972 |
| JP | 62-87171 | 4/1987 |
| JP | H01-162199 | 6/1989 |
| JP | 03-075071 | 3/1991 |
| JP | 05-137806 | 6/1993 |
| JP | H05-200126 | 8/1993 |
| JP | 07-303710 | 11/1995 |
| JP | 9129151 | 5/1997 |
| JP | 11-057042 | 3/1999 |
| JP | 2921433 | 7/1999 |
| JP | 2000-030641 | 1/2000 |
| JP | 2000021597 | 1/2000 |
| JP | 2002-33275 | 1/2002 |
| JP | 2002-540581 | 11/2002 |
| JP | 2002-360543 | 12/2002 |
| JP | 2003-534066 | 11/2003 |
| JP | 2004357724 | 12/2004 |
| RU | 2149045 | 5/2000 |
| RU | 2149662 | 5/2000 |
| RU | 2006103781 | 9/2007 |
| WO | WO-99/53998 | 10/1999 |
| WO | WO-00/58991 | 10/2000 |
| WO | WO-01/89625 | 11/2001 |
| WO | WO-2005018734 | 3/2005 |
| WO | WO-2006094533 | 9/2006 |
| WO | WO-2007014026 | 2/2007 |
| WO | WO-200802443 | 2/2008 |
| WO | WO-20080044194 | 4/2008 |

OTHER PUBLICATIONS

Amaldi, U. et al., "A Hospital-Based Hadrontherapy Complex", Proceedings of EPAC '94, London, England, Jun. 1994, pp. 49-51.

Arimoto, et al., "A Study of the PRISM-FFAG Magnet", Proc. of Cyclotron 2004 Conference, Tokyo, Japan, Oct. 2004, pp. 243-245.

Biophysics Group, et al., "Design, construction and First Experiments of a Magnetic Scanning System for Therapy. Radiobilogical Experiments on the Radiobiological Action of Carbon, Oxygen and Neon", GSI Report, Gesellschaft Fuer Schwerionenforschung MbH, vol. GSI-91-18, Jun. 1991, pp. 1-31.

Blackmore, et al., "Operation of the TRIUMF Proton Therapy Facility", Proc. of the 1997 Particle Accelerator Conference, vol. 3, Piscataway, NJ, USA May 1997, pp. 3831-3833.

Bryant, P., "Proton-Ion Medical Machine Study (PIMMS) Part II", Proton-Ion Medical Machine Study: PIMMS, European Organisation for Nuclear Research Cern—PS Division, Geneva, Switzerland, Jul. 2000, pp. 23, 228, 289-290.

Craddock, M.K., "New Concepts in FFAG Design for Secondary Beam Facilities and other Applications", Proc. of 2005 Particle Accelerator Conference, Knoxville, TN, USA, May 2005, pp. 261-265.

Dzhelepov, et al., "Use of USSR proton accelerators for medical purposes", IEEE Transactions on Nuclear Science USA, vol. ns-20, No. 3, Jun. 1973, pp. 268-270.

Endo, et al., "Medical Synchrotron for Proton Therapy", Proc. of EPAC 88, Rome, Italy, Jun. 1988, pp. 1459-1461.

Franzke, et al., "Commissioning of the heavy ion storage ring ESR", Proc. of EPAC 90, Nice, France, Jun. 1990, pp. 46-48.

Johnstone, et al., "Tune-Stabilized Linear-Field FFAG for Carbon Therapy", Proc. of EPAC 2006, Edinburgh, Scotland, UK, Jun. 2006, Total of 3 Pages.

Kalnins, J.G., "The use of electric mutipole lenses for bending and focusing polar molecules with application to the design of a rotational-state separator", Proc. of PAC 2003, Portland, OR, USA, May 2003, pp. 2951-2953.

Kim, et al., "50MEV Proton Beam Test Facility for Low Flux Beam Utilization Studies of PEFP", Proceedings of APAC 2004, Gyeongju, Korea, Oct. 2005, pp. 441-443.

(56) References Cited

OTHER PUBLICATIONS

Lapostolle, P., "Introduction a la theorie des accelerateurs lineaires", CERN Yellow Books, CERN87-09, Geneva, Switzerland, Jul. 1987, pp. 4-5.

Li, Yulin, "A Thin Beryllium Injection Window for CESR-C", Proc. PAC '03, Portland, Oregon, USA, May 2001, pp. 2264-2266.

Noda, et al., "Performance of a respiration-gated beam control system for patient treatment", Proc. EPAC 96, Barcelona, Spain, Jun. 1996, pp. 2656-2658.

Noda, et al., "Slow beam extraction by a transverse RF field with AM and FM", Nuclear Instruments & Methods in Physics Research, Section—A: Accelerators, Spectrometers, Detectors and Associated Equipment, vol. A 374, Amsterdam, NL, May 1996, pp. 269-277.

Peters, J., "Negative ion sources for high energy accelerators (invited)", Review of Scientific Instruments, AIP, vol. 71, No. 2, Melville, NY, US, Feb. 2000, pp. 1069-1074.

Pohlit, W., "Optimization of Cancer Treatment with Accelerator Produced Radiations", Proc. EPAC '98, Stockholm, Sweden, Jun. 1998, pp. 192-194.

Saito, et al., "RF Accelerating System for a Compact Ion Synchrotron", Proc. of 2001 PAC, Chicago, USA, Jun. 2001, pp. 966-968.

Suda, et al., "Medical application of the positron emitter beam at HIMAC", Proc. of EPAC 2000, Vienna, Austria, Jun. 2000, pp. 2554-2556.

Tanigaki, et al., "Construction of FFAG Accelerators in KURRI for ADS Study", Proc. of 2005, Knoxville, TN, USA, May 2005, pp. 350-352.

Trbojevic, et al., "Design of a Non-Scaling FFAG Accelerator for Proton Therapy", Proc. of 2004 Cyclotron Conf., Tokyo, Japan, Oct. 2004, Total of 3 pages.

Winkler, et al., "Charge Exchange Extraction at the Experimental Storage Ring ESR at GSI", Proc. of EPAC 98, Stockholm Sweden, Jun. 1998, pp. 559-561.

"Proton-Ion Medical Machine Study (PIMMS) Part II", European Organization for Nuclear Research CERN- PS Division, Jul. 27, 2000, pp. 1-352.

Arimoto, et al., "A Study of the PRISM-FFAG Magnet", Proc. of Cyclotron 2004 Conference, Tokyo, Japan, Oct. 2004, 243-245, plus 30 page presentation.

Rigney, et al., "Patient Positioning System for Radiation Therapy System", Mexican patent application No. PA/a/2006/001581, Corresponds to WO2005018734, published Mar. 3, 2005, May 2006.

Sugai, I. et al., "Development of thick, long-lived carbon stripper foils for PSR of LANL", Nuclear Instruments & Methods in Physics Research, Section-A, vol. 362 No. 1, Aug. 1, 1995, pp. 70-76.

\* cited by examiner

MULTI-FIELD CHARGED PARTICLE CANCER THERAPY METHOD AND APPARATUS

CROSS REFERENCES TO RELATED APPLICATIONS

This application claims the benefit of:
U.S. provisional patent application No. 61/055,395 filed May 22, 2008;
U.S. provisional patent application No. 61/137,574 filed Aug. 1, 2008;
U.S. provisional patent application No. 61/192,245 filed Sep. 17, 2008;
U.S. provisional patent application No. 61/055,409 filed May 22, 2008;
U.S. provisional patent application No. 61/203,308 filed Dec. 22, 2008;
U.S. provisional patent application No. 61/188,407 filed Aug. 11, 2008;
U.S. provisional patent application No. 61/209,529 filed Mar. 9, 2009;
U.S. provisional patent application No. 61/188,406 filed Aug. 11, 2008;
U.S. provisional patent application No. 61/189,815 filed Aug. 25, 2008;
U.S. provisional patent application No. 61/208,182 filed Feb. 23, 2009;
U.S. provisional patent application No. 61/201,731 filed Dec. 15, 2008;
U.S. provisional patent application No. 61/208,971 filed Mar. 3, 2009;
U.S. provisional patent application No. 61/205,362 filed Jan. 21, 2009;
U.S. provisional patent application No. 61/134,717 filed Jul. 14, 2008;
U.S. provisional patent application No. 61/134,707 filed Jul. 14, 2008;
U.S. provisional patent application No. 61/201,732 filed Dec. 15, 2008;
U.S. provisional patent application No. 61/198,509 filed Nov. 7, 2008;
U.S. provisional patent application No. 61/134,718 filed Jul. 14, 2008;
U.S. provisional patent application No. 61/190,613 filed Sep. 2, 2008;
U.S. provisional patent application No. 61/191,043 filed Sep. 8, 2008;
U.S. provisional patent application No. 61/192,237 filed Sep. 17, 2008,
U.S. provisional patent application No. 61/201,728 filed Dec. 15, 2008;
U.S. provisional patent application No. 61/190,546 filed Sep. 2, 2008;
U.S. provisional patent application No. 61/189,017 filed Aug. 15, 2008;
U.S. provisional patent application No. 61/198,248 filed Nov. 5, 2008;
U.S. provisional patent application No. 61/198,508 filed Nov. 7, 2008;
U.S. provisional patent application No. 61/197,971 filed Nov. 3, 2008;
U.S. provisional patent application No. 61/199,405 filed Nov. 17, 2008;
U.S. provisional patent application No. 61/199,403 filed Nov. 17, 2008;
U.S. provisional patent application No. 61/199,404 filed Nov. 17, 2008; and
claims priority to PCT patent application no. PCT/RU2009/00105, "Multi-Field Charged Particle Cancer Therapy Method and Apparatus", filed Mar. 4, 2009;
all of which are incorporated herein in their entirety by this reference thereto.

BACKGROUND OF THE INVENTION

1. Field of the Invention

This invention relates generally to treatment of solid cancers. More particularly, the invention relates to charged particle irradiation beam control in cancer therapy.

2. Discussion of the Prior Art

Cancer Treatment

Several distinct forms of radiation therapy exist for cancer treatment including: brachytherapy, traditional electromagnetic X-ray therapy, and proton therapy. Proton therapy systems typically include: a beam generator, an accelerator, and a beam transport system to move the resulting accelerated protons to a plurality of treatment rooms where the protons are delivered to a tumor in a patient's body.

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Charged Particle Cancer Therapy

Patents related to the current invention are summarized here.

Proton Beam Therapy System

F. Cole, et. al. of Loma Linda University Medical Center "Multi-Station Proton Beam Therapy System", U.S. Pat. No. 4,870,287 (Sep. 26, 1989) describe a proton beam therapy system for selectively generating and transporting proton beams from a single proton source and accelerator to a selected treatment room of a plurality of patient treatment rooms.

Gantry

T. Yamashita, et. al. "Rotating Irradiation Apparatus", U.S. Pat. No. 7,381,979 (Jun. 3, 2008) describe a rotating gantry having a front ring and a rear ring, each ring having radial support devices, where the radial support devices have linear guides. The system has thrust support devices for limiting movement of the rotatable body in the direction of the rotational axis of the rotatable body.

T. Yamashita, et. al. "Rotating Gantry of Particle Beam Therapy System" U.S. Pat. No. 7,372,053 (May 13, 2008) describe a rotating gantry supported by an air braking system allowing quick movement, braking, and stopping of the gantry during irradiation treatment.

M. Yanagisawa, et. al. "Medical Charged Particle Irradiation Apparatus", U.S. Pat. No. 6,992,312 (Jan. 31, 2006); M. Yanagisawa, et. al. "Medical Charged Particle Irradiation Apparatus", U.S. Pat. No. 6,979,832 (Dec. 27, 2005); and M. Yanagisawa, et. al. "Medical Charged Particle Irradiation Apparatus", U.S. Pat. No. 6,953,943 (Oct. 11, 2005) all describe an apparatus capable of irradiation from upward and horizontal directions. The gantry is rotatable about an axis of rotation where the irradiation field forming device is eccentrically arranged, such that an axis of irradiation passes through a different position than the axis of rotation.

H. Kaercher, et. al. "Isokinetic Gantry Arrangement for the Isocentric Guidance of a Particle Beam And a Method for Constructing Same", U.S. Pat. No. 6,897,451 (May 24, 2005) describe an isokinetic gantry arrangement for isocentric guidance of a particle beam that can be rotated around a horizontal longitudinal axis.

G. Kraft, et. al. "Ion Beam System for Irradiating Tumor Tissues", U.S. Pat. No. 6,730,921 (May 4, 2004) describe an ion beam system for irradiating tumor tissues at various irradiation angles in relation to a horizontally arranged patient couch, where the patient couch is rotatable about a center axis and has a lifting mechanism. The system has a central ion beam deflection of up to ±15 degrees with respect to a horizontal direction.

M. Pavlovic, et. al. "Gantry System and Method for Operating Same", U.S. Pat. No. 6,635,882 (Oct. 21, 2003) describe a gantry system for adjusting and aligning an ion beam onto a target from a freely determinable effective treatment angle. The ion beam is aligned on a target at adjustable angles of from 0 to 360 degrees around the gantry rotation axis and at an angle of 45 to 90 degrees off of the gantry rotation axis yielding a cone of irradiation when rotated a full revolution about the gantry rotation axis.

Movable Patient

N. Rigney, et. al. "Patient Alignment System with External Measurement and Object Coordination for Radiation Therapy System", U.S. Pat. No. 7,199,382 (Apr. 3, 2007) describe a patient alignment system for a radiation therapy system that includes multiple external measurement devices that obtain position measurements of movable components of the radiation therapy system. The alignment system uses the external measurements to provide corrective positioning feedback to more precisely register the patient to the radiation beam.

Y. Muramatsu, et. al. "Medical Particle Irradiation Apparatus", U.S. Pat. No. 7,030,396 (Apr. 18, 2006); Y. Muramatsu, et. al. "Medical Particle Irradiation Apparatus", U.S. Pat. No. 6,903,356 (Jun. 7, 2005); and Y. Muramatsu, et. al. "Medical Particle Irradiation Apparatus", U.S. Pat. No. 6,803,591 (Oct. 12, 2004) all describe a medical particle irradiation apparatus having a rotating gantry, an annular frame located within the gantry such that it can rotate relative to the rotating gantry, an anti-correlation mechanism to keep the frame from rotating with the gantry, and a flexible moving floor engaged with the frame in such a manner to move freely with a substantially level bottom while the gantry rotates.

H. Nonaka, et. al. "Rotating Radiation Chamber for Radiation Therapy", U.S. Pat. No. 5,993,373 (Nov. 30, 1999) describe a horizontal movable floor composed of a series of multiple plates that are connected in a free and flexible manner, where the movable floor is moved in synchrony with rotation of a radiation beam irradiation section.

Patient Positioning

Y. Nagamine, et. al. "Patient Positioning Device and Patient Positioning Method", U.S. Pat. No. 7,212,609 (May 1, 2007) and Y. Nagamine, et. al. "Patient Positioning Device and Patient Positioning Method", U.S. Pat. No. 7,212,608 (May 1, 2007) describe a patient positioning system that compares a comparison area of a reference X-ray image and a current X-ray image of a current patient location using pattern matching.

D. Miller, et. al. "Modular Patient Support System", U.S. Pat. No. 7,173,265 (Feb. 6, 2007) describe a radiation treatment system having a patient support system that includes a modularly expandable patient pod and at least one immobilization device, such as a moldable foam cradle.

K. Kato, et. al. "Multi-Leaf Collimator and Medical System Including Accelerator", U.S. Pat. No. 6,931,100 (Aug. 16, 2005); K. Kato, et. al. "Multi-Leaf Collimator and Medical System Including Accelerator", U.S. Pat. No. 6,823,045 (Nov. 23, 2004); K. Kato, et. al. "Multi-Leaf Collimator and Medical System Including Accelerator", U.S. Pat. No. 6,819,743 (Nov. 16, 2004); and K. Kato, et. al. "Multi-Leaf Collimator and Medical System Including Accelerator", U.S. Pat. No. 6,792,078 (Sep. 14, 2004) all describe a system of leaf plates used to shorten positioning time of a patient for irradiation therapy. Motor driving force is transmitted to a plurality of leaf plates at the same time through a pinion gear. The system also uses upper and lower air cylinders and upper and lower guides to position a patient.

Problem

There exists in the art of particle beam therapy of cancerous tumors a need for charged particle irradiation beam control. More particularly, there exists in the art a need for efficient delivery of charged particles to the tumor, where efficiency is the fraction of energy deposited in the tumor relative to the fraction of energy deposited in healthy tissue.

SUMMARY OF THE INVENTION

The invention comprises a multi-field charged particle irradiation beam method and apparatus used in radiation therapy of cancerous tumors.

DETAILED DESCRIPTION OF THE INVENTION

Figure 1:
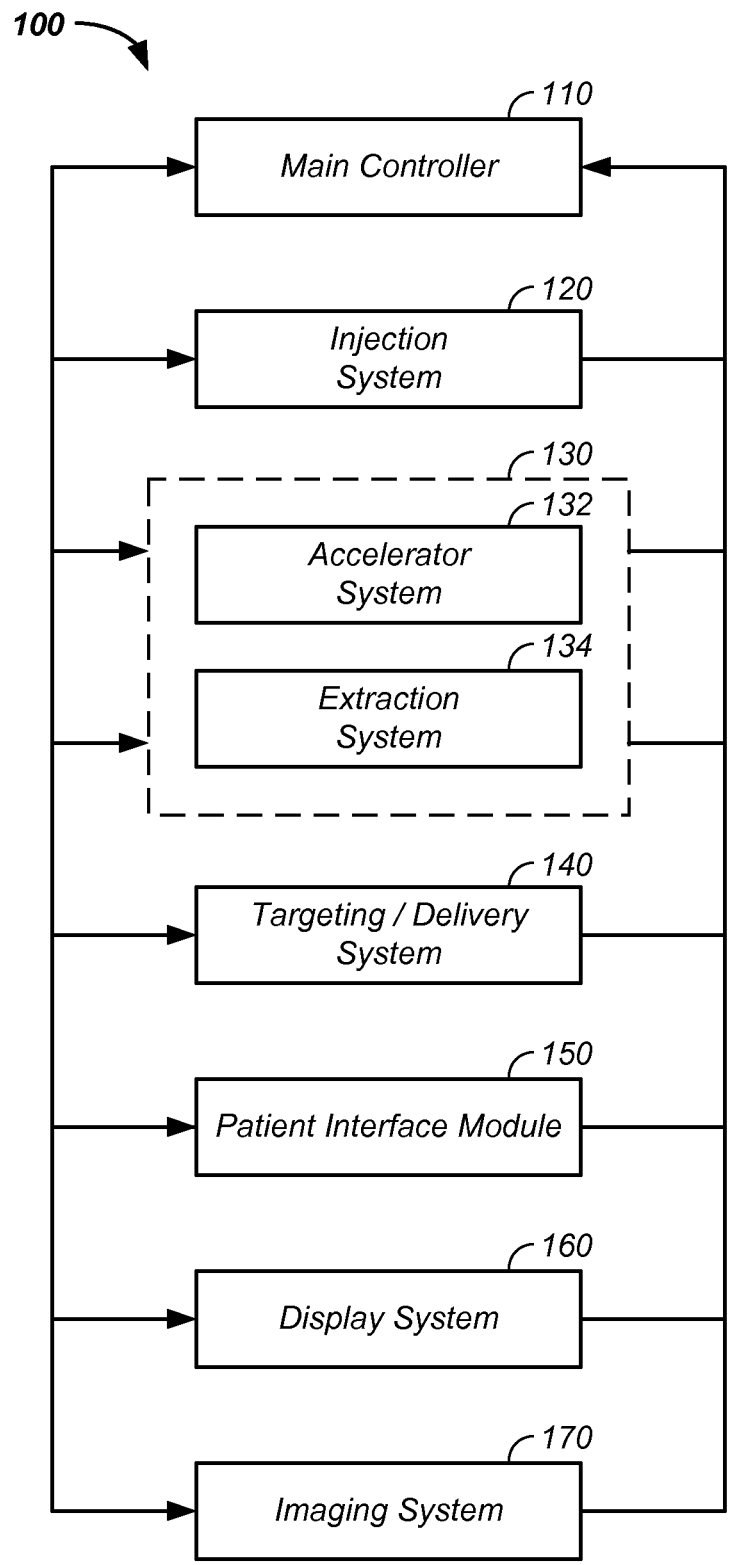
FIG. 1 illustrates component connections of a particle beam therapy system.

The invention comprises a multi-field charged particle irradiation beam method and apparatus used in radiation therapy of cancerous tumors.

In one embodiment, a method and apparatus for efficient radiation dose delivery to a tumor is described. Preferably, radiation is delivered through an entry point into the tumor and Bragg peak energy is targeted to a distal or far side of the tumor from an ingress point. Delivering Bragg peak energy to the distal side of the tumor from the ingress point is repeated from multiple rotational directions. Beam intensity is proportional to radiation dose delivery efficiency. The multi-field irradiation process with energy levels targeting the far side of the tumor from each irradiation direction provides even and efficient charged particle radiation dose delivery to the tumor. Preferably, the charged particle therapy is timed to patient respiration via control of charged particle beam injection, acceleration, extraction, and/or targeting methods and apparatus.

For example, radiation is delivered through an entry point into the tumor and Bragg peak energy is targeted to a distal or far side of the tumor from an ingress point. Delivering Bragg peak energy to the distal side of the tumor from the ingress point is repeated from multiple rotational directions. Preferably, beam intensity is proportional to radiation dose delivery efficiency. Preferably, the charged particle therapy is timed to patient respiration via control of charged particle beam injection, acceleration, extraction, and/or targeting methods and apparatus. Optionally, multi-axis control of the charged particle beam is used simultaneously with the multi-field irradiation. Combined, the system allows multi-field and multi-axis charged particle irradiation of tumors yielding precise and accurate irradiation dosages to a tumor with distribution of harmful ingress energy about the tumor.

In another embodiment, the system relates to a combined rotation/raster method and apparatus, referred to as multi-field charged particle cancer therapy. The system uses a fixed orientation charged particle source, such as a proton source, relative to a rotating patient to yield tumor irradiation from multiple directions. Preferably, the system combines layer-wise tumor irradiation from many directions with controlled energy proton irradiation to deliver peak proton beam energy within a selected tumor volume or irradiated slice. Optionally, the selected tumor volume for irradiation from a given angle is a distal portion of the tumor. In this manner ingress Bragg peak energy is circumferentially spread about the tumor minimizing damage to healthy tissue and peak proton energy is efficiently, accurately, and precisely delivered to the tumor.

In yet another embodiment, a multi-field imaging and a multi-field charged particle cancer therapy method and apparatus is used that is coordinated with patient respiration via use of feedback sensors used to monitor and/or control patient respiration. Optionally, the respiration monitoring system uses thermal and/or force sensors to determine where a patient is in a respiration cycle in combination with a feedback signal control delivered to the patient to inform the patient when breath control is required. Preferably, the multi-field imaging, such as X-ray imaging, and the charged particle therapy are performed on a patient in a partially immobilized and repositionable position. X-ray and/or proton delivery is timed to patient respiration via control of charged particle beam injection, acceleration, extraction, and/or targeting methods and apparatus.

In still yet another embodiment, a multi-axis charged particle irradiation method and apparatus is described, optionally used in combination with multi-field irradiation. The multi-axis controls includes separate control of one or more of horizontal or x-axis position, vertical or y-axis position, energy control, and intensity control of the charged particle irradiation beam. Optionally, the separate control is independent control. Optionally, the charged particle beam is additionally controlled in terms of timing. Timing is coordinated with patient respiration and/or patient rotational positioning. Combined, the system allows multi-axis and multi-field charged particle irradiation of tumors yielding precise and accurate irradiation dosages to a tumor with distribution of harmful healthy tissue volume ingress energy about the tumor.

In another embodiment, the system uses a radio-frequency (RF) cavity system to induce betatron oscillation of a charged particle stream. Sufficient amplitude modulation of the charged particle stream causes the charged particle stream to hit a material, such as a foil. The foil decreases the energy of the charged particle stream, which decreases a radius of curvature of the charged particle stream in the synchrotron sufficiently to allow a physical separation of the reduced energy charged particle stream from the original charged particle stream. The physically separated charged particle stream is then removed from the system by use of an applied field and deflector.

In still another embodiment, the system comprises intensity control of a charged particle beam acceleration, extraction, and/or targeting method and apparatus used in conjunction with charged particle beam radiation therapy of cancerous tumors. Particularly, intensity of a charged particle stream of a synchrotron is described in combination with turning magnets, edge focusing magnets, concentrating magnetic field magnets, winding and control coils, and extraction elements of the synchrotron. The system reduces the overall size of the synchrotron, provides a tightly controlled proton beam, directly reduces the size of required magnetic fields, directly reduces required operating power, and allows continual acceleration of protons in a synchrotron even during a process of extracting protons from the synchrotron.

Used in combination with the invention, novel design features of a charged particle beam cancer therapy system are described. Particularly, a negative ion beam source with novel features in the negative ion source, ion source vacuum system, ion beam focusing lens, and tandem accelerator is described. Additionally, turning magnets, edge focusing magnets, magnetic field concentration magnets, winding and correction coils, flat magnetic field incident surfaces, and extraction elements are described that minimize the overall size of the synchrotron, provide a tightly controlled proton beam, directly reduce the size of required magnetic fields, directly reduce required operating power, and allow continual acceleration of protons in a synchrotron even during a process of extracting protons from the synchrotron. The ion beam source system and synchrotron are preferably computer integrated with a patient imaging system and a patient interface including respiration monitoring sensors and patient positioning elements. Further, intensity control of a charged particle beam acceleration, extraction, and/or targeting method and apparatus used in conjunction with charged particle beam radiation therapy of cancerous tumors is described. More particularly, intensity, energy, and timing control of a charged particle stream of a synchrotron is described. The synchrotron control elements allow tight control of the charged particle beam, which compliments the tight control of patient positioning to yield efficient treatment of a solid tumor with reduced tissue damage to surrounding healthy tissue. In addition, the system reduces the overall size of the synchrotron, provides a tightly controlled proton beam, directly reduces the size of required magnetic fields, directly reduces required operating power, and allows continual acceleration of protons in a synchrotron even during a process of extracting protons from the synchrotron. All of these systems are preferably used in conjunction with an X-ray system capable of collecting X-rays of a patient in (1) a positioning system for proton treatment and (2) at a specified moment of the patient's respiration cycle. Combined, the systems provide for efficient, accurate, and precise noninvasive tumor treatment with minimal damage to surrounding healthy tissue.

Cyclotron/Synchrotron

A cyclotron uses a constant magnetic field and a constant-frequency applied electric field. One of the two fields is varied in a synchrocyclotron. Both of these fields are varied in a synchrotron. Thus, a synchrotron is a particular type of cyclic particle accelerator in which a magnetic field is used to turn the particles so they circulate and an electric field is used to accelerate the particles. The synchroton carefully synchronizes the applied fields with the travelling particle beam.

By increasing the fields appropriately as the particles gain energy, the charged particles path can be held constant as they are accelerated. This allows the vacuum container for the particles to be a large thin torus. In reality it is easier to use some straight sections between the bending magnets and some turning sections giving the torus the shape of a round-cornered polygon. A path of large effective radius is thus constructed using simple straight and curved pipe segments, unlike the disc-shaped chamber of the cyclotron type devices. The shape also allows and requires the use of multiple magnets to bend the particle beam.

The maximum energy that a cyclic accelerator can impart is typically limited by the strength of the magnetic fields and the minimum radius/maximum curvature, of the particle path. In a cyclotron the maximum radius is quite limited as the particles start at the center and spiral outward, thus this entire path must be a self-supporting disc-shaped evacuated chamber. Since the radius is limited, the power of the machine becomes limited by the strength of the magnetic field. In the case of an ordinary electromagnet, the field strength is limited by the saturation of the core because when all magnetic domains are aligned the field may not be further increased to any practical extent. The arrangement of the single pair of magnets also limits the economic size of the device.

Synchrotrons overcome these limitations, using a narrow beam pipe surrounded by much smaller and more tightly focusing magnets. The ability of this device to accelerate particles is limited by the fact that the particles must be charged to be accelerated at all, but charged particles under acceleration emit photons, thereby losing energy. The limiting beam energy is reached when the energy lost to the lateral acceleration required to maintain the beam path in a circle equals the energy added each cycle. More powerful accelerators are built by using large radius paths and by using more numerous and more powerful microwave cavities to accelerate the particle beam between corners. Lighter particles, such as electrons, lose a larger fraction of their energy when turning. Practically speaking, the energy of electron/positron accelerators is limited by this radiation loss, while it does not play a significant role in the dynamics of proton or ion accelerators. The energy of those is limited strictly by the strength of magnets and by the cost.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system. Any charged particle beam system is equally applicable to the techniques described herein.

Referring now to FIG. 1, a charged particle beam system 100 is illustrated. The charged particle beam preferably comprises a number of subsystems including any of: a main controller or irradiation control module 110; an injection system 120; a synchrotron 130 that typically includes: (1) an accelerator system 132 and (2) an extraction system 134; a scanning/targeting/delivery system 140; a patient interface module 150; a display system 160; and/or an imaging system 170.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 then optionally controls the injection system 120 to inject a proton into a synchrotron 130. The synchrotron typically contains at least an accelerator system 132 and an extraction system 134. The main controller preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the scanning/targeting/delivery system 140 to the patient interface module 150. One or more components of the patient interface module 150 are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Synchrotron

Herein, the term synchrotron is used to refer to a system maintaining the charged particle beam in a circulating path; however, cyclotrons are alternatively used, albeit with their inherent limitations of energy, intensity, and extraction control. Further, the charged particle beam is referred to herein as circulating along a circulating path about a central point of the synchrotron. The circulating path is alternatively referred to as an orbiting path; however, the orbiting path does not refer a perfect circle or ellipse, rather it refers to cycling of the protons around a central point or region.

Figure 2:
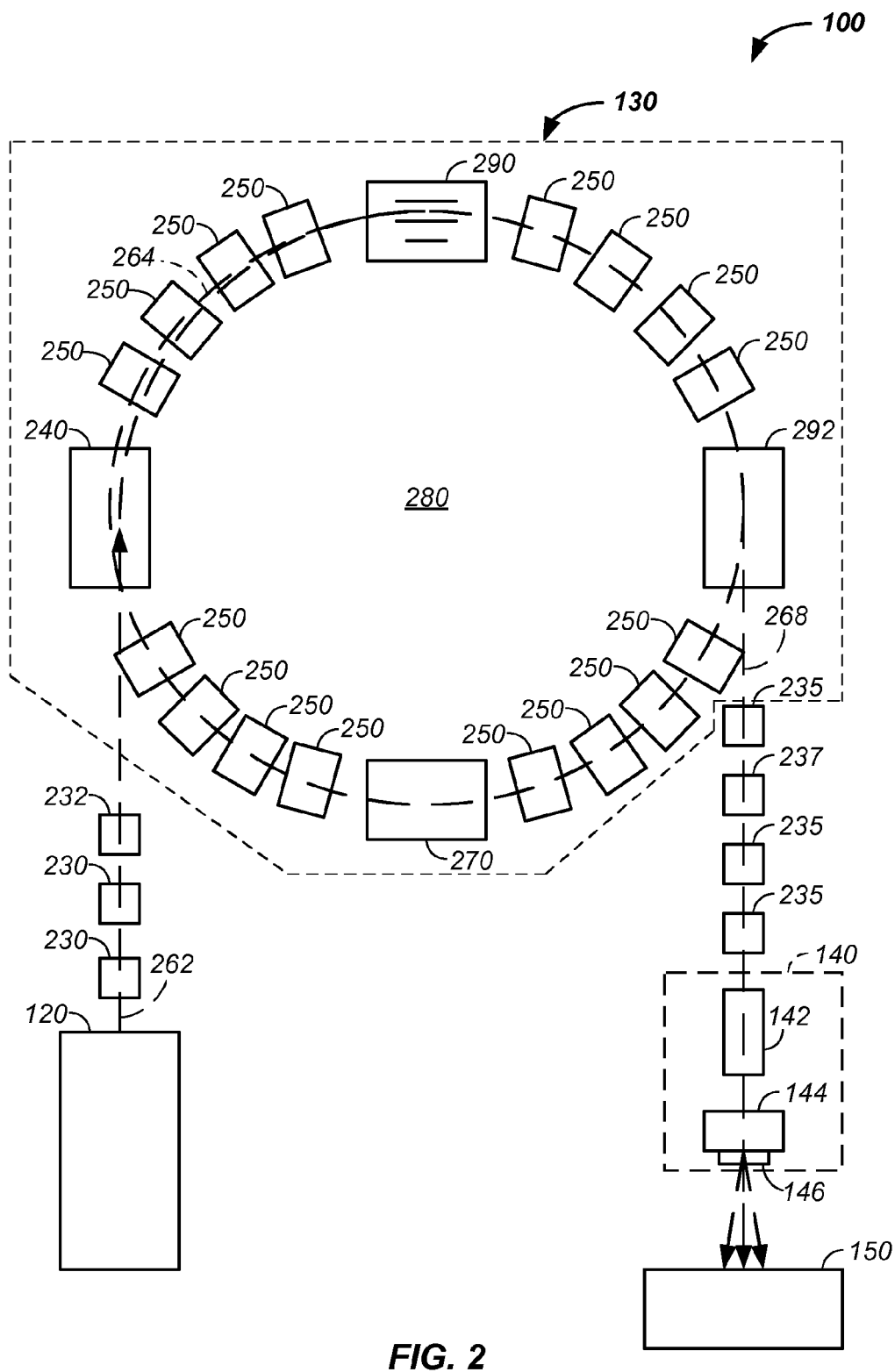
FIG. 2 illustrates a charged particle therapy system.

Referring now to FIG. 2, an illustrative exemplary embodiment of one version of the charged particle beam system 100 is provided. The number, position, and described type of components is illustrative and non-limiting in nature. In the illustrated embodiment, an injector system 210 or ion source or charged particle beam source generates protons. The protons are delivered into a vacuum tube that runs into, through, and out of the synchrotron. The generated protons are delivered along an initial path 262. Focusing magnets 230, such as quadrupole magnets or injection quadrupole magnets, are used to focus the proton beam path. A quadrupole magnet is a focusing magnet. An injector bending magnet 232 bends the proton beam toward the plane of the synchrotron 130. The focused protons having an initial energy are introduced into an injector magnet 240, which is preferably an injection Lamberson magnet. Typically, the initial beam path 262 is along an axis off of, such as above, a circulating plane of the synchrotron 130. The injector bending magnet 232 and injector magnet 240 combine to move the protons into the synchrotron 130. Main bending magnets 250 or dipole magnets or circulating magnets are used to turn the protons along a circulating beam path 264. A dipole magnet is a bending magnet. The main bending magnets 250 bend the initial beam path 262 into a circulating beam path 264. In this example, the main bending magnets 250 or circulating magnets are represented as four sets of four magnets to maintain the circulating beam path 264 into a stable circulating beam path. However, any number of magnets or sets of magnets are optionally used to move the protons around a single orbit in the circulation process. The protons pass through an accelerator 270. The accelerator accelerates the protons in the circulating beam path 264. As the protons are accelerated, the fields applied by the magnets are increased. Particularly, the speed of the protons achieved by the accelerator 270 are synchronized with magnetic fields of the main bending magnets 250 or circulating magnets to maintain stable circulation of the protons about a central point or region 280 of the synchrotron. At separate points in time the accelerator 270/main bending magnet 250 combination is used to accelerate and/or decelerate the circulating protons while maintaining the protons in the circulating path or orbit. An extraction element of the inflector/deflector system 290 is used in combination with a Lamberson extraction magnet 292 to remove protons from their circulating beam path 264 within the synchrotron 130. One example of a deflector component is a Lamberson magnet. Typically the deflector moves the protons from the circulating plane to an axis off of the circulating plane, such as above the circulating plane. Extracted protons are preferably directed and/or focused using an extraction bending magnet 237 and extraction focusing magnets 235, such as quadrupole magnets along a transport path 268 into the scanning/targeting/delivery system 140. Two components of a scanning system 140 or targeting system typically include a first axis control 142, such as a vertical control, and a second axis control 144, such as a horizontal control. In one embodiment, the first axis control 142 allows for about 100 mm of vertical scanning of the proton beam 268 and the second axis control 144 allows for about 700 mm of horizontal scanning of the proton beam 268. A nozzle system 146 is used for imaging the proton beam and/or as a vacuum barrier between the low pressure beam path of the synchrotron and the atmosphere. Protons are delivered with control to the patient interface module 150 and to a tumor of a patient. All of the above listed elements are optional and may be used in various permutations and combinations.

Ion Beam Generation System

An ion beam generation system generates a negative ion beam, such as a hydrogen anion or H⁻ beam; preferably focuses the negative ion beam; converts the negative ion beam to a positive ion beam, such as a proton or H⁺ beam; and injects the positive ion beam into the synchrotron 130. Portions of the ion beam path are preferably under partial vacuum. Each of these systems are further described, infra.

Figure 3:
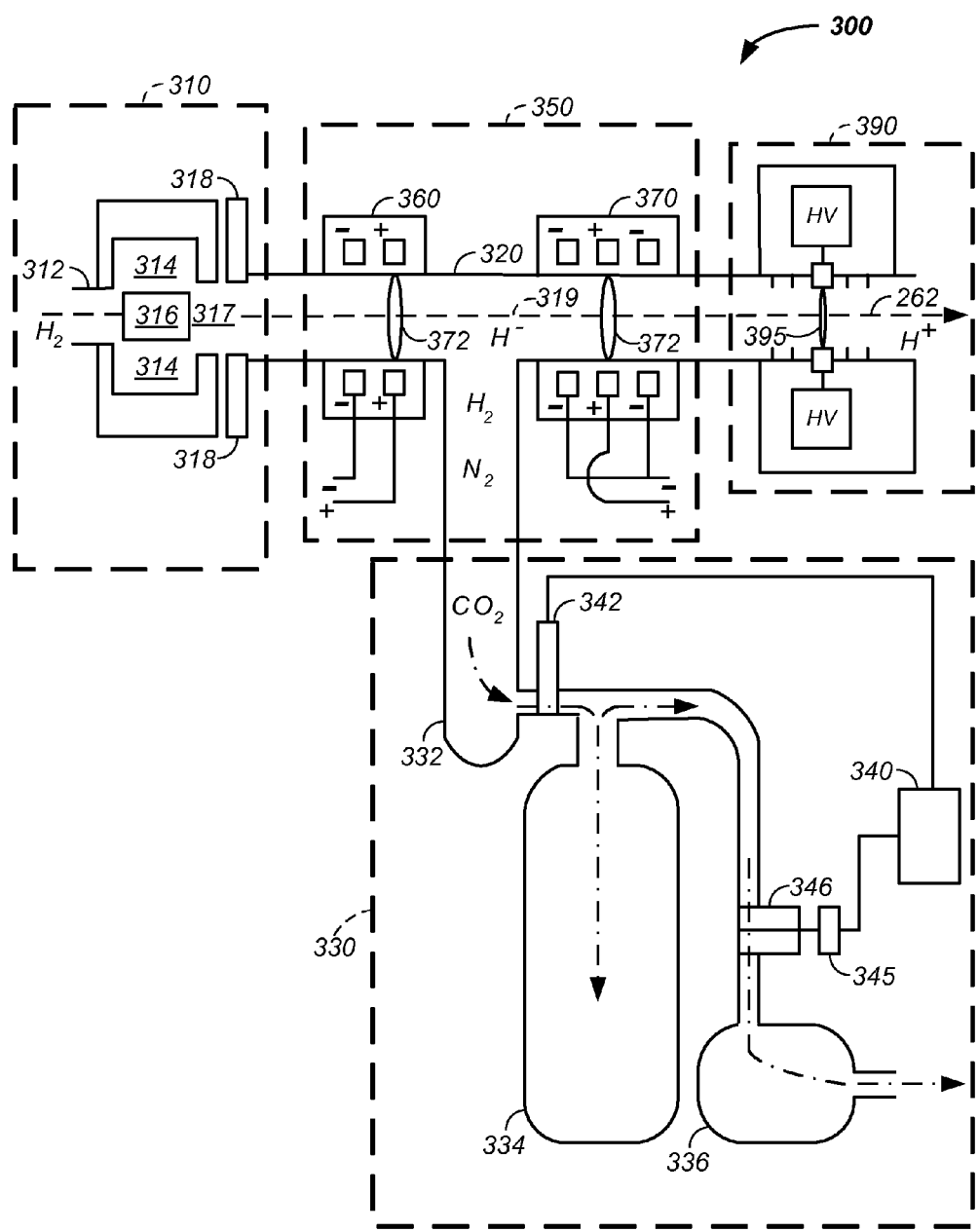
FIG. 3 illustrates an ion beam generation system.

Referring now to FIG. 3, an exemplary ion beam generation system 300 is illustrated. As illustrated, the ion beam generation system 300 has four major elements: a negative ion source 310, a first partial vacuum system 330, an optional ion beam focusing system 350, and a tandem accelerator 390.

Still referring to FIG. 3, the negative ion source 310 preferably includes an inlet port 312 for injection of hydrogen gas into a high temperature plasma chamber 314. In one embodiment, the plasma chamber includes a magnetic material 316, which provides a magnetic field barrier 317 between the high temperature plasma chamber 314 and a low temperature plasma region on the opposite side of the magnetic field barrier. An extraction pulse is applied to a negative ion extraction electrode 318 to pull the negative ion beam into a negative ion beam path 319, which proceeds through the first partial vacuum system 330, through the ion beam focusing system 350, and into the tandem accelerator 390.

Still referring to FIG. 3, the first partial vacuum system 330 is an enclosed system running from the hydrogen gas inlet port 312 to the tandem accelerator 390 foil 395. The foil 395 is sealed directly or indirectly to the edges of the vacuum tube 320 providing for a higher pressure, such as about $10^{-5}$ torr, to be maintained on the first partial vacuum system 330 side of the foil 395 and a lower pressure, such as about $10^{-7}$ torr, to be maintained on the synchrotron side of the foil 390. By only pumping first partial vacuum system 330 and by only semi-continuously operating the ion beam source vacuum based on sensor readings, the lifetime of the semi-continuously operating pump is extended. The sensor readings are further described, infra.

Still referring to FIG. 3, the first partial vacuum system 330 preferably includes: a first pump 332, such as a continuously operating pump and/or a turbo molecular pump; a large holding volume 334; and a semi-continuously operating pump 336. Preferably, a pump controller 340 receives a signal from a pressure sensor 342 monitoring pressure in the large holding volume 334. Upon a signal representative of a sufficient pressure in the large holding volume 334, the pump controller 340 instructs an actuator 345 to open a valve 346 between the large holding volume and the semi-continuously operating pump 336 and instructs the semi-continuously operating pump to turn on and pump to atmosphere residual gases out of the vacuum line 320 about the charged particle stream. In this fashion, the lifetime of the semi-continuously operating pump is extended by only operating semi-continuously and as needed. In one example, the semi-continuously operating pump 336 operates for a few minutes every few hours, such as 5 minutes every 4 hours, thereby extending a pump with a lifetime of about 2,000 hours to about 96,000 hours.

Further, by isolating the inlet gas from the synchrotron vacuum system, the synchrotron vacuum pumps, such as turbo molecular pumps can operate over a longer lifetime as the synchrotron vacuum pumps have fewer gas molecules to deal with. For example, the inlet gas is primarily hydrogen gas but may contain impurities, such as nitrogen and carbon dioxide. By isolating the inlet gases in the negative ion source system 310, first partial vacuum system 330, ion beam focusing system 350 and negative ion beam side of the tandem accelerator 390, the synchrotron vacuum pumps can operate at lower pressures with longer lifetimes, which increases the efficiency of the synchrotron 130.

Still referring to FIG. 3, the ion beam focusing system 350 includes two or more electrodes where one electrode of each electrode pair partially obstructs the ion beam path with conductive paths 372, such as a conductive mesh. In the illustrated example, three ion beam focusing system sections are illustrated, a two electrode ion focusing section 360, a first three electrode ion focusing section 370, and a second three electrode ion focusing section 380. In a given electrode pair, electric field lines, running between the conductive mesh of a first electrode and a second electrode, provide inward forces focusing the negative ion beam. Multiple such electrode pairs provide multiple negative ion beam focusing regions. Preferably the two electrode ion focusing section 360, first three electrode ion focusing section 370, and second three electrode ion focusing section 380 are placed after the negative ion source and before the tandem accelerator and/or cover a space of about 0.5, 1, or 2 meters along the ion beam path. Ion beam focusing systems are further described, infra.

Still referring to FIG. 3, the tandem accelerator 390 preferably includes a foil 395, such as a carbon foil. The negative ions in the negative ion beam path 319 are converted to positive ions, such as protons, and the initial ion beam path 262 results. The foil 395 is preferably sealed directly or indirectly to the edges of the vacuum tube 320 providing for a higher pressure, such as about $10^{-5}$ torr, to be maintained on the side of the foil 395 having the negative ion beam path 319 and a lower pressure, such as about $10^{-7}$ torr, to be maintained on the side of the foil 390 having the proton ion beam path 262. Having the foil 395 physically separating the vacuum chamber 320 into two pressure regions allows for a system having fewer and/or smaller pumps to maintain the lower pressure system in the synchrotron 130 as the inlet hydrogen and its residuals are extracted in a separate contained and isolated space by the first partial vacuum system 330.

Referring again to FIG. 1, another exemplary method of use of the charged particle beam system 100 is provided. The main controller 110, or one or more sub-controllers, controls one or more of the subsystems to accurately and precisely deliver protons to a tumor of a patient. For example, the main controller sends a message to the patient indicating when or how to breath. The main controller 110 obtains a sensor reading from the patient interface module, such as a temperature breath sensor or a force reading indicative of where in a breath cycle the subject is. The main controller collects an image, such as a portion of a body and/or of a tumor, from the imaging system 170. The main controller 110 also obtains position and/or timing information from the patient interface module 150. The main controller 110 then optionally controls the injection system 120 to inject hydrogen gas into a negative ion beam source 310 and controls timing of extraction of the negative ion from the negative ion beam source 310. Optionally, the main controller controls ion beam focusing the ion beam focusing lens system 350; acceleration of the proton beam with the tandem accelerator 390; and/or injection of the proton into the synchrotron 130. The synchrotron typically contains at least an accelerator system 132 and an extraction system 134. The synchrotron preferably contains one or more of: turning magnets, edge focusing magnets, magnetic field concentration magnets, winding and correction coils, and flat magnetic field incident surfaces, some of which contain elements under control by the main controller 110. The main controller preferably controls the proton beam within the accelerator system, such as by controlling speed, trajectory, and/or timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the targeting/delivery system 140 to the patient interface module 150. One or more components of the patient interface module 150 are preferably controlled by the main controller 110, such as vertical position of the patient, rotational position of the patient, and patient chair positioning/stabilization/control elements. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the patient.

Circulating System

A synchrotron 130 preferably comprises a combination of straight sections 410 and ion beam turning sections 420. Hence, the circulating path of the protons is not circular in a synchrotron, but is rather a polygon with rounded corners.

In one illustrative embodiment, the synchrotron 130, which as also referred to as an accelerator system, has four straight elements and four turning sections. Examples of straight sections 410 include the: inflector 240, accelerator 270, extraction system 290, and deflector 292. Along with the four straight sections are four ion beam turning sections 420, which are also referred to as magnet sections or turning sections. Turning sections are further described, infra.

Figure 4:
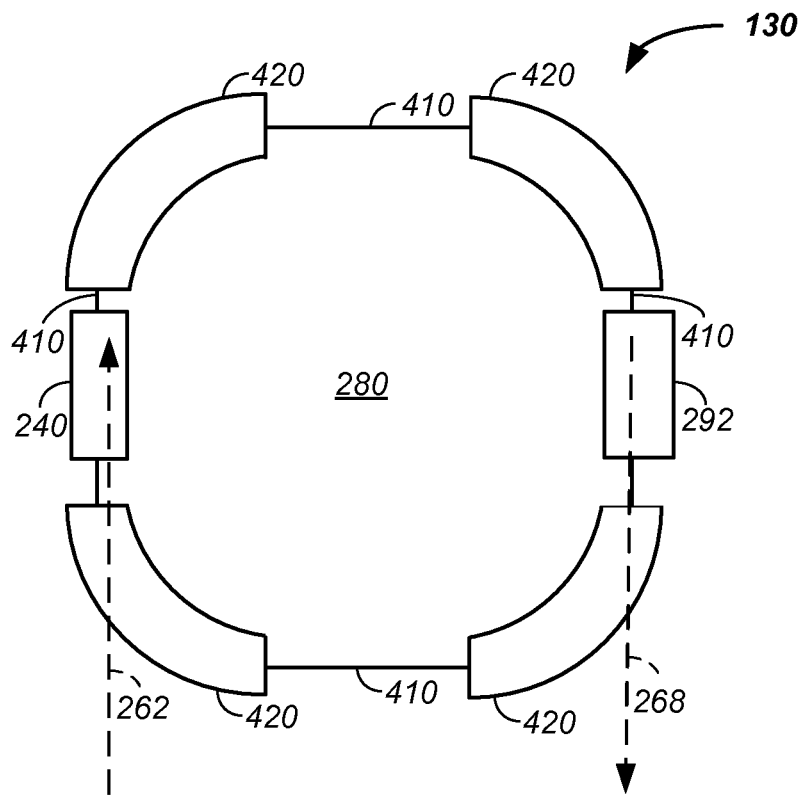
FIG. 4 illustrates straight and turning sections of a synchrotron.

Referring now to FIG. 4, an exemplary synchrotron is illustrated. In this example, protons delivered along the initial proton beam path 262 are inflected into the circulating beam path with the inflector 240 and after acceleration are extracted via a deflector 292 to a beam transport path 268. In this example, the synchrotron 130 comprises four straight sections 410 and four bending or turning sections 420 where each of the four turning sections use one or more magnets to turn the proton beam about ninety degrees. As is further described, infra, the ability to closely space the turning sections and efficiently turn the proton beam results in shorter straight sections. Shorter straight sections allows for a synchrotron design without the use of focusing quadrupoles in the circulating beam path of the synchrotron. The removal of the focusing quadrupoles from the circulating proton beam path results in a more compact design. In this example, the illustrated synchrotron has about a five meter diameter versus eight meter and larger cross-sectional diameters for systems using a quadrupole focusing magnet in the circulating proton beam path.

Figure 5:
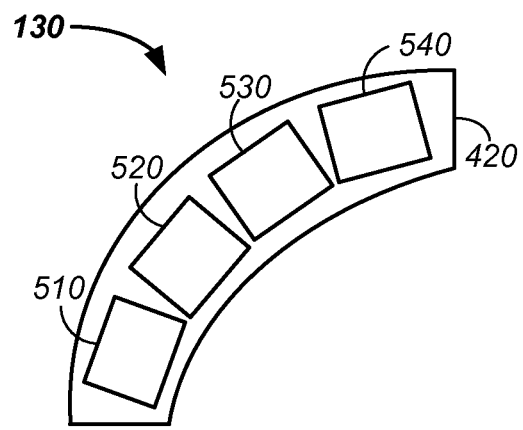
FIG. 5 illustrates bending magnets of a synchrotron.

Referring now to FIG. 5, additional description of the first bending or turning section 420 is provided. Each of the turning sections preferably comprises multiple magnets, such as about 2, 4, 6, 8, 10, or 12 magnets. In this example, four turning magnets 510, 520, 530, 540 in the first turning section 420 are used to illustrate key principles, which are the same regardless of the number of magnets in a turning section 420. A turning magnet 510 is a particular type of main bending or circulating magnet 250.

In physics, the Lorentz force is the force on a point charge due to electromagnetic fields. The Lorentz force is given by equation 1 in terms of magnetic fields with the election field terms not included.

$$F = q(v \times B) \qquad \text{eq. 1}$$

In equation 1, F is the force in newtons; B is the magnetic field in Teslas; and v is the instantaneous velocity of the particles in meters per second.

Figure 6:
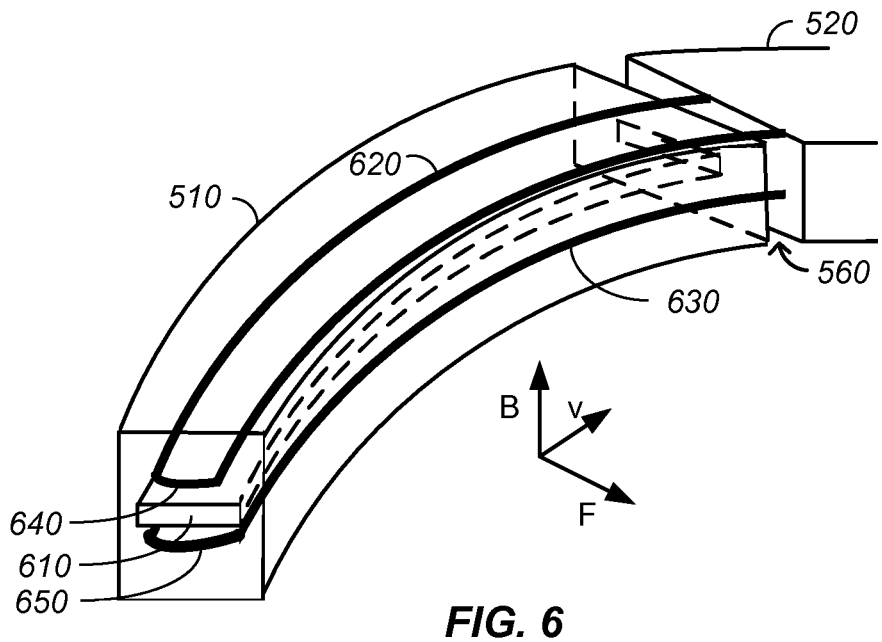
FIG. 6 provides a perspective view of a bending magnet.

Referring now to FIG. 6, an example of a single magnet bending or turning section 510 is expanded. The turning section includes a gap 610 through which protons circulate. The gap 610 is preferably a flat gap, allowing for a magnetic field across the gap 610 that is more uniform, even, and intense. A magnetic field enters the gap 610 through a magnetic field incident surface and exits the gap 610 through a magnetic field exiting surface. The gap 610 runs in a vacuum tube between two magnet halves. The gap 610 is controlled by at least two parameters: (1) the gap 610 is kept as large as possible to minimize loss of protons and (2) the gap 610 is kept as small as possible to minimize magnet sizes and the associated size and power requirements of the magnet power supplies. The flat nature of the gap 610 allows for a compressed and more uniform magnetic field across the gap 610. One example of a gap dimension is to accommodate a vertical proton beam size of about 2 cm with a horizontal beam size of about 5 to 6 cm.

As described, supra, a larger gap size requires a larger power supply. For instance, if the gap 610 size doubles in vertical size, then the power supply requirements increase by about a factor of 4. The flatness of the gap 610 is also important. For example, the flat nature of the gap 610 allows for an increase in energy of the extracted protons from about 250 to about 330 MeV. More particularly, if the gap 610 has an extremely flat surface, then the limits of a magnetic field of an iron magnet are reachable. An exemplary precision of the flat surface of the gap 610 is a polish of less than about 5 microns and preferably with a polish of about 1 to 3 microns. Unevenness in the surface results in imperfections in the applied magnetic field. The polished flat surface spreads unevenness of the applied magnetic field.

Still referring to FIG. 6, the charged particle beam moves through the gap 610 with an instantaneous velocity, v. A first magnetic coil 620 and a second magnetic coil 630 run above and below the gap 610, respectively. Current running through the coils 620, 630 results in a magnetic field, B, running through the single magnet turning section 510. In this example, the magnetic field, B, runs upward, which results in a force, F, pushing the charged particle beam inward toward a central point of the synchrotron, which turns the charged particle beam in an arc.

Still referring to FIG. 6, a portion of an optional second magnet bending or turning section 520 is illustrated. The coils 620, 630 typically have return elements 640, 650 or turns at the end of one magnet, such as at the end of the first magnet turning section 510. The turns 640, 650 take space. The space reduces the percentage of the path about one orbit of the synchrotron that is covered by the turning magnets. This leads to portions of the circulating path where the protons are not turned and/or focused and allows for portions of the circulating path where the proton path defocuses. Thus, the space results in a larger synchrotron. Therefore, the space between magnet turning sections 660 is preferably minimized. The second turning magnet is used to illustrate that the coils 620, 630 optionally run along a plurality of magnets, such as 2, 3, 4, 5, 6, or more magnets. Coils 620, 630 running across multiple turning section magnets allows for two turning section magnets to be spatially positioned closer to each other due to the removal of the steric constraint of the turns, which reduces and/or minimizes the space 660 between two turning section magnets.

Figure 7:
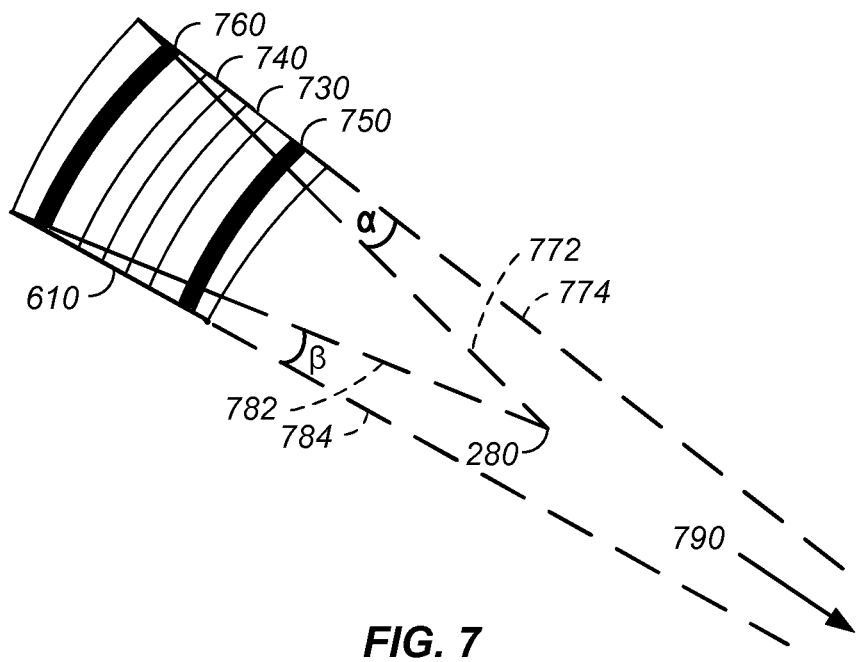
FIG. 7 illustrates a cross-sectional view of a bending magnet.
Figure 8:
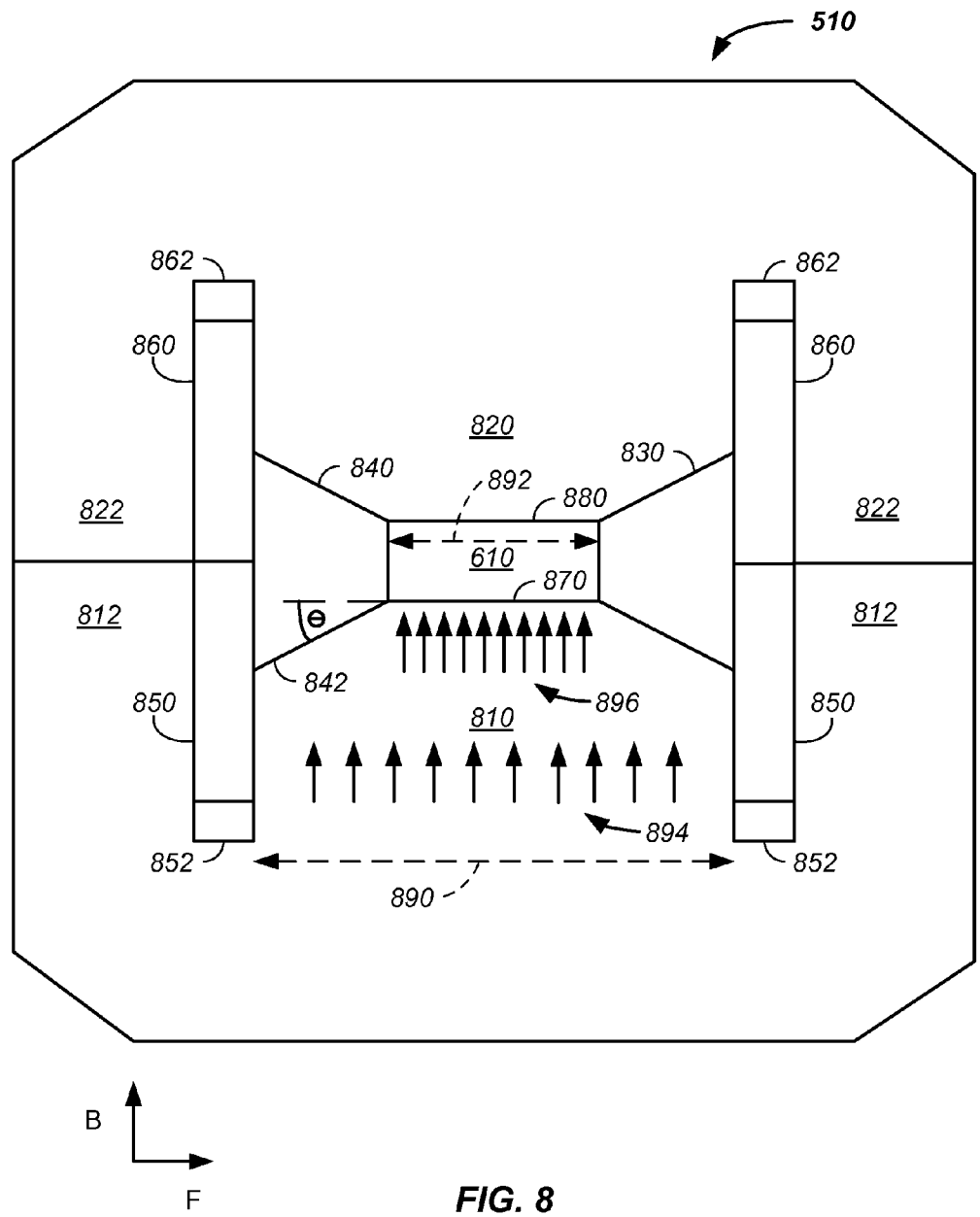
FIG. 8 illustrates a cross-sectional view of a bending magnet.

Referring now to FIGS. 7 and 8, two illustrative 90 degree rotated cross-sections of single magnet bending or turning sections 510 are presented. Referring now to FIG. 8, the magnet assembly has a first magnet 810 and a second magnet 820. A magnetic field induced by coils, described infra, runs between the first magnet 810 to the second magnet 820 across the gap 610. Return magnetic fields run through a first yoke 812 and second yoke 822. The combined cross-section area of the return yokes roughly approximates the cross-sectional area of the first magnet 810 or second magnet 820. The charged particles run through the vacuum tube in the gap 610. As illustrated, protons run into FIG. 8 through the gap 610 and the magnetic field, illustrated as vector B, applies a force F to the protons pushing the protons towards the center of the synchrotron, which is off page to the right in FIG. 8. The magnetic field is created using windings. A first coil makes up a first winding coil 850 and a second coil of wire makes up a second winding coil 860. Isolating or concentrating gaps 830, 840, such as air gaps, isolate the iron based yokes from the gap 610. The gap 610 is approximately flat to yield a uniform magnetic field across the gap 610, as described supra.

Still again to FIG. 7, the ends of a single bending or turning magnet are preferably beveled. Nearly perpendicular or right angle edges of a turning magnet 510 are represented by dashed lines 774, 784. The dashed lines 774, 784 intersect at a point 790 beyond the center of the synchrotron 280.

Preferably, the edge of the turning magnet is beveled at angles alpha, α, and beta, β, which are angles formed by a first line 772, 782 going from an edge of the turning magnet 510 and the center 280 and a second line 774, 784 going from the same edge of the turning magnet and the intersecting point 790. The angle alpha is used to describe the effect and the description of angle alpha applies to angle beta, but angle alpha is optionally different from angle beta. The angle alpha provides an edge focusing effect. Beveling the edge of the turning magnet 510 at angle alpha focuses the proton beam.

Multiple turning magnets provide multiple magnet edges that each have edge focusing effects in the synchrotron 130. If only one turning magnet is used, then the beam is only focused once for angle alpha or twice for angle alpha and angle beta. However, by using smaller turning magnets, more turning magnets fit into the turning sections 420 of the synchrotron 130. For example, if four magnets are used in a turning section 420 of the synchrotron, then for a single turning section there are eight possible edge focusing effect surfaces, two edges per magnet. The eight focusing surfaces yield a smaller cross-sectional beam size. This allows the use of a smaller gap 610.

The use of multiple edge focusing effects in the turning magnets results in not only a smaller gap 610, but also the use of smaller magnets and smaller power supplies. For a synchrotron 130 having four turning sections 420 where each turning sections has four turning magnets and each turning magnet has two focusing edges, a total of thirty-two focusing edges exist for each orbit of the protons in the circulating path of the synchrotron 130. Similarly, if 2, 6, or 8 magnets are used in a given turning section, or if 2, 3, 5, or 6 turning sections are used, then the number of edge focusing surfaces expands or contracts according to equation 2.

$$TFE = NTS * \frac{M}{NTS} * \frac{FE}{M} \qquad \text{eq. 2}$$

where TFE is the number of total focusing edges, NTS is the number of turning sections, M is the number of magnets, and FE is the number of focusing edges. Naturally, not all magnets are necessarily beveled and some magnets are optionally beveled on only one edge.

The inventors have determined that multiple smaller magnets have benefits over fewer larger magnets. For example, the use of 16 small magnets yields 32 focusing edges whereas the use of 4 larger magnets yields only 8 focusing edges. The use of a synchrotron having more focusing edges results in a circulating path of the synchrotron built without the use of focusing quadrupoles magnets. All prior art synchrotrons use quadrupoles in the circulating path of the synchrotron. Further, the use of quadrupoles in the circulating path necessitates additional straight sections in the circulating path of the synchrotron. Thus, the use of quadrupoles in the circulating path of a synchrotron results in synchrotrons having larger diameters, circulating beam pathlengths, and/or larger circumferences.

In various embodiments of the system described herein, the synchrotron has any combination of:
- at least 4 and preferably 6, 8, 10, or more edge focusing edges per 90 degrees of turn of the charged particle beam in a synchrotron having four turning sections;
- at least about 16 and preferably about 24, 32, or more edge focusing edges per orbit of the charged particle beam in the synchrotron;
- only 4 turning sections where each of the turning sections includes at least 4 and preferably 8 edge focusing edges;
- an equal number of straight sections and turning sections;
- exactly 4 turning sections;
- at least 4 edge focusing edges per turning section;
- no quadrupoles in the circulating path of the synchrotron;
- a rounded corner rectangular polygon configuration;
- a circumference of less than 60 meters;
- a circumference of less than 60 meters and 32 edge focusing surfaces; and/or
- any of about 8, 16, 24, or 32 non-quadrupole magnets per circulating path of the synchrotron, where the non-quadrupole magnets include edge focusing edges.

Referring again to FIG. 8, the incident magnetic field surface 870 of the first magnet 810 is further described. FIG. 8 is not to scale and is illustrative in nature. Local imperfections or unevenness in quality of the finish of the incident surface 870 results in inhomogeneities or imperfections in the magnetic field applied to the gap 610. Preferably, the incident surface 870 is flat, such as to within about a zero to three micron finish polish, or less preferably to about a ten micron finish polish.

Referring still to FIG. 8, additional magnet elements are described. The first magnet 810 preferably contains an initial cross sectional distance 890 of the iron based core. The contours of the magnetic field are shaped by the magnets 810, 820 and the yokes 812, 822. The iron based core tapers to a second cross sectional distance 892. The magnetic field in the magnet preferentially stays in the iron based core as opposed to the gaps 830, 840. As the cross-sectional distance decreases from the initial cross sectional distance 890 to the final cross-sectional distance 892, the magnetic field concentrates. The change in shape of the magnet from the longer distance 890 to the smaller distance 892 acts as an amplifier. The concentration of the magnetic field is illustrated by representing an initial density of magnetic field vectors 894 in the initial cross section 890 to a concentrated density of magnetic field vectors 896 in the final cross section 892. The concentration of the magnetic field due to the geometry of the turning magnets results in fewer winding coils 850, 860 being required and also a smaller power supply to the coils being required.

In one example, the initial cross-section distance 890 is about fifteen centimeters and the final cross-section distance 892 is about ten centimeters. Using the provided numbers, the concentration of the magnetic field is about 15/10 or 1.5 times at the incident surface 870 of the gap 610, though the relationship is not linear. The taper 842 has a slope, such as about 20, 40, or 60 degrees. The concentration of the magnetic field, such as by 1.5 times, leads to a corresponding decrease in power consumption requirements to the magnets.

Referring still to FIG. 8, the first magnet 810 preferably contains an initial cross sectional distance 890 of the iron based core. The contours of the magnetic field are shaped by the magnets 810, 820 and the yokes 812, 822. In this example, the core tapers to a second cross sectional distance 892 with a smaller angle theta, $\theta$. As described, supra, the magnetic field in the magnet preferentially stays in the iron based core as opposed to the gaps 830, 840. As the cross-sectional distance decreases from the initial cross sectional distance 890 to the final cross-sectional distance 892, the magnetic field concentrates. The smaller angle, theta, results in a greater amplification of the magnetic field in going from the longer distance 890 to the smaller distance 892. The concentration of the magnetic field is illustrated by representing an initial density of magnetic field vectors 894 in the initial cross section 890 to a concentrated density of magnetic field vectors 896 in the final cross section 892. The concentration of the magnetic field due to the geometry of the turning magnets results in fewer winding coils 850, 860 being required and also a smaller power supply to the winding coils 850, 860 being required.

Still referring to FIG. 8, optional correction coils 852, 862 are illustrated that are used to correct the strength of one or more turning magnets. The correction coils 852, 862 supplement the winding coils 850, 860. The correction coils 852, 862 have correction coil power supplies that are separate from winding coil power supplies used with the winding coils 850, 860. The correction coil power supplies typically operate at a fraction of the power required compared to the winding coil power supplies, such as about 1, 2, 3, 5, 7, or 10 percent of the power and more preferably about 1 or 2 percent of the power used with the winding coils 850, 860. The smaller operating power applied to the correction coils 852, 862 allows for more accurate and/or precise control of the correction coils. Correction coils are used to adjust for imperfection in the turning magnets 510, 520, 530, 540. Optionally, separate correction coils are used for each turning magnet allowing individual tuning of the magnetic field for each turning magnet, which eases quality requirements in the manufacture of each turning magnet.

Figure 9:
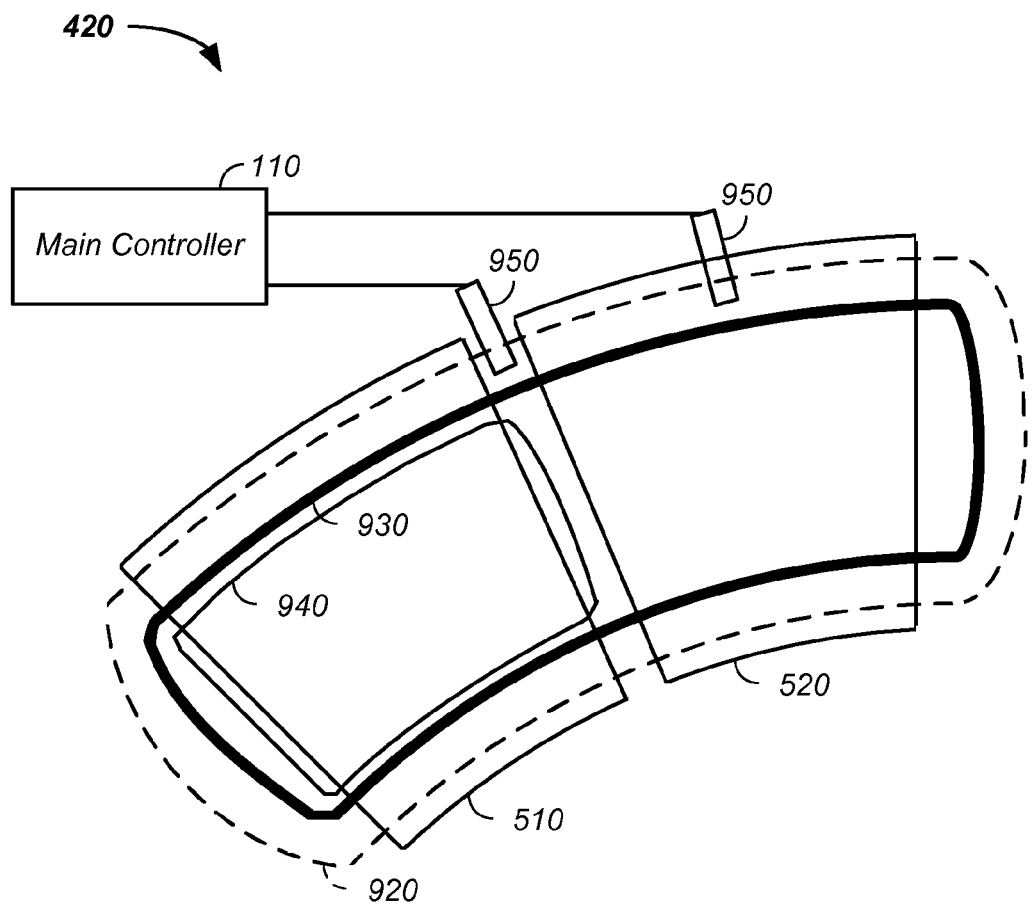
FIG. 9 illustrates a magnetic turning section of a synchrotron.

Referring now to FIG. 9, an example of winding coils and correction coils about a plurality of turning magnets 510, 520, 530, 540 in an ion beam turning section 420 is illustrated. One or more high precision magnetic field sensors are placed into the synchrotron and are used to measure the magnetic field at or near the proton beam path. For example, the magnetic sensors 950 are optionally placed between turning magnets and/or within a turning magnet, such as at or near the gap 610 or at or near the magnet core or yoke. The sensors are part of a feedback system to the correction coils. Thus, the system preferably stabilizes the magnetic field in the synchrotron elements rather that stabilizing the current applied to the magnets. Stabilization of the magnetic field allows the synchrotron to come to a new energy level quickly. This allows the system to be controlled to an operator or algorithm selected energy level with each pulse of the synchrotron and/or with each breath of the patient.

The winding and/or correction coils correct 1, 2, 3, or 4 turning magnets, and preferably correct a magnetic field generated by two turning magnets. A winding or correction coil covering multiple magnets reduces space between magnets as fewer winding or correction coil ends are required, which occupy space.

Figure 10A:
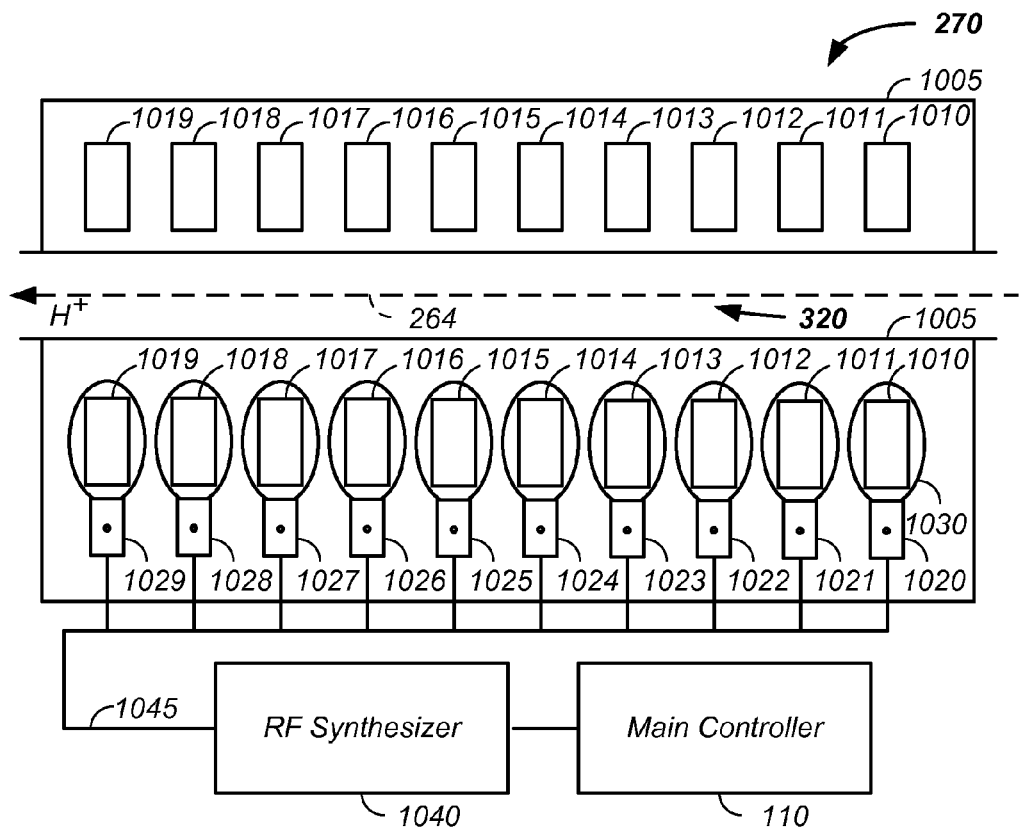
FIGS. 10A and B illustrate an RF accelerator and an RF accelerator subsystem, respectively.
Figure 10B:
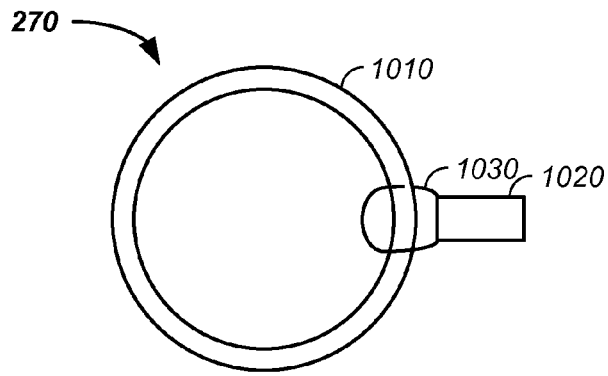

Referring now to FIG. 10A and FIG. 10B, the accelerator system 270, such as a radio-frequency (RF) accelerator system, is further described. The accelerator includes a series of coils 1010-1019, such as iron or ferrite coils, each circumferentially enclosing the vacuum system 320 through which the proton beam 264 passes in the synchrotron 130. Referring now to FIG. 10B, the first coil 1010 is further described. A loop of standard wire 1030 completes at least one turn about the first coil 1010. The loop attaches to a microcircuit 1020. Referring again to FIG. 10A, an RF synthesizer 1040, which is preferably connected to the main controller 110, provides a low voltage RF signal that is synchronized to the period of circulation of protons in the proton beam path 264. The RF synthesizer 1040, microcircuit 1020, loop 1030, and coil 1010 combine to provide an accelerating voltage to the protons in the proton beam path 264. For example, the RF synthesizer 1040 sends a signal to the microcircuit 1020, which amplifies the low voltage RF signal and yields an acceleration voltage, such as about 10 volts. The actual acceleration voltage for a single microcircuit/loop/coil combination is about 5, 10, 15, or 20 volts, but is preferably about 10 volts. Preferably, the RF-amplifier microcircuit and accelerating coil are integrated.

Still referring to FIG. 10A, the integrated RF-amplifier microcircuit and accelerating coil presented in FIG. 10B is repeated, as illustrated as the set of coils 1011-1019 surrounding the vacuum tube 320. For example, the RF-synthesizer 1040, under main controller 130 direction, sends an RF-signal to the microcircuits 1020-1029 connected to coils 1010-1019, respectively. Each of the microcircuit/loop/coil combinations generates a proton accelerating voltage, such as about 10 volts each. Hence, a set of five coil combinations generates about 50 volts for proton acceleration. Preferably about 5 to 20 microcircuit/loop/coil combinations are used and more preferably about 9 or 10 microcircuit/loop/coil combinations are used in the accelerator system 270.

As a further clarifying example, the RF synthesizer 1040 sends an RF-signal, with a period equal to a period of circulation of a proton about the synchrotron 130, to a set of ten microcircuit/loop/coil combinations, which results in about 100 volts for acceleration of the protons in the proton beam path 264. The 100 volts is generated at a range of frequencies, such as at about 1 MHz for a low energy proton beam, to about 15 MHz for a high energy proton beam. The RF-signal is optionally set at an integer multiple of a period of circulation of the proton about the synchrotron circulating path. Each of the microcircuit/loop/coil combinations are optionally independently controlled in terms of acceleration voltage and frequency.

Integration of the RF-amplifier microcircuit and accelerating coil, in each microcircuit/loop/coil combination, results in three considerable advantages. First, for synchrotrons, the prior art does not use microcircuits integrated with the accelerating coils but rather uses a set of long cables to provide power to a corresponding set of coils. The long cables have an impedance/resistance, which is problematic for high frequency RF control. As a result, the prior art system is not operable at high frequencies, such as above about 10 MHz. The integrated RF-amplifier microcircuit/accelerating coil system is operable at above about 10 MHz and even 15 MHz where the impedance and/or resistance of the long cables in the prior art systems results in poor control or failure in proton acceleration. Second, the long cable system, operating at lower frequencies, costs about $50,000 and the integrated microcircuit system costs about $1000, which is 50 times less expensive. Third, the microcircuit/loop/coil combinations in conjunction with the RF-amplifier system results in a compact low power consumption design allowing production and use of a proton cancer therapy system is a small space, as described supra, and in a cost effective manner.

Figure 11:
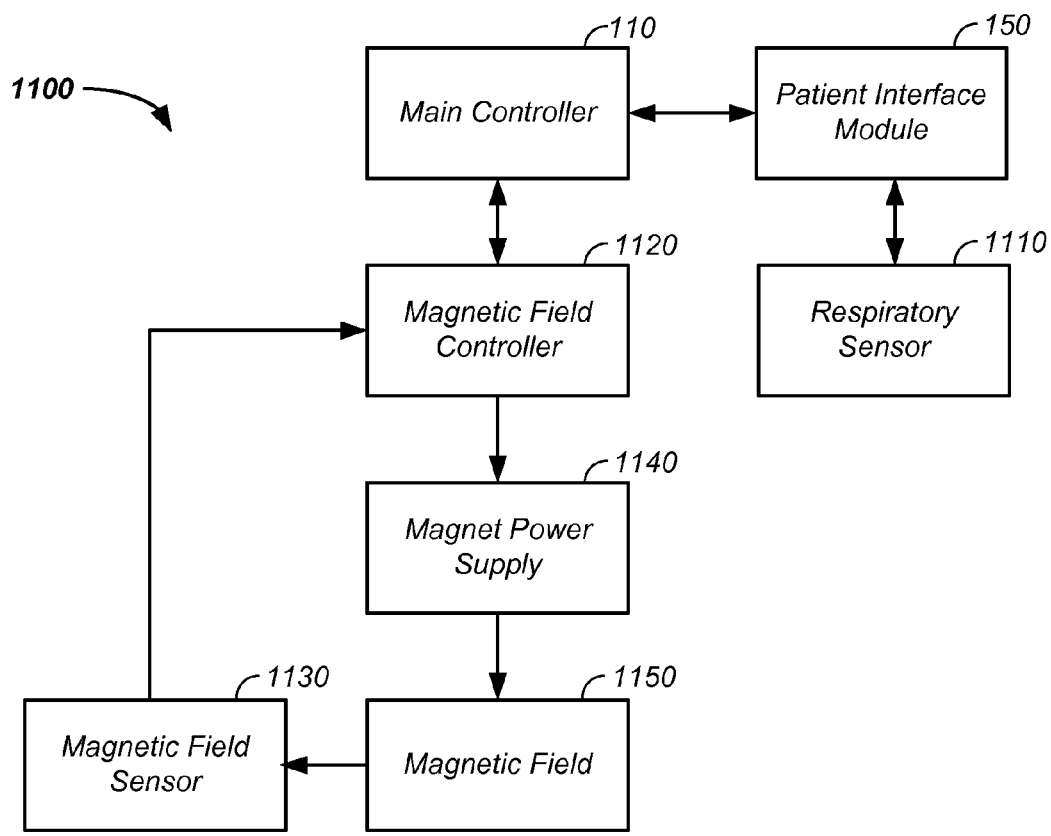
FIG. 11 illustrates a magnetic field control system.

Referring now to FIG. 11, an example is used to clarify the magnetic field control using a feedback loop 1100 to change delivery times and/or periods of proton pulse delivery. In one case, a respiratory sensor 1110 senses the breathing cycle of the subject. The respiratory sensor sends the information to an algorithm in a magnetic field controller 1120, typically via the patient interface module 150 and/or via the main controller 110 or a subcomponent thereof. The algorithm predicts and/or measures when the subject is at a particular point in the breathing cycle, such as at the bottom of a breath. Magnetic field sensors 1130 are used as input to the magnetic field controller, which controls a magnet power supply 1140 for a given magnetic field 1150, such as within a first turning magnet 510 of a synchrotron 130. The control feedback loop is thus used to dial the synchrotron to a selected energy level and deliver protons with the desired energy at a selected point in time, such as at the bottom of the breath. More particularly, the main controller injects protons into the synchrotron and accelerates the protons in a manner that combined with extraction delivers the protons to the tumor at a selected point in the breathing cycle. Intensity of the proton beam is also selectable and controllable by the main controller at this stage. The feedback control to the correction coils allows rapid selection of energy levels of the synchrotron that are tied to the patient's breathing cycle. This system is in stark contrast to a system where the current is stabilized and the synchrotron deliver pulses with a period, such as 10 or 20 cycles per second with a fixed period. Optionally, the feedback or the magnetic field design coupled with the correction coils allows for the extraction cycle to match the varying respiratory rate of the patient.

Traditional extraction systems do not allow this control as magnets have memories in terms of both magnitude and amplitude of a sine wave. Hence, in a traditional system, in order to change frequency, slow changes in current must be used. However, with the use of the feedback loop using the magnetic field sensors, the frequency and energy level of the synchrotron are rapidly adjustable. Further aiding this process is the use of a novel extraction system that allows for acceleration of the protons during the extraction process, described infra.

EXAMPLE III

Referring again to FIG. 9, an example of a winding coil 930 that covers two turning magnets 510, 520 is provided. Optionally, a first winding coil 940 covers one magnets or a second winding coil 920 covers a plurality of magnets 510, 520. As described, supra, this system reduces space between turning section allowing more magnetic field to be applied per radian of turn. A first correction coil 910 is illustrated that is used to correct the magnetic field for the first turning magnet 510. A second correction coil 920 is illustrated that is used to correct the magnetic field for a winding coil 930 about two turning magnets. Individual correction coils for each turning magnet are preferred and individual correction coils yield the most precise and/or accurate magnetic field in each turning section. Particularly, the individual correction coil 910 is used to compensate for imperfections in the individual magnet of a given turning section. Hence, with a series of magnetic field sensors, corresponding magnetic fields are individually adjustable in a series of feedback loops, via a magnetic field monitoring system, as an independent coil is used for each turning section. Alternatively, a multiple magnet correction coil is used to correct the magnetic field for a plurality of turning section magnets.

Flat Gap Surface

While the gap surface is described in terms of the first turning magnet 510, the discussion applies to each of the turning magnets in the synchrotron. Similarly, while the gap 610 surface is described in terms of the magnetic field incident surface 670, the discussion additionally optionally applies to the magnetic field exiting surface 680.

The magnetic field incident surface 870 of the first magnet 810 is preferably about flat, such as to within about a zero to three micron finish polish or less preferably to about a ten micron finish polish. By being very flat, the polished surface spreads the unevenness of the applied magnetic field across the gap 610. The very flat surface, such as about 0, 1, 2, 4, 6, 8, 10, 15, or 20 micron finish, allows for a smaller gap size, a smaller applied magnetic field, smaller power supplies, and tighter control of the proton beam cross-sectional area. The magnetic field exiting surface 880 is also preferably flat.

Proton Beam Extraction

Figure 12:
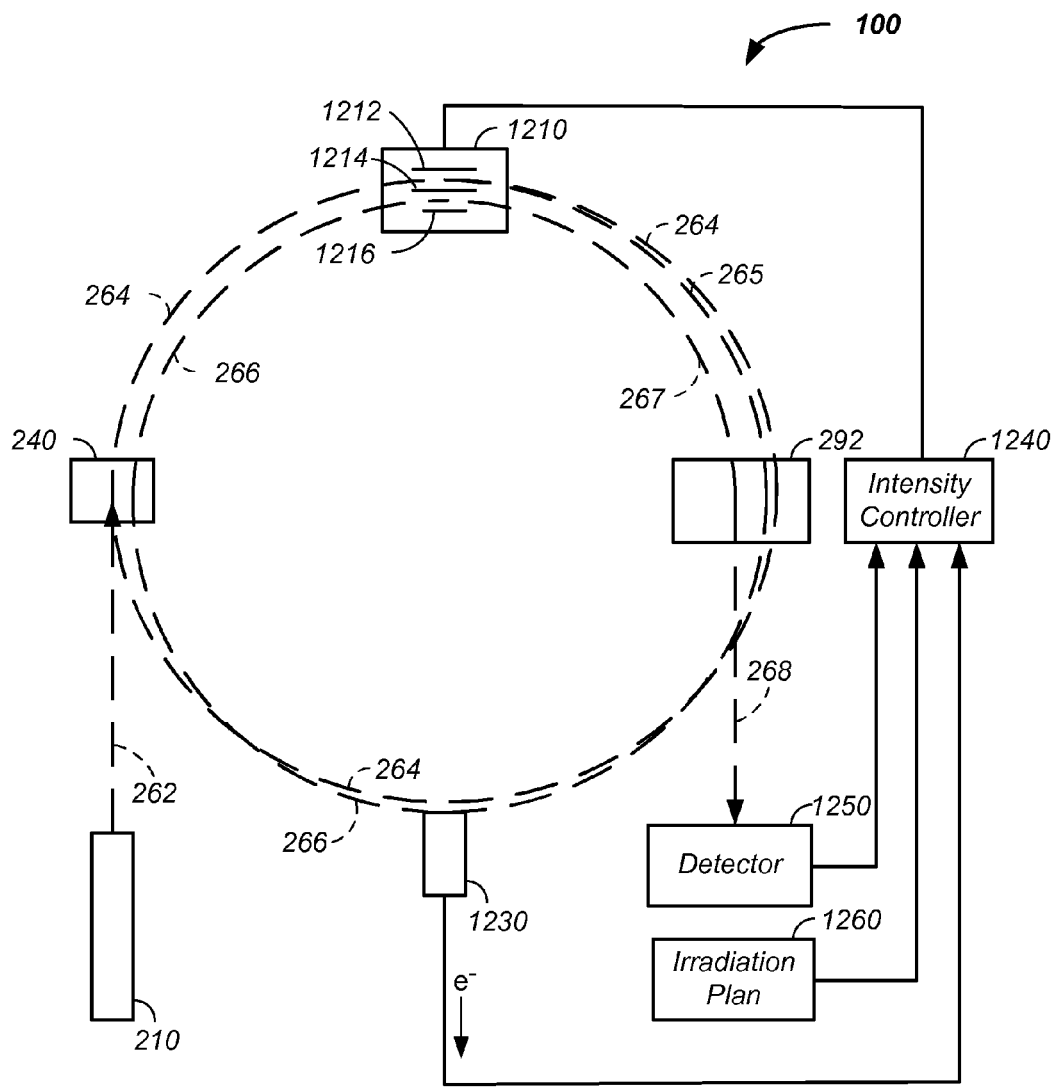
FIG. 12 illustrates a charged particle extraction and intensity control system.

Referring now to FIG. 12, an exemplary proton extraction process from the synchrotron 130 is illustrated. For clarity, FIG. 12 removes elements represented in FIG. 2, such as the turning magnets, which allows for greater clarity of presentation of the proton beam path as a function of time. Generally, protons are extracted from the synchrotron 130 by slowing the protons. As described, supra, the protons were initially accelerated in a circulating path 264, which is maintained with a plurality of main bending magnets 250. The circulating path is referred to herein as an original central beamline 264. The protons repeatedly cycle around a central point in the synchrotron 280. The proton path traverses through a radio frequency (RF) cavity system 1210. To initiate extraction, an RF field is applied across a first blade 1212 and a second blade 1214, in the RF cavity system 1210. The first blade 1212 and second blade 1214 are referred to herein as a first pair of blades.

In the proton extraction process; an RF voltage is applied across the first pair of blades, where the first blade 1212 of the first pair of blades is on one side of the circulating proton beam path 264 and the second blade 1214 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265. Upon a second pass of the protons through the RF cavity system, the RF field further moves the protons off of the original proton beamline 264. For example, if the original beamline is considered as a circular path, then the altered beamline is slightly elliptical. The applied RF field is timed to apply outward or inward movement to a given band of protons circulating in the synchrotron accelerator. Each orbit of the protons is slightly more off axis compared to the original circulating beam path 264. Successive passes of the protons through the RF cavity system are forced further and further from the original central beamline 264 by altering the direction and/or intensity of the RF field with each successive pass of the proton beam through the RF field.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons.

The process of timing the RF field to a given proton beam within the RF cavity system is repeated thousands of times with each successive pass of the protons being moved approximately one micrometer further off of the original central beamline 264. For clarity, the approximately 1000 changing beam paths with each successive path of a given band of protons through the RF field are illustrated as the altered beam path 265.

With a sufficient sine wave betatron amplitude, the altered circulating beam path 265 touches a material 1230, such as a foil or a sheet of foil. The foil is preferably a lightweight material, such as beryllium, a lithium hydride, a carbon sheet, or a material of low nuclear charge. A material of low nuclear charge is a material composed of atoms consisting essentially of atoms having six or fewer protons. The foil is preferably about 10 to 150 microns thick, is more preferably 30 to 100 microns thick, and is still more preferably 40-60 microns thick. In one example, the foil is beryllium with a thickness of about 50 microns. When the protons traverse through the foil, energy of the protons is lost and the speed of the protons is reduced. Typically, a current is also generated, described infra. Protons moving at a slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the material 1230 is optionally adjusted to created a change in the radius of curvature, such as about ½, 1, 2, 3, or 4 mm less than the last pass of the protons 265 or original radius of curvature 264. Protons moving with the smaller radius of curvature travel between a second pair of blades. In one case, the second pair of blades is physically distinct and/or are separated from the first pair of blades. In a second case, one of the first pair of blades is also a member of the second pair of blades. For example, the second pair of blades is the second blade 1214 and a third blade 1216 in the RF cavity system 1210. A high voltage DC signal, such as about 1 to 5 kV, is then applied across the second pair of blades, which directs the protons out of the synchrotron through an extraction magnet 292, such as a Lamberson extraction magnet, into a transport path 268.

Control of acceleration of the charged particle beam path in the synchrotron with the accelerator and/or applied fields of the turning magnets in combination with the above described extraction system allows for control of the intensity of the extracted proton beam, where intensity is a proton flux per unit time or the number of protons extracted as a function of time. For example, when a current is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

Because the extraction system does not depend on any change in magnetic field properties, it allows the synchrotron to continue to operate in acceleration or deceleration mode during the extraction process. Stated differently, the extraction process does not interfere with synchrotron acceleration.

In stark contrast, traditional extraction systems introduce a new magnetic field, such as via a hexapole, during the extraction process. More particularly, traditional synchrotrons have a magnet, such as a hexapole magnet, that is off during an acceleration stage. During the extraction phase, the hexapole magnetic field is introduced to the circulating path of the synchrotron. The introduction of the magnetic field necessitates two distinct modes, an acceleration mode and an extraction mode, which are mutually exclusive in time.

Charged Particle Beam Intensity Control

Control of applied field, such as a radio-frequency (RF) field, frequency and magnitude in the RF cavity system 1210 allows for intensity control of the extracted proton beam, where intensity is extracted proton flux per unit time or the number of protons extracted as a function of time.

Referring still to FIG. 12, when protons in the proton beam hit the material 1230 electrons are given off resulting in a current. The resulting current is converted to a voltage and is used as part of a ion beam intensity monitoring system or as part of an ion beam feedback loop for controlling beam intensity. The voltage is optionally measured and sent to the main controller 110 or to a controller subsystem. More particularly, when protons in the charged particle beam path pass through the material 1230, some of the protons lose a small fraction of their energy, such as about one-tenth of a percent, which results in a secondary electron. That is, protons in the charged particle beam push some electrons when passing through material 1230 giving the electrons enough energy to cause secondary emission. The resulting electron flow results in a current or signal that is proportional to the number of protons going through the target material 1230. The resulting current is preferably converted to voltage and amplified. The resulting signal is referred to as a measured intensity signal.

The amplified signal or measured intensity signal resulting from the protons passing through the material 1230 is preferably used in controlling the intensity of the extracted protons. For example, the measured intensity signal is compared to a goal signal, which is predetermined in an irradiation of the tumor plan 1260. In one example, the tumor plan 1260 contains the goal or targeted energy and intensity of the delivered proton beam as a function of x-position, y-position, time, and/or rotational position of the patient. The difference between the measured intensity signal and the planned for goal signal is calculated. The difference is used as a control to the RF generator. Hence, the measured flow of current resulting from the protons passing through the material 1230 is used as a control in the RF generator to increase or decrease the number of protons undergoing betatron oscillation and striking the material 1230. Hence, the voltage determined off of the material 1230 is used as a measure of the orbital path and is used as a feedback control to control the RF cavity system. Alternatively, the measured intensity signal is not used in the feedback control and is just used as a monitor of the intensity of the extracted protons.

As described, supra, the photons striking the material 1230 is a step in the extraction of the protons from the synchrotron 130. Hence, the measured intensity signal is used to change the number of protons per unit time being extracted, which is referred to as intensity of the proton beam. The intensity of the proton beam is thus under algorithm control. Further, the intensity of the proton beam is controlled separately from the velocity of the protons in the synchrotron 130. Hence, intensity of the protons extracted and the energy of the protons extracted are independently variable.

For example, protons initially move at an equilibrium trajectory in the synchrotron 130. An RF field is used to excite the protons into a betatron oscillation. In one case, the frequency of the protons orbit is about 10 MHz. In one example, in about one millisecond or after about 10,000 orbits, the first protons hit an outer edge of the target material 130. The specific frequency is dependent upon the period of the orbit. Upon hitting the material 130, the protons push electrons through the foil to produce a current. The current is converted to voltage and amplified to yield a measured intensity signal. The measured intensity signal is used as a feedback input to control the applied RF magnitude, RF frequency, or RF field. Preferably, the measured intensity signal is compared to a target signal and a measure of the difference between the measured intensity signal and target signal is used to adjust the applied RF field in the RF cavity system 1210 in the extraction system to control the intensity of the protons in the extraction step. Stated again, the signal resulting from the protons striking and/or passing through the material 130 is used as an input in RF field modulation. An increase in the magnitude of the RF modulation results in protons hitting the foil or material 130 sooner. By increasing the RF, more protons are pushed into the foil, which results in an increased intensity, or more protons per unit time, of protons extracted from the synchrotron 130.

In another example, a detector 1250 external to the synchrotron 130 is used to determine the flux of protons extracted from the synchrotron and a signal from the external detector is used to alter the RF field or RF modulation in the RF cavity system 1210. Here the external detector generates an external signal, which is used in a manner similar to the measured intensity signal, described in the preceding paragraphs. Particularly, the measured intensity signal is compared to a desired signal from the irradiation plan 1260 in a feedback intensity controller 1240, which adjusts the RF field between the first plate 1212 and the second plate 1214 in the extraction process, described supra.

In yet another example, when a current from material 130 resulting from protons passing through or hitting material is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In still yet another embodiment, intensity modulation of the extracted proton beam is controlled by the main controller 110. The main controller 110 optionally and/or additionally controls timing of extraction of the charged particle beam and energy of the extracted proton beam.

The benefits of the system include a multi-dimensional scanning system. Particularly, the system allows independence in: (1) energy of the protons extracted and (2) intensity of the protons extracted. That is, energy of the protons extracted is controlled by an energy control system and an intensity control system controls the intensity of the extracted protons. The energy control system and intensity control system are optionally independently controlled. Preferably, the main controller 110 controls the energy control system and the main controller simultaneously controls the intensity control system to yield an extracted proton beam with controlled energy and controlled intensity where the controlled energy and controlled intensity are independently variable. Thus the irradiation spot hitting the tumor is under independent control of:

time;
    energy;
    intensity;
    x-axis position, where the x-axis represents horizontal movement of the proton beam relative to the patient, and y-axis position, where the y-axis represents vertical movement of the proton beam relative to the patient.

In addition, the patient is optionally independently rotated relative to a translational axis of the proton beam at the same time. The system is capable of pulse-to-pulse energy variability. Additionally, the system is capable of dynamic energy modulation during a pulse, enabling true three-dimensional proton beam scanning with energy and/or intensity modulation.

Figure 13A:
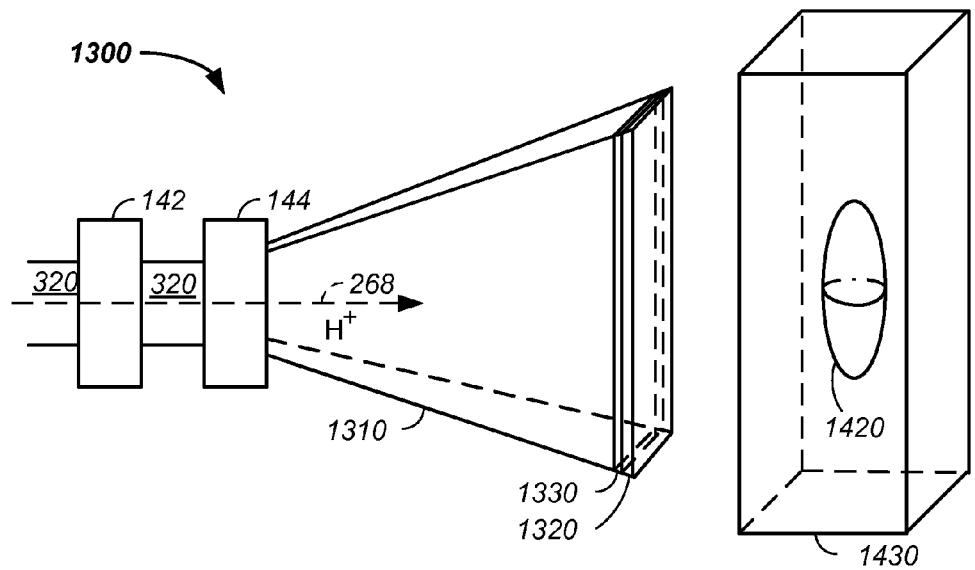
FIG. 13 illustrates a proton beam position verification system.
Figure 13B:
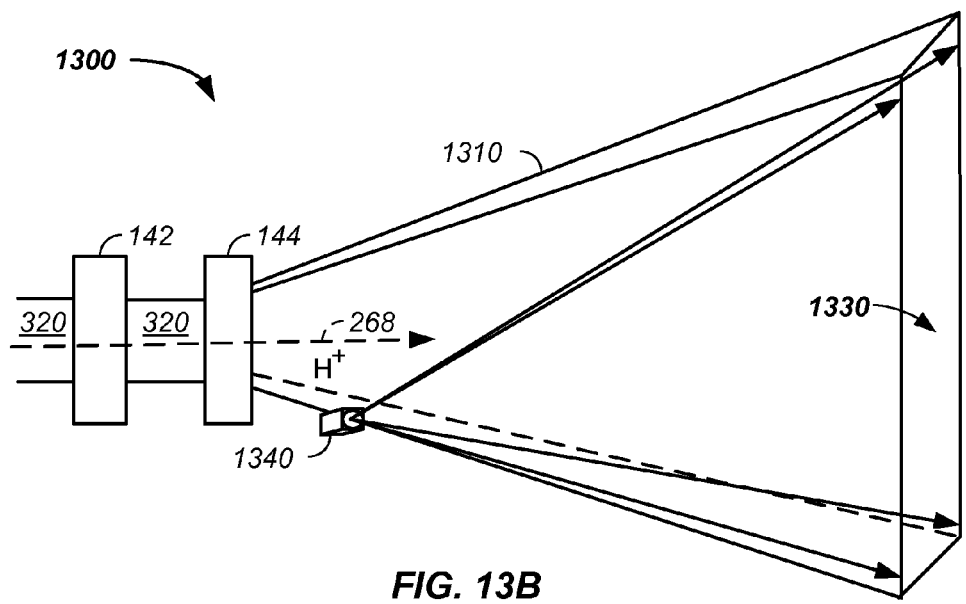

Referring now to FIG. 13, a proton beam position verification system 1300 is described. A nozzle 1310 provides an outlet for the second reduced pressure vacuum system initiating at the foil 395 of the tandem accelerator 390 and running through the synchrotron 130 to a nozzle foil 1320 covering the end of the nozzle 1310. The nozzle expands in cross-sectional area along the z-axis of the proton beam path 268 to allow the proton beam 268 to be scanned along the x- and y-axes by the vertical control element 142 and horizontal control element 144, respectively. The nozzle foil 1320 is preferably mechanically supported by the outer edges of an exit port of the nozzle 1310. An example of a nozzle foil 1320 is a sheet of about 0.1 inch thick aluminum foil. Generally, the nozzle foil separates atmosphere pressures on the patient side of the nozzle foil 1320 from the low pressure region, such as about $10^{-5}$ to $10^{-7}$ torr region, on the synchrotron 130 side of the nozzle foil 1320. The low pressure region is maintained to reduce scattering of the proton beam 264, 268.

Still referring to FIG. 13, the proton beam verification system 1300 is a system that allows for monitoring of the actual proton beam position 268, 269 in real-time without destruction of the proton beam. The proton beam verification system 1300 preferably includes a proton beam position verification layer 1330, which is also referred to herein as a coating, luminescent, fluorescent, phosphorescent, radiance, or viewing layer. The verification layer or coating layer 1330 is preferably a coating or thin layer substantially in contact with an inside surface of the nozzle foil 1320, where the inside surface is on the synchrotron side of the nozzle foil 1320. Less preferably, the verification layer or coating layer 1330 is substantially in contact with an outer surface of the nozzle foil 1320, where the outer surface is on the patient treatment side of the nozzle foil 1320. Preferably, the nozzle foil 1320 provides a substrate surface for coating by the coating layer, but optionally a separate coating layer support element, on which the coating 1330 is mounted, is placed anywhere in the proton beam path 268.

Still referring to FIG. 13, the coating 1330 yields a measurable spectroscopic response, spatially viewable by the detector 1340, as a result of transmission by the proton beam 268. The coating 1330 is preferably a phosphor, but is optionally any material that is viewable or imaged by a detector where the material changes spectroscopically as a result of the proton beam path 268 hitting or transmitting through the coating 1330. A detector or camera 1340 views the coating layer 1330 and determines the current position of the proton beam 268 by the spectroscopic differences resulting from protons passing through the coating layer. For example, the camera 1340 views the coating surface 1330 as the proton beam 268 is being scanned by the horizontal 144 and vertical 142 beam position control elements during treatment of the tumor 1420. The camera 1340 views the current position of the proton beam 268 as measured by spectroscopic response. The coating layer 1330 is preferably a phosphor or luminescent material that glows or emits photons for a short period of time, such as less than 5 seconds for a 50% intensity, as a result of excitation by the proton beam 268. Optionally, a plurality of cameras or detectors 1340 are used, where each detector views all or a portion of the coating layer 1330. For example, two detectors 1340 are used where a first detector views a first half of the coating layer and the second detector views a second half of the coating layer. Preferably, the detector 1340 is mounted into the nozzle 1310 to view the proton beam position after passing through the first axis and second axis controllers 142, 144. Preferably, the coating layer 1330 is positioned in the proton beam path 268 in a position prior to the protons striking the patient 1430.

Still referring to FIG. 13, the main controller 130, connected to the camera or detector 1340 output, compares the actual proton beam position 268 with the planned proton beam position and/or a calibration reference to determine if the actual proton beam position 268 is within tolerance. The proton beam verification system 1300 preferably is used in at least two phases, a calibration phase and a proton beam treatment phase. The calibration phase is used to correlate, as a function of x-, y-position of the glowing response the actual x-, y-position of the proton beam at the patient interface. During the proton beam treatment phase, the proton beam position is monitored and compared to the calibration and/or treatment plan to verify accurate proton delivery to the tumor 1420 and/or as a proton beam shutoff safety indicator.

Patient Positioning

Referring now to FIG. 14, the patient is preferably positioned on or within a patient positioning system 1410 of the patient interface module 150. The patient positioning system 1410 is used to translate the patient and/or rotate the patient into a zone where the proton beam can scan the tumor using a scanning system 140 or proton targeting system, described infra. Essentially, the patient positioning system 1410 performs large movements of the patient to place the tumor near the center of a proton beam path 268 and the proton scanning or targeting system 140 performs fine movements of the momentary beam position 269 in targeting the tumor 1420. To illustrate, FIG. 14 shows the momentary proton beam position 269 and a range of scannable positions 1440 using the proton scanning or targeting system 140, where the scannable positions 1440 are about the tumor 1420 of the patient 1430. In this example, the scannable positions are scanned along the x- and y-axes; however, scanning is optionally simultaneously performed along the z-axis as described infra. This illustratively shows that the y-axis movement of the patient occurs on a scale of the body, such as adjustment of about 1, 2, 3, or 4 feet, while the scannable region of the proton beam 268 covers a portion of the body, such as a region of about 1, 2, 4, 6, 8, 10, or 12 inches. The patient positioning system and its rotation and/or translation of the patient combines with the proton targeting system to yield precise and/or accurate delivery of the protons to the tumor.

Figure 14A:
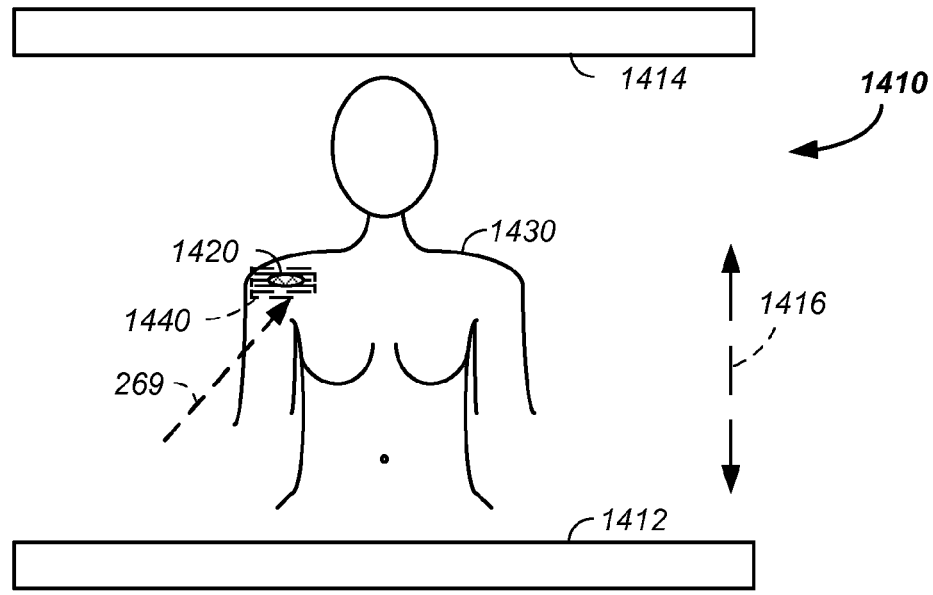
FIG. 14 illustrates a patient positioning system from: (A) a front view and (B) a top view.
Figure 14B:
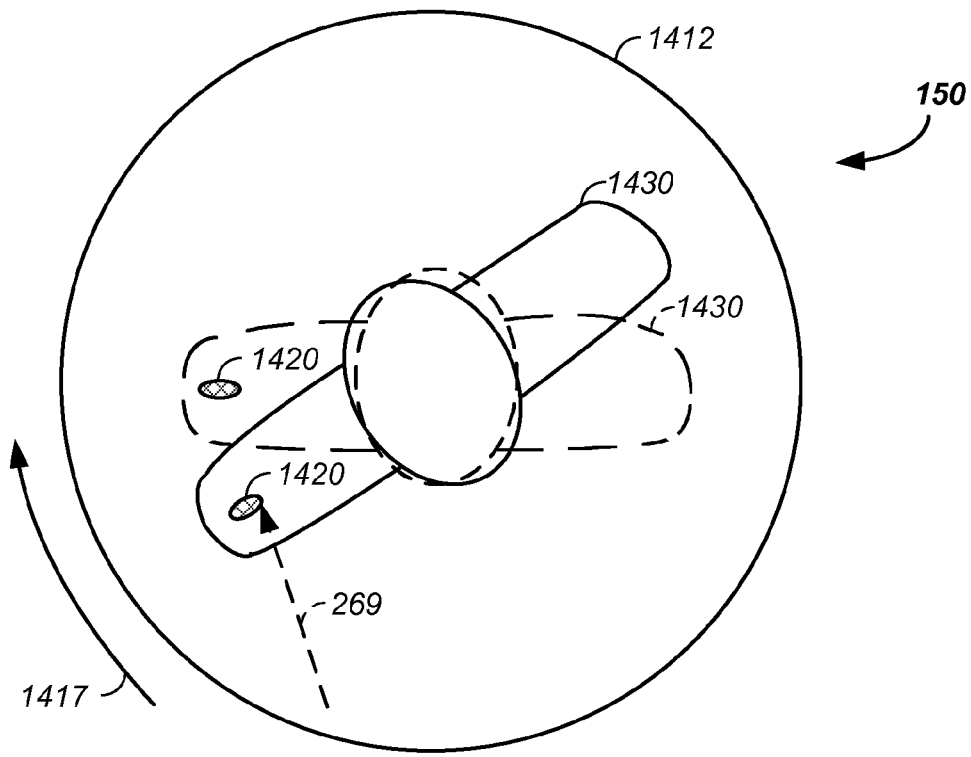

Referring still to FIG. 14, the patient positioning system 1410 optionally includes a bottom unit 1412 and a top unit 1414, such as discs or a platform. Referring now to FIG. 14A, the patient positioning unit 1410 is preferably y-axis adjustable 1416 to allow vertical shifting of the patient relative to the proton therapy beam 268. Preferably, the vertical motion of the patient positioning unit 1410 is about 10, 20, 30, or 50 centimeters per minute. Referring now to FIG. 14B, the patient positioning unit 1410 is also preferably rotatable 1417 about a rotation axis, such as about the y-axis running through the center of the bottom unit 1412 or about a y-axis running through the tumor 1420, to allow rotational control and positioning of the patient relative to the proton beam path 268. Preferably the rotational motion of the patient positioning unit 1410 is about 360 degrees per minute. Optionally, the patient positioning unit rotates about 45, 90, or 180 degrees. Optionally, the patient positioning unit 1410 rotates at a rate of about 45, 90, 180, 360, 720, or 1080 degrees per minute. The rotation of the positioning unit 1417 is illustrated about the rotation axis at two distinct times, $t_1$ and $t_2$. Protons are optionally delivered to the tumor 1420 at n times where each of the n times represent different directions of the incident proton beam 269 hitting the patient 1430 due to rotation of the patient 1417 about the rotation axis.

Any of the semi-vertical, sitting, or laying patient positioning embodiments described, infra, are optionally vertically translatable along the y-axis or rotatable about the rotation or y-axis.

Preferably, the top and bottom units 1412, 1414 move together, such that they rotate at the same rates and translate in position at the same rates. Optionally, the top and bottom units 1412, 1414 are independently adjustable along the y-axis to allow a difference in distance between the top and bottom units 1412, 1414. Motors, power supplies, and mechanical assemblies for moving the top and bottom units 1412, 1414 are preferably located out of the proton beam path 269, such as below the bottom unit 1412 and/or above the top unit 1414. This is preferable as the patient positioning unit 1410 is preferably rotatable about 360 degrees and the motors, power supplies, and mechanical assemblies interfere with the protons if positioned in the proton beam path 269.

Proton Delivery Efficiency

Figure 15:
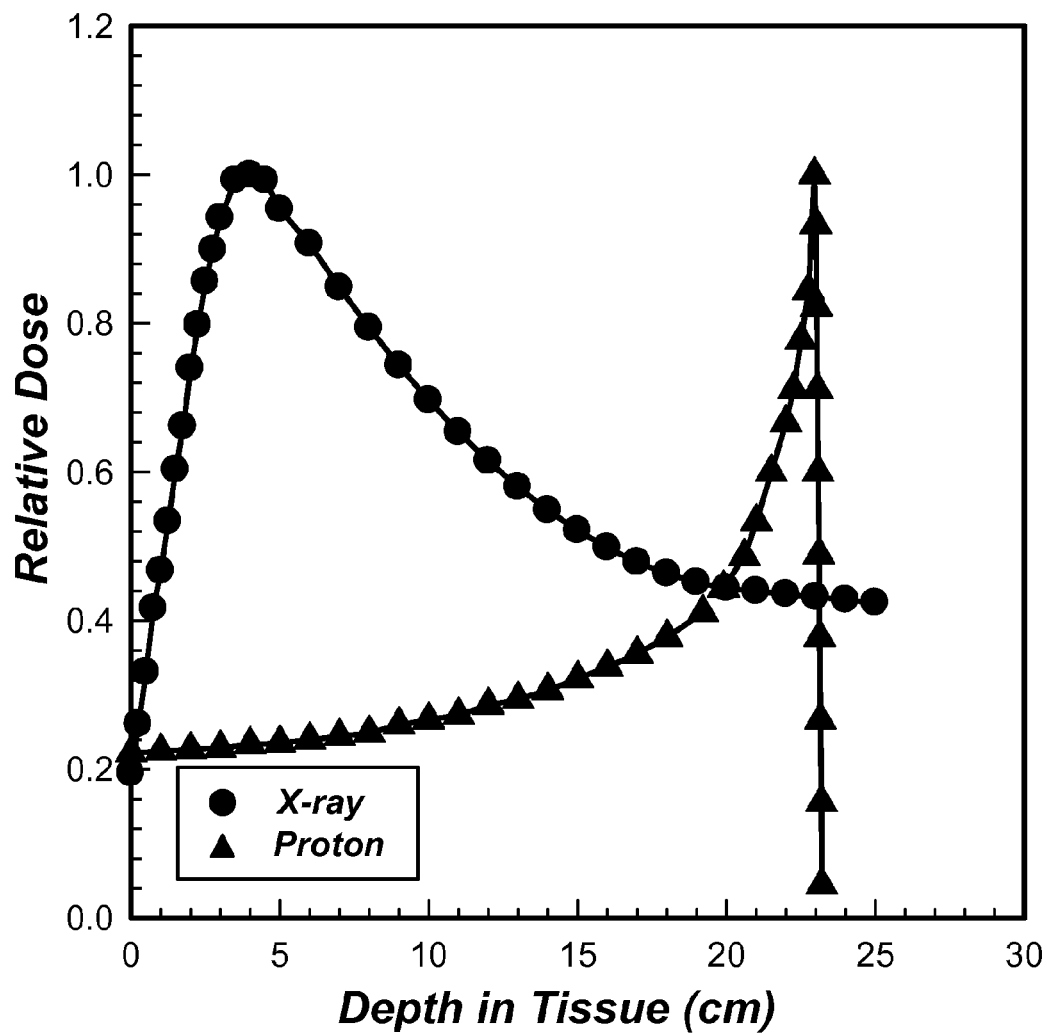
FIG. 15 provides X-ray and proton beam dose distributions.
Figure 16A:
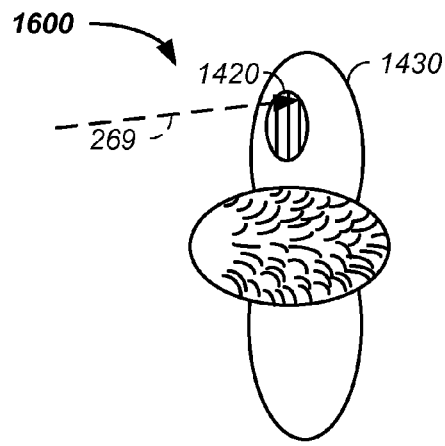
FIGS. 16 A-E illustrate controlled depth of focus irradiation.
Figure 16B:
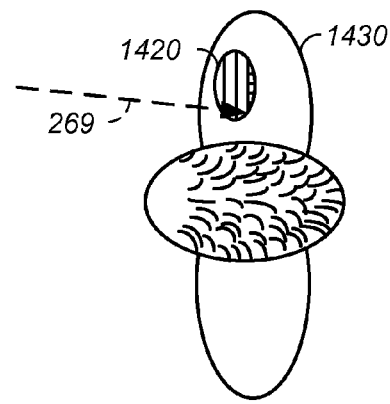
Figure 16C:
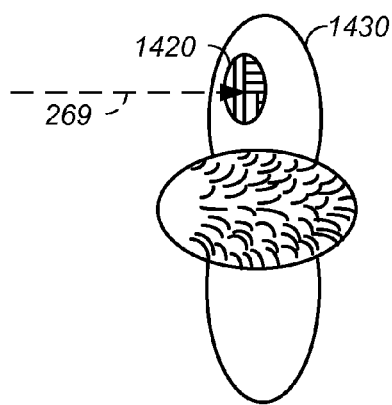
Figure 16D:
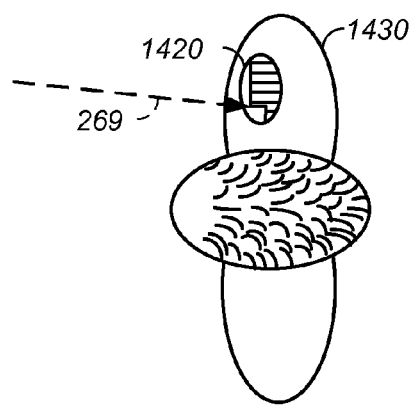
Figure 16E:
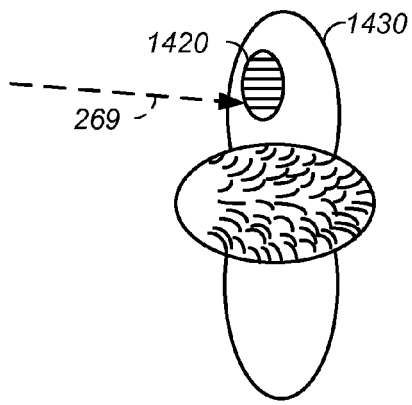
Figure 17A:
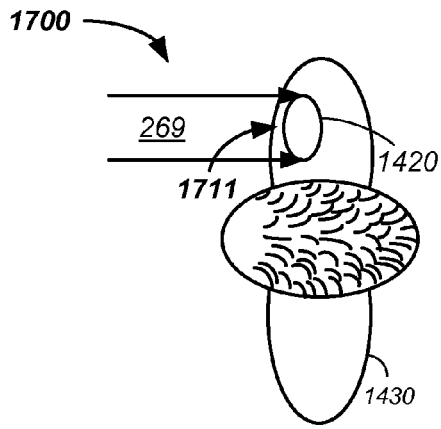
FIGS. 17 A-E illustrate multi-field irradiation.
Figure 17B:
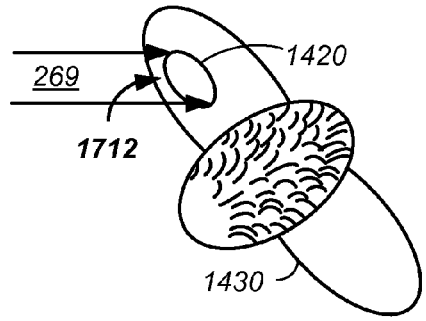
Figure 17C:
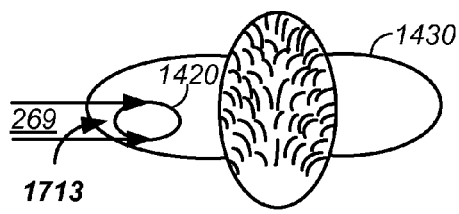
Figure 17D:
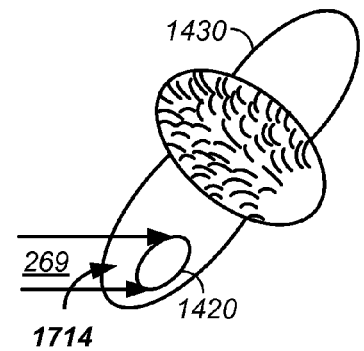
Figure 17E:
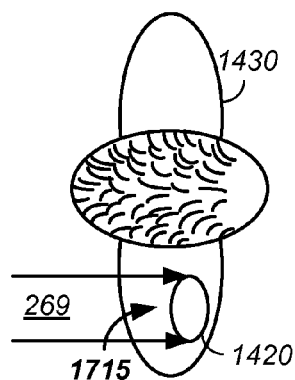

Referring now to FIG. 15, a common distribution of relative doses for both X-rays and proton irradiation is presented. As shown, X-rays deposit their highest dose near the surface of the targeted tissue and then exponentially decreases as a function of tissue depth. The deposition of X-ray energy near the surface is non-ideal for tumors located deep within the body, which is usually the case, as excessive damage is done to the soft tissue layers surrounding the tumor 1420.

The advantage of protons is that they deposit most of their energy near the end of the flight trajectory as the energy loss per unit path of the absorber transversed by a proton increases with decreasing particle velocity, giving rise to a sharp maximum in ionization near the end of the range, referred to herein as the Bragg peak. Furthermore, since the flight trajectory of the protons is variable by increasing or decreasing their initial kinetic energy or initial velocity, then the peak corresponding to maximum energy is movable within the tissue. Thus z-axis control of the proton depth of penetration is allowed by the acceleration/extraction process, described supra. As a result of the protons dose-distribution characteristics, a radiation oncologist can optimize dosage to the tumor 1420 while minimizing dosage to surrounding normal tissues.

The Bragg peak energy profile shows that protons deliver their energy across the entire length of the body penetrated by the proton up to a maximum penetration depth. As a result, energy is being delivered, in the ingress portion of the Bragg peak energy profile, to healthy tissue, bone, and other body constituents before the proton beam hits the distal or back side of the tumor. It follows that the shorter the pathlength in the body prior to the tumor, the higher the efficiency of proton delivery efficiency, where proton delivery efficiency is a measure of how much energy is delivered to the tumor relative to healthy portions of the patient. Examples of proton delivery efficiency include: (1) a ratio of proton energy delivered to the tumor over proton energy delivered to non-tumor tissue; (2) pathlength of protons in the tumor versus pathlength in the non-tumor tissue; and (3) damage to a tumor compared to damage to healthy body parts. Any of these measures are optionally weighted by damage to sensitive tissue, such as a nervous system element, heart, brain, or other organ. To illustrate, for a patient in a laying position where the patient is rotated about the y-axis during treatment, a tumor near the heart would at times be treated with protons running through the head-to-heart path, leg-to-heart path, or hip-to-heart path, which are all inefficient compared to a patient in a sitting or semi-vertical position where the protons are all delivered through a shorter chest-to-heart; side-of-body-to-heart, or back-to-heart path. Particularly, compared to a laying position, using a sitting or semi-vertical position of the patient, a shorter pathlength through the body to a tumor is provided to a tumor located in the torso or head, which results in a higher or better proton delivery efficiency.

Herein proton delivery efficiency is separately described from the time efficiency or synchrotron use efficiency, which is a fraction of time that the charged particle beam apparatus is in operation.

Depth Targeting

Referring now to FIGS. 16 A-E, x-axis scanning of the proton beam is illustrated while z-axis energy of the proton beam undergoes controlled variation 1600 to allow irradiation of slices of the tumor 1420. For clarity of presentation, the simultaneous y-axis scanning that is performed is not illustrated. In FIG. 16A, irradiation is commencing with the momentary proton beam position 269 at the start of a first slice. Referring now to FIG. 16B, the momentary proton beam position is at the end of the first slice. Importantly, during a given slice of irradiation, the proton beam energy is preferably continuously controlled and changed according to the tissue density in front of the tumor 1420. The variation of the proton beam energy to account for tissue density thus allows the beam stopping point, or Bragg peak, to remain inside the tissue slice. The variation of the proton beam energy during scanning is possible due to the acceleration/extraction techniques, described supra, which allow for acceleration of the proton beam during extraction. FIGS. 16C, 16D, and 16E show the momentary proton beam position in the middle of the second slice, two-thirds of the way through a third slice, and after finalizing irradiation from a given direction, respectively. Using this approach, controlled, accurate, and precise delivery of proton irradiation energy to the tumor 1420, to a designated tumor subsection, or to a tumor layer is achieved. Efficiency of deposition of proton energy to tumor, as defined as the ratio of the proton irradiation energy delivered to the tumor relative to the proton irradiation energy delivered to the healthy tissue is further described infra.

Multi-Field Irradiation

It is desirable to maximize efficiency of deposition of protons to the tumor 1420, as defined by maximizing the ratio of the proton irradiation energy delivered to the tumor 1420 relative to the proton irradiation energy delivered to the healthy tissue. Irradiation from one, two, or three directions into the body, such as by rotating the body about 90 degrees between irradiation sub-sessions results in proton irradiation from the ingress portion of the Bragg peak concentrating into one, two, or three healthy tissue volumes, respectively. It is desirable to further distribute the ingress portion of the Bragg peak energy evenly through the healthy volume tissue surrounding the tumor 1420.

Multi-field irradiation is proton beam irradiation from a plurality of entry points into the body. For example, the patient 1430 is rotated and the radiation source point is held constant. For example, as the patient 1430 is rotated through 360 degrees and proton therapy is applied from a multitude of angles resulting in the distal radiation being circumferentially spread in the tumor and ingress energy being distributed about the tumor yielding enhanced proton irradiation efficiency. In one case, the body is rotated into greater than 3, 5, 10, 15, 20, 25, 30, or 35 positions and proton irradiation occurs with each rotation position. Rotation of the patient for proton therapy or for X-ray imaging is preferably about 45, 90, 135, 180, 270, or 360 degrees. Rotation of the patient is preferably performed using the patient positioning system 1410 and/or the bottom unit 1412 or disc, described supra. Rotation of the patient 1430 while keeping the delivery proton beam 268 in a relatively fixed orientation allows irradiation of the tumor 1420 from multiple directions without use of a new collimator for each direction. Further, as no new setup is required for each rotation position of the patient 1430, the system allows the tumor 1420 to be treated from multiple directions without reseating or positioning the patient, thereby minimizing tumor 1420 regeneration time and increasing patient 1430 cancer therapy throughput.

The patient is optionally centered on the bottom unit 1412 or the tumor 1420 is optionally centered on the bottom unit 1412. If the patient is centered on the bottom unit 1412, then the first axis control element 142 and second axis control element 144 are programmed to compensate for the off central axis of rotation position variation of the tumor 1420.

Referring now to FIGS. 17 A-E, an example of multi-field irradiation 1700 is presented. In this example, five patient rotation positions are illustrated; however, the five rotation positions are discrete rotation positions of about thirty-six rotation positions, where the body is rotated about ten degrees with each position. Referring now to FIG. 17A, a range of irradiation beam positions 269 is illustrated from a first body rotation position, illustrated as the patient 1430 facing the proton irradiation beam where a first healthy volume 1711 is irradiated by the ingress portion of the Bragg peak energy irradiation profile. Referring now to FIG. 17B, the patient 1430 is rotated about forty degrees and the irradiation is repeated. In the second position, the tumor 1420 again receives the bulk of the irradiation energy and a second healthy tissue volume 1712 receives the smaller ingress portion of the Bragg peak energy. Referring now to FIGS. 17 C-E, the patient 1430 is rotated a total of about 90, 130, and 180 degrees, respectively. For each of the third, fourth, and fifth rotation positions, the tumor 1420 receives the bulk of the irradiation energy and the third 1713, fourth 1714, and fifth 1715 healthy tissue volumes receive the smaller ingress portion of the Bragg peak energy, respectively. Thus, the rotation of the patient during proton therapy results in the ingress energy of the delivered proton energy to be distributed about the tumor 1420, such as to regions one to five, while along a given axis, at least about 75, 80, 85, 90, or 95 percent of the energy is delivered to the tumor 1420.

For a given rotation position, all or part of the tumor is irradiated. For example, in one embodiment only a distal section or distal slice of the tumor 1420 is irradiated with each rotation position, where the distal section is a section furthest from the entry point of the proton beam into the patient 1430. For example, the distal section is the dorsal side of the tumor when the patient 1430 is facing the proton beam and the distal section is the ventral side of the tumor when the patient 1430 is facing away from the proton beam.

Figure 18:
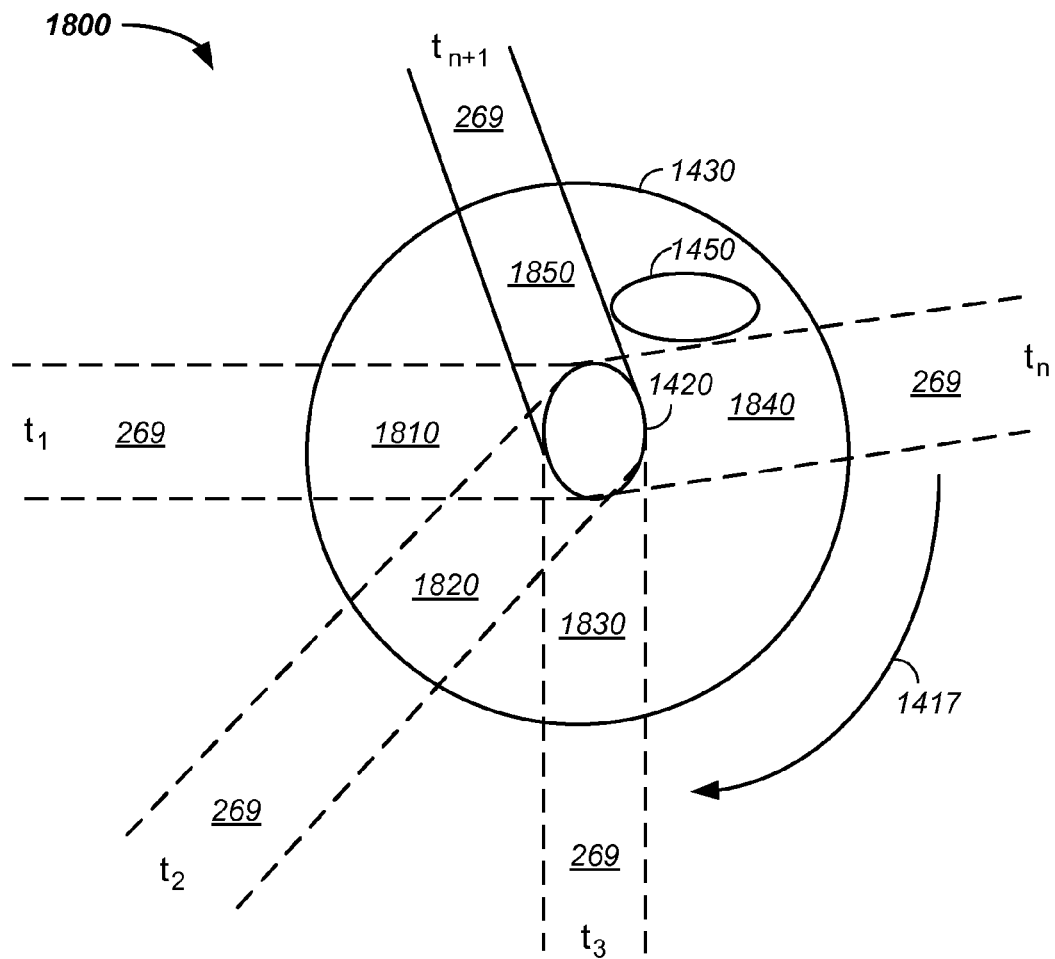
FIG. 18 illustrates dose efficiency enhancement via use of multi-field irradiation.

Referring now to FIG. 18, a second example of multi-field irradiation 1800 is presented where the proton source is stationary and the patient 1430 is rotated. For ease of presentation, the proton beam path 269 is illustrated as entering the patient 1430 from varying sides at times $t_1, t_2, t_3, \ldots, t_n, t_{n+1}$. At a first time, $t_1$, the low energy delivery end or ingress end of the Bragg peak profile hits a first area 1810, $A_1$. The pahtient is rotated and the proton beam path is illustrated at a second time, $t_2$, where the low energy end of the Bragg peak hits a second area 1820, $A_2$. At a third time, the ingress area of the Bragg peak profile hits a third area 1830, $A_3$. This rotation and irradiation process is repeated n times, where n is a positive number greater than four and preferably greater than about 10, 20, 30, 100, or 300. At an $n^{th}$ time the ingress end of the Bragg peak profile strikes an $n^{th}$ area 1840. As illustrated, at an $n^{th}$ time, $t_n$, if the patient 1430 is rotated further, the proton beam would hit a sensitive body constituent 1450, such as the spinal cord or eyes. Irradiation is preferably suspended until the sensitive body constituent is rotated out of the proton beam path. Irradiation is resumed at a time, $t_{n+1}$, after the sensitive body constituent 1450 is rotated our of the proton beam path. At time $t_{n+1}$ the Bragg peak ingress energy strikes a $t_{n+1}$ area 1450. At times 1, 2, 3, ... n, n+1, the high energy distal region of Bragg peak profile falls within the tumor 1420. In this manner, the Bragg peak energy is always within the tumor, the ingress region of the Bragg peak profile is distributed in healthy tissue about the tumor 1420, and sensitive body constituents 1450 receive minimal or no proton beam irradiation.

Proton Delivery Efficiency

Herein, charged particle or proton delivery efficiency is radiation dose delivered to the tumor compared to radiation dose delivered to the healthy regions of the patient.

A proton delivery enhancement method is described where proton delivery efficiency is enhanced, optimized, or maximized. In general, multi-field irradiation is used to deliver protons to the tumor from a multitude of rotational directions. From each direction, the energy of the protons is adjusted to target the distal portion of the tumor, where the distal portion of the tumor is the volume of the tumor furthest from the entry point of the proton beam into the body.

For clarity, the process is described using an example where the outer edges of the tumor are initially irradiated using distally applied radiation through a multitude of rotational positions, such as through 360 degrees. This results in a symbolic or calculated remaining smaller tumor for irradiation. The process is then repeated as many times as necessary on the smaller tumor. However, the presentation is for clarity. In actuality, irradiation from a given rotational angle is performed once with z-axis proton beam energy and intensity being adjusted for the calculated smaller inner tumors during x- and y-axis scanning.

Referring now to FIG. 19, the proton delivery enhancement method is further described. Referring now to FIG. 19A, at a first point in time protons are delivered to the tumor 1420 of the patient 1430 from a first direction. From the first rotational direction, the proton beam is scanned 269 across the tumor. As the proton beam is scanned across the tumor the energy of the proton beam is adjusted to allow the Bragg peak energy to target the distal portion of the tumor. Again, distal refers to the back portion of the tumor located furthest away from where the charged particles enter the tumor. As illustrated, the proton beam is scanned along an x-axis across the patient. This process allows the Bragg peak energy to fall within the tumor, for the middle area of the Bragg peak profile to fall in the middle and proximal portion of the tumor, and for the small intensity ingress portion of the Bragg peak to hit healthy tissue. In this manner, the maximum radiation dose is delivered to the tumor or the proton dose efficiency is maximized for the first rotational direction.

Figure 19A:
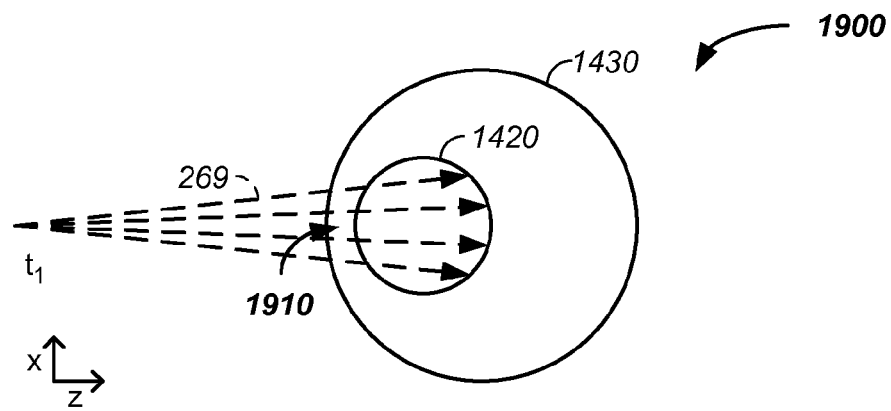
FIGS. 19A-C and FIG. 19E illustrate distal irradiation of a tumor from varying rotational directions and FIG. 19D illustrates integrated radiation resulting from distal radiation.
Figure 19B:
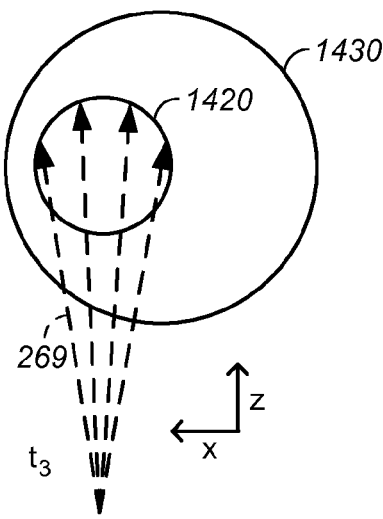
Figure 19C:
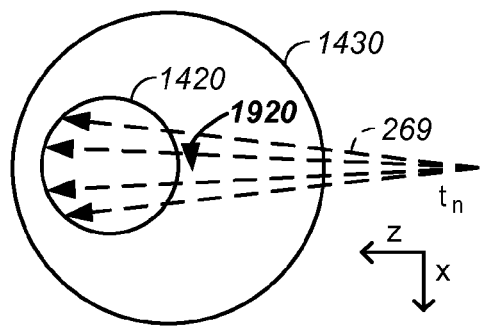

After irradiation from the first rotational position, the patient is rotated to a new rotational position. Referring now to FIG. 19B, the scanning of the proton beam is repeated. Again, the distal portion of the tumor is targeted with adjustment of the proton beam energy to target the Bragg peak energy to the distal portion of the tumor. Naturally, the distal portion of the tumor for the second rotational position is different from the distal portion of the tumor for the first rotational position. Referring now to FIG. 19C, the process of rotating the patient and then irradiating the new distal portion of the tumor is further illustrated at an $n^{th}$ rotational position. Preferably, the process of rotating the patient and scanning along the x- and y-axes with the Z-axes energy targeting the new distal portion of the tumor is repeated, such as with more than 5, 10, 20, or 30 rotational positions or with about 36 rotational positions.

For clarity, FIGS. 19A-C and FIG. 19E show the proton beam as having moved, but in actuality, the proton beam is stationary and the patient is rotated, such as via use of rotating the bottom unit 1412 of the patient positioning system 1410. Also, FIGS. 19A-C and FIG. 19E show the proton beam being scanned across the tumor along the x-axis. Though not illustrated for clarity, the proton beam is additionally scanned up and down the tumor along the y-axis of the patient. Combined, the distal portion or volume of the tumor is irradiated along the x- and y-axes with adjustment of the z-axis energy level of the proton beam. In one case, the tumor is scanned along the x-axis and the scanning is repeated along the x-axis for multiple y-axis positions. In another case, the tumor is scanned along the y-axis and the scanning is repeated along the y-axis for multiple x-axis positions. In yet another case, the tumor is scanned by simultaneously adjusting the x- and y-axes so that the distal portion of the tumor is targeted. In all of these cases, the z-axis or energy of the proton beam is adjusted along the contour of the distal portion of the tumor to target the Bragg peak energy to the distal portion of the tumor.

Figure 19D:
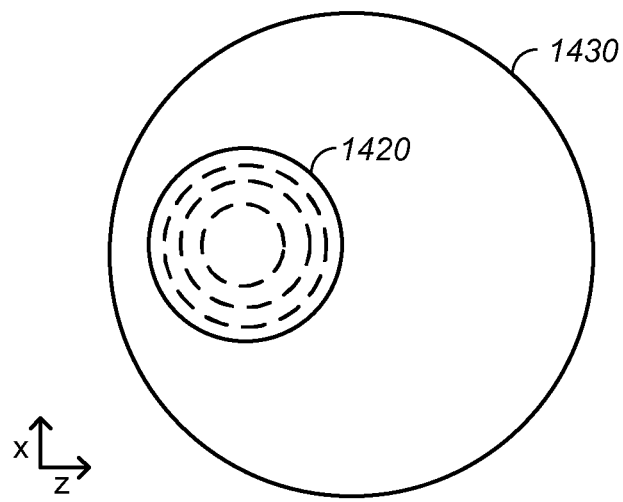

Referring now to FIG. 19D, after targeting the distal portion of the tumor from multiple directions, such as through 360 degrees, the outer perimeter of the tumor has been strongly irradiated with peak Bragg profile energy, the middle of the Bragg peak energy profile energy has been delivered along an inner edge of the heavily irradiated tumor perimeter, and smaller dosages from the ingress portion of the Bragg energy profile are distributed throughout the tumor and into some healthy tissue. The delivered dosages or accumulated radiation flux levels are illustrated in a cross-sectional area of the tumor 1420 using an iso-line plot. After a first full rotation of the patient, symbolically, the darkest regions of the tumor are nearly fully irradiated and the regions of the tissue having received less radiation are illustrated with a gray scale with the whitest portions having the lowest radiation dose.

Figure 19E:
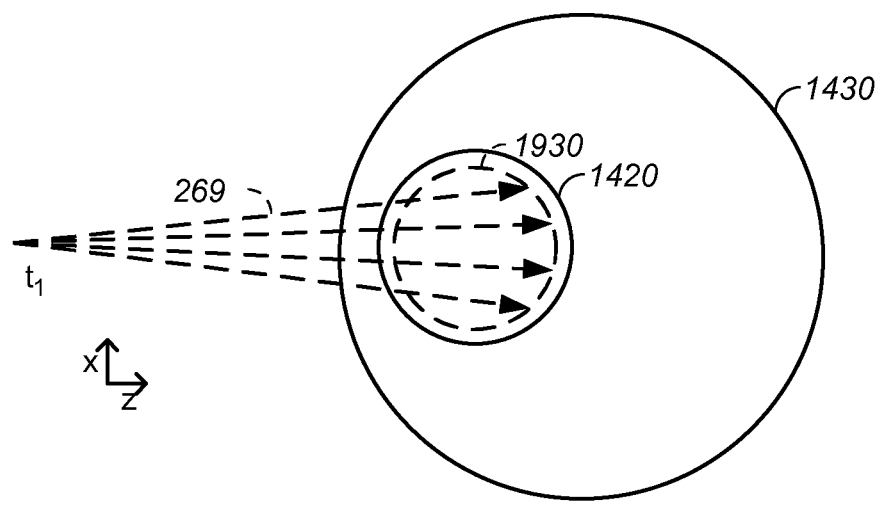

Referring now to FIG. 19E, after completing the distal targeting multi-field irradiation, a smaller inner tumor is defined, where the inner tumor is already partially irradiated. The smaller inner tumor is indicated by the dashed line 1930.

The above process of irradiating the tumor is repeated for the newly defined smaller tumor. The proton dosages to the outer or distal portions of the smaller tumor are adjusted to account for the dosages delivered from other rotational positions. After the second tumor is irradiated, a yet smaller third tumor is defined. The process is repeated until the entire tumor is irradiated at the prescribed or defined dosage.

As described at the onset of this example, the patient is preferably only rotated to each rotational position once. In the above described example, after irradiation of the outer perimeter of the tumor, the patient is rotationally positioned, such as through 360 degrees, and the distal portion of the newest smaller tumor is targeted as described, supra. However, the irradiation dosage to be delivered to the second smaller tumor and each subsequently smaller tumor is known a-priori. Hence, when at a given angle of rotation, the smaller tumor or multiple progressively smaller tumors, are optionally targeted so that the patient is only rotated to the multiple rotational irradiation positions once.

The goal is to deliver a treatment dosage to each position of the tumor, to preferably not exceed the treatment dosage to any position of the tumor, to minimize ingress radiation dosage to healthy tissue, to circumferentially distribute ingress radiation hitting the healthy tissue, and to further minimize ingress radiation dosage to sensitive areas. Since the Bragg energy profile is known, it is possible to calculated the optimal intensity and energy of the proton beam for each rotational position and for each x- and y-axis scanning position. These calculation result in slightly less than threshold radiation dosage to be delivered to the distal portion of the tumor for each rotational position as the ingress dose energy from other positions bring the total dose energy for the targeted position up to the threshold delivery dose.

Referring again to FIG. 19A and FIG. 19C, the intensity of the proton beam is preferably adjusted to account for the cross-sectional distance or density of the healthy tissue. An example is used for clarity. Referring now to FIG. 19A, when irradiating from the first position where the healthy tissue has a small area 1910, the intensity of the proton beam is preferably increased as relatively less energy is delivered by the ingress portion of the Bragg profile to the healthy tissue. Referring now to FIG. 19C, in contrast when irradiating from the $n^{th}$ rotational position where the healthy tissue has a large cross-sectional area 1920, the intensity of the proton beam is preferably decreased as a greater fraction the proton dose is delivered to the healthy tissue from this orientation.

In one example, for each rotational position and/or for each z-axis distance into the tumor, the efficiency of proton dose delivery to the tumor is calculated. The intensity of the proton beam is made proportional to the calculated efficiency. Essentially, when the scanning direction has really good efficiency, the intensity is increased and vise-versa. For example, if the tumor is elongated, generally the efficiency of irradiating the distal portion by going through the length of the tumor is higher than irradiating a distal region of the tumor by going across the tumor with the Bragg energy distribution. Generally, in the optimization algorithm:

distal portions of the tumor are targeted for each rotational position;
  the intensity of the proton beam is largest with the largest cross-sectional area of the tumor;
  intensity is larger when the intervening healthy tissue volume is smallest; and
  intensity is minimized or cut to zero when the intervening healthy tissue volume includes sensitive tissue, such as the spinal cord or eyes.

Using an exemplary algorithm, the efficiency of radiation dose delivery to the tumor is maximized. More particularly, the ratio of radiation dose delivered to the tumor versus the radiation dose delivered to surrounding healthy tissue approaches a maximum. Further, integrated radiation dose delivery to each x, y, and z-axis volume of the tumor as a result of irradiation from multiple rotation directions is at or near the preferred dose level. Still further, ingress radiation dose delivery to healthy tissue is circumferentially distributed about the tumor via use of multi-field irradiation where radiation is delivered from a plurality of directions into the body, such as more than 5, 10, 20, or 30 directions.

In one example, the intensity of the charged particle beam correlates with energy of the charged particle beam. For instance, if the round tumor is exactly in the center of a healthy tissue volume, efficiency of radiation delivery is maximized when targeting the distal region of the tumor from a given direction, which occurs with maximum energy. When radiation delivery is maximized, the intensity of the charged particles is preferably maximized. Conversely, when the energy is targeting a proximal region of a tumor, then the efficiency of energy delivery to the tumor is small as the ingress energy of the charged particle beam is higher when striking healthy tissue. Thus, the intensity of the charged particle beam is preferably lower when the energy of the charged particle beam is lower. Preferably, a correlation coefficient of the intensity to the energy is at least 0.25 and preferably at least about 0.5, 0.75, or 0.9. Generally, for a non-centrally placed tumor in healthy tissue, for irradiation from one of a number of irradiation directions, the intensity of the charged particle beam is increased as the energy level of the charged particle beam is increased.

Multi-Field Irradiation

In one multi-field irradiation example, the particle therapy system with a synchrotron ring diameter of less than six meters includes ability to:
- rotate the patient through about 360 degrees;
- extract radiation in about 0.1 to 10 seconds;
- scan vertically about 100 millimeters;
- scan horizontally about 700 millimeters;
- vary beam energy from about 30 to 330 MeV/second during irradiation;
- focus the proton beam from about 2 to 20 millimeters at the tumor; and/or
- complete multi-field irradiation of a tumor in less than about 1, 2, 4, or 6 minutes as measured from the time of initiating proton delivery to the patient 1430.

Figure 20:
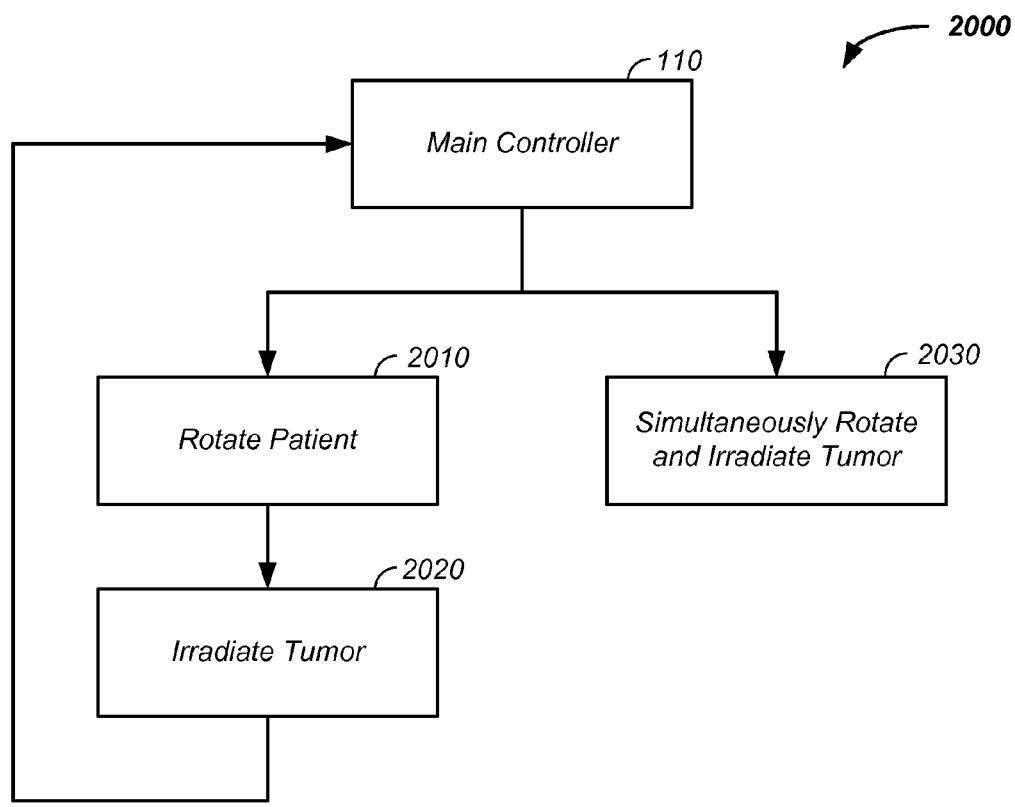
FIG. 20 provides two methods of multi-field irradiation implementation.

Referring now to FIG. 20, two multi-field irradiation methods 2000 are described. In the first method, the main controller 110 rotationally positions 2010 the patient 1430 and subsequently irradiates 2020 the tumor 1420. The process is repeated until a multi-field irradiation plan is complete. In the second method, the main controller 110 simultaneously rotates and irradiates 2030 the tumor 1420 within the patient 1430 until the multi-field irradiation plan is complete. More particularly, the proton beam irradiation occurs while the patient 1430 is being rotated.

The 3-dimensional scanning system of the proton spot focal point, described herein, is preferably combined with a rotation/raster method. The method includes layer wise tumor irradiation from many directions. During a given irradiation slice, the proton beam energy is continuously changed according to the tissue's density in front of the tumor to result in the beam stopping point, defined by the Bragg peak, to always be inside the tumor and inside the irradiated slice. The novel method allows for irradiation from many directions, referred to herein as multi-field irradiation, to achieve the maximal effective dose at the tumor level while simultaneously significantly reducing possible side-effects on the surrounding healthy tissues in comparison with existing methods. Essentially, the multi-field irradiation system distributes dose-distribution at tissue depths not yet reaching the tumor.

Proton Beam Position Control

Referring now to FIG. 21, a beam delivery and tissue volume scanning system is illustrated. Presently, the worldwide radiotherapy community uses a method of dose field forming using a pencil beam scanning system. In stark contrast, FIG. 21 illustrates a spot scanning system or tissue volume scanning system. In the tissue volume scanning system, the proton beam is controlled, in terms of transportation and distribution, using an inexpensive and precise scanning system. The scanning system is an active system, where the beam is focused into a spot focal point of about one-half, one, two, or three millimeters in diameter. The focal point is translated along two axes while simultaneously altering the applied energy of the proton beam, which effectively changes the third dimension of the focal point. The system is applicable in combination with the above described rotation of the body, which preferably occurs in-between individual moments or cycles of proton delivery to the tumor. Optionally, the rotation of the body by the above described system occurs continuously and simultaneously with proton delivery to the tumor.

Figure 21A:
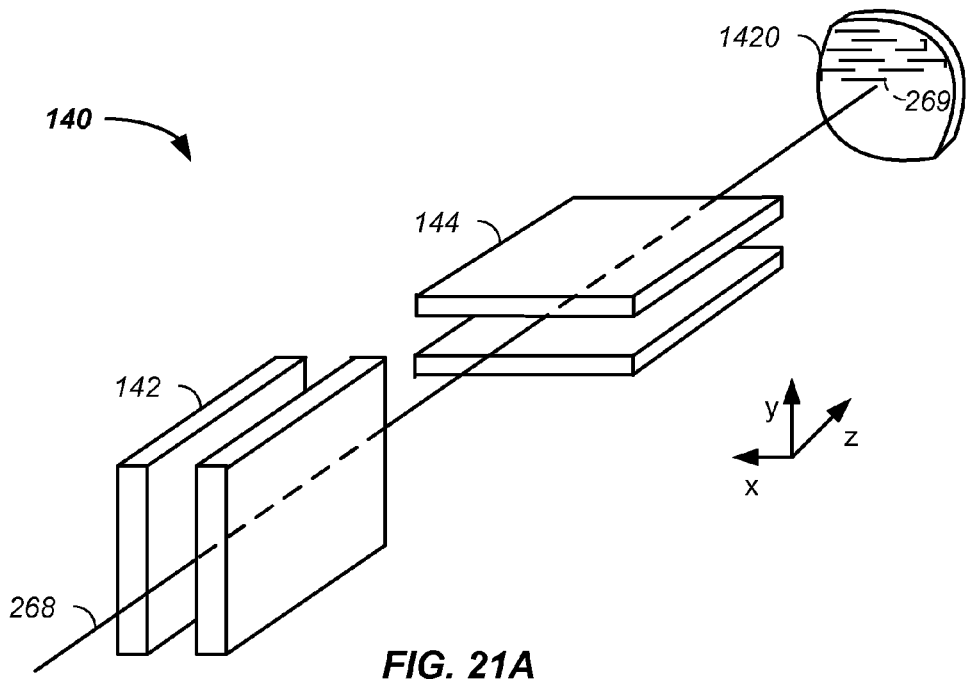
FIG. 21 illustrates multi-dimensional scanning of a charged particle beam spot scanning system operating on: (A) a 2-D slice or (B) a 3-D volume of a tumor.

For example, in the illustrated system in FIG. 21A, the spot is translated horizontally, is moved down a vertical y-axis, and is then back along the horizontal axis. In this example, current is used to control a vertical scanning system having at least one magnet. The applied current alters the magnetic field of the vertical scanning system to control the vertical deflection of the proton beam. Similarly, a horizontal scanning magnet system controls the horizontal deflection of the proton beam. The degree of transport along each axes is controlled to conform to the tumor cross-section at the given depth. The depth is controlled by changing the energy of the proton beam. For example, the proton beam energy is decreased, so as to define a new penetration depth, and the scanning process is repeated along the horizontal and vertical axes covering a new cross-sectional area of the tumor. Combined, the three axes of control allow scanning or movement of the proton beam focal point over the entire volume of the cancerous tumor. The time at each spot and the direction into the body for each spot is controlled to yield the desired radiation does at each sub-volume of the cancerous volume while distributing energy hitting outside of the tumor.

The focused beam spot volume dimension is preferably tightly controlled to a diameter of about 0.5, 1, or 2 millimeters, but is alternatively several centimeters in diameter. Preferred design controls allow scanning in two directions with: (1) a vertical amplitude of about 100 mm amplitude and frequency up to about 200 Hz; and (2) a horizontal amplitude of about 700 mm amplitude and frequency up to about 1 Hz.

In FIG. 21A, the proton beam is illustrated along a z-axis controlled by the beam energy, the horizontal movement is along an x-axis, and the vertical direction is along a y-axis. The distance the protons move along the z-axis into the tissue, in this example, is controlled by the kinetic energy of the proton. This coordinate system is arbitrary and exemplary. The actual control of the proton beam is controlled in 3-dimensional space using two scanning magnet systems and by controlling the kinetic energy of the proton beam. The use of the extraction system, described supra, allows for different scanning patterns. Particularly, the system allows simultaneous adjustment of the x-, y-, and z-axes in the irradiation of the solid tumor. Stated again, instead of scanning along an x,y-plane and then adjusting energy of the protons, such as with a range modulation wheel, the system allows for moving along the z-axes while simultaneously adjusting the x- and or y-axes. Hence, rather than irradiating slices of the tumor, the tumor is optionally irradiated in three simultaneous dimensions. For example, the tumor is irradiated around an outer edge of the tumor in three dimensions. Then the tumor is irradiated around an outer edge of an internal section of the tumor. This process is repeated until the entire tumor is irradiated. The outer edge irradiation is preferably coupled with simultaneous rotation of the subject, such as about a vertical y-axis. This system allows for maximum efficiency of deposition of protons to the tumor, as defined as the ratio of the proton irradiation energy delivered to the tumor relative to the proton irradiation energy delivered to the healthy tissue.

Combined, the system allows for multi-axis control of the charged particle beam system in a small space with low power supply. For example, the system uses multiple magnets where each magnet has at least one edge focusing effect in each turning section of the synchrotron and/or multiple magnets having concentrating magnetic field geometry, as described supra. The multiple edge focusing effects in the circulating beam path of the synchrotron combined with the concentration geometry of the magnets and described extraction system yields a synchrotron having:
- a small circumference system, such as less than about 50 meters;
- a vertical proton beam size gap of about 2 cm;
- corresponding reduced power supply requirements associated with the reduced gap size;
- an extraction system not requiring a newly introduced magnetic field;
- acceleration or deceleration of the protons during extraction; and
- control of z-axis energy during extraction.

The result is a 3-dimensional scanning system, x-, y-, and z-axes control, where the z-axes control resides in the synchrotron and where the z-axes energy is variably controlled during the extraction process inside the synchrotron.

Figure 21B:
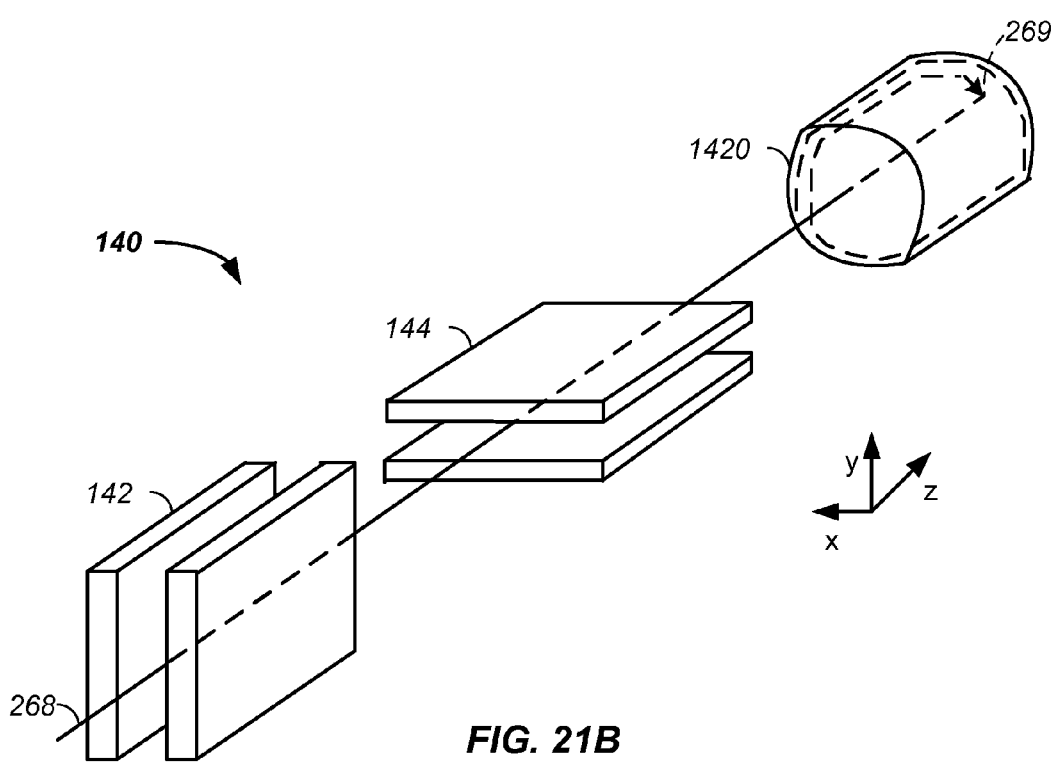

Referring now to FIG. 21B, an example of a proton scanning or targeting system 140 used to direct the protons to the tumor with 4-dimensional scanning control is provided, where the 4-dimensional scanning control is along the x-, y-, and z-axes along with intensity control, as described supra. A fifth axis is time. Typically, charged particles traveling along the transport path 268 are directed through a first axis control element 142, such as a vertical control, and a second axis control element 144, such as a horizontal control and into a tumor 1420. As described, supra, the extraction system also allows for simultaneous variation in the z-axis. Further, as describe, supra, the intensity or dose of the extracted beam is optionally simultaneously and independently controlled and varied. Thus instead of irradiating a slice of the tumor, as in FIG. 21A, all four dimensions defining the targeting spot of the proton delivery in the tumor are simultaneously variable. The simultaneous variation of the proton delivery spot is illustrated in FIG. 21B by the spot delivery path 269. In the illustrated case, the protons are initially directed around an outer edge of the tumor and are then directed around an inner radius of the tumor. Combined with rotation of the subject about a vertical axis, a multi-field illumination process is used where a not yet irradiated portion of the tumor is preferably irradiated at the further distance of the tumor from the proton entry point into the body. This yields the greatest percentage of the proton delivery, as defined by the Bragg peak, into the tumor and minimizes damage to peripheral healthy tissue.

Imaging/X-Ray System

Herein, an X-ray system is used to illustrate an imaging system.

Timing

An X-ray is preferably collected either (1) just before or (2) concurrently with treating a subject with proton therapy for a couple of reasons. First, movement of the body, described supra, changes the local position of the tumor in the body relative to other body constituents. If the subject has an X-ray taken and is then bodily moved to a proton treatment room, accurate alignment of the proton beam to the tumor is problematic. Alignment of the proton beam to the tumor using one or more X-rays is best performed at the time of proton delivery or in the seconds or minutes immediately prior to proton delivery and after the patient is placed into a therapeutic body position, which is typically a fixed position or partially immobilized position. Second, the X-ray taken after positioning the patient is used for verification of proton beam alignment to a targeted position, such as a tumor and/or internal organ position.

Positioning

An X-ray is preferably taken just before treating the subject to aid in patient positioning. For positioning purposes, an X-ray of a large body area is not needed. In one embodiment, an X-ray of only a local area is collected. When collecting an X-ray, the X-ray has an X-ray path. The proton beam has a proton beam path. Overlaying the X-ray path with the proton beam path is one method of aligning the proton beam to the tumor. However, this method involves putting the X-ray equipment into the proton beam path, taking the X-ray, and then moving the X-ray equipment out of the beam path. This process takes time. The elapsed time while the X-ray equipment moves has a couple of detrimental effects. First, during the time required to move the X-ray equipment, the body moves. The resulting movement decreases precision and/or accuracy of subsequent proton beam alignment to the tumor. Second, the time required to move the X-ray equipment is time that the proton beam therapy system is not in use, which decreases the total efficiency of the proton beam therapy system.

X-Ray Source Lifetime

Preferably, components in the particle beam therapy system require minimal or no maintenance over the lifetime of the particle beam therapy system. For example, it is desirable to equip the proton beam therapy system with an X-ray system having a long lifetime source, such as a lifetime of about 20 years.

In one system, described infra, electrons are used to create X-rays. The electrons are generated at a cathode where the lifetime of the cathode is temperature dependent. Analogous to a light bulb, where the filament is kept in equilibrium, the cathode temperature is held in equilibrium at temperatures at about 200, 500, or 1000 degrees Celsius. Reduction of the cathode temperature results in increased lifetime of the cathode. Hence, the cathode used in generating the electrons is preferably held at as low of a temperature as possible. However, if the temperature of the cathode is reduced, then electron emissions also decrease. To overcome the need for more electrons at lower temperatures, a large cathode is used and the generated electrons are concentrated. The process is analogous to compressing electrons in an electron gun; however, here the compression techniques are adapted to apply to enhancing an X-ray tube lifetime.

Figure 22:
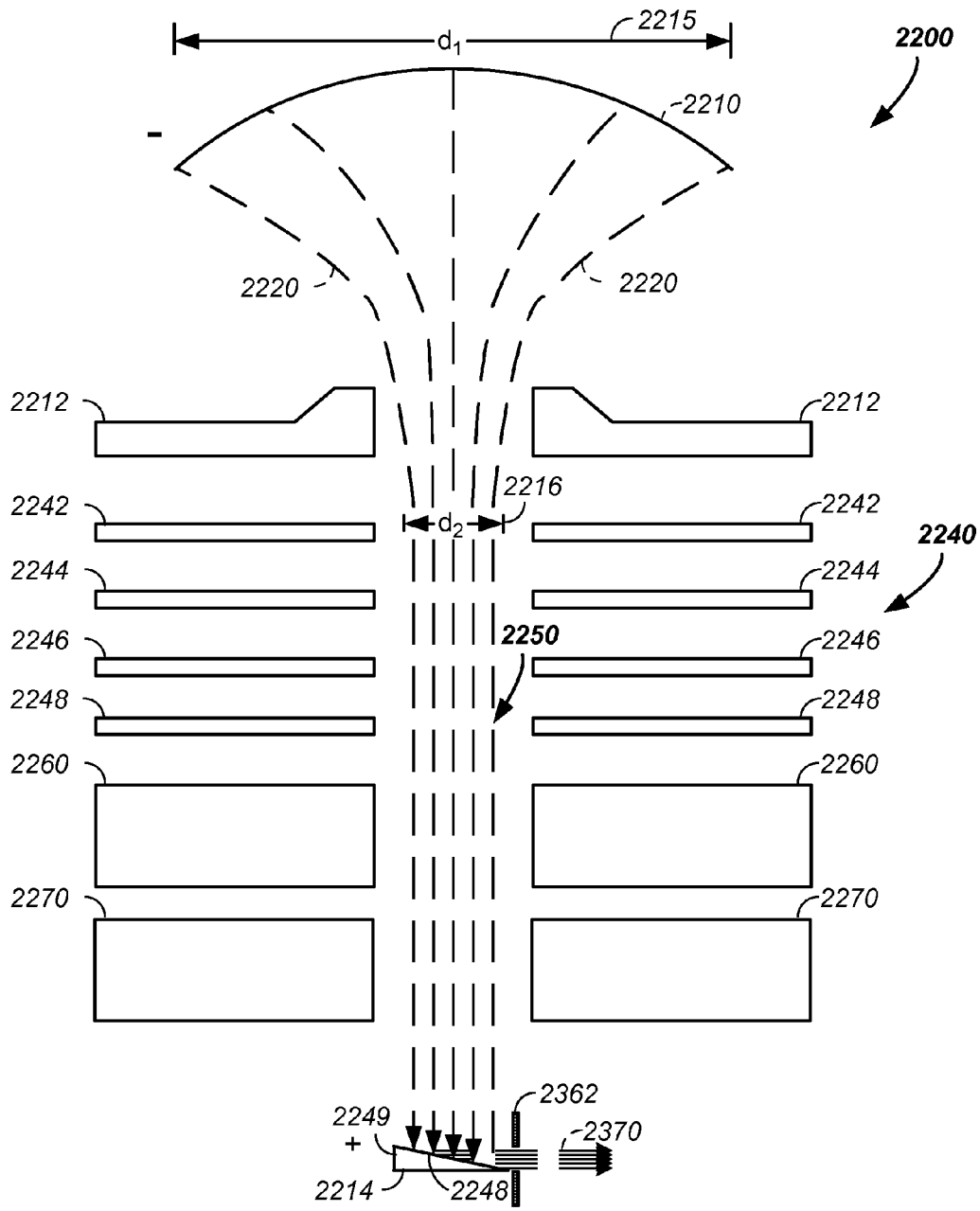
FIG. 22 illustrates an electron gun source used in generating X-rays coupled with a particle beam therapy system.

Referring now to FIG. 22, an example of an X-ray generation device 2200 having an enhanced lifetime is provided. Electrons 2220 are generated at a cathode 2210, focused with a control electrode 2212, and accelerated with a series of accelerating electrodes 2240. The accelerated electrons 2250 impact an X-ray generation source 2248 resulting in generated X-rays that are then directed along an X-ray path 2370 to the subject 1430. The concentrating of the electrons from a first diameter 2215 to a second diameter 2216 allows the cathode to operate at a reduced temperature and still yield the necessary amplified level of electrons at the X-ray generation source 2248. In one example, the X-ray generation source is the anode coupled with the cathode 2210 and/or the X-ray generation source is substantially composed of tungsten.

Still referring to FIG. 22, a more detailed description of an exemplary X-ray generation device 2200 is described. An anode 2214/cathode 2210 pair is used to generated electrons. The electrons 2220 are generated at the cathode 2210 having a first diameter 2215, which is denoted $d_1$. The control electrodes 2212 attract the generated electrons 2220. For example, if the cathode is held at about −150 kV and the control electrode is held at about −149 kV, then the generated electrons 2220 are attracted toward the control electrodes 2212 and focused. A series of accelerating electrodes 2240 are then used to accelerate the electrons into a substantially parallel path 2250 with a smaller diameter 2116, which is denoted $d_2$. For example, with the cathode held at −150 kV, a first, second, third, and fourth accelerating electrodes 2242, 2244, 2246, 2248 are held at about −120, −90, −60, and −30 kV, respectively. If a thinner body part is to be analyzed, then the cathode 2210 is held at a smaller level, such as about −90 kV and the control electrode, first, second, third, and fourth electrode are each adjusted to lower levels. Generally, the voltage difference from the cathode to fourth electrode is less for a smaller negative voltage at the cathode and vise-versa. The accelerated electrons 2250 are optionally passed through a magnetic lens 2260 for adjustment of beam size, such as a cylindrical magnetic lens. The electrons are also optionally focused using quadrupole magnets 2270, which focus in one direction and defocus in another direction. The accelerated electrons 2250, which are now adjusted in beam size and focused strike an X-ray generation source 2248, such as tungsten, resulting in generated X-rays that pass through a blocker 2362 and proceed along an X-ray path 2270 to the subject. The X-ray generation source 2248 is optionally cooled with a cooling element 2249, such as water touching or thermally connected to a backside of the X-ray generation source 2248. The concentrating of the electrons from a first diameter 2215 to a second diameter 2216 allows the cathode to operate at a reduced temperature and still yield the necessary amplified level of electrons at the X-ray generation source 2248.

More generally, the X-ray generation device 2200 produces electrons having initial vectors. One or more of the control electrode 2212, accelerating electrodes 2240, magnetic lens 2260, and quadrupole magnets 2270 combine to alter the initial electron vectors into parallel vectors with a decreased cross-sectional area having a substantially parallel path, referred to as the accelerated electrons 2250. The process allows the X-ray generation device 2200 to operate at a lower temperature. Particularly, instead of using a cathode that is the size of the electron beam needed, a larger electrode is used and the resulting electrons 2220 are focused and/or concentrated into the required electron beam needed. As lifetime is roughly an inverse of current density, the concentration of the current density results in a larger lifetime of the X-ray generation device. A specific example is provided for clarity. If the cathode has a fifteen mm radius or $d_1$ is about 30 mm, then the area ($\pi r^2$) is about 225 mm² times pi. If the concentration of the electrons achieves a radius of five mm or $d_2$ is about 10 mm, then the area ($\pi r^2$) is about 25 mm² times pi. The ratio of the two areas is about nine ($225\pi/25\pi$). Thus, there is about nine times less density of current at the larger cathode compared to the traditional cathode having an area of the desired electron beam. Hence, the lifetime of the larger cathode approximates nine times the lifetime of the traditional cathode, though the actual current through the larger cathode and traditional cathode is about the same. Preferably, the area of the cathode 2210 is about 2, 4, 6, 8, 10, 15, 20, or 25 times that of the cross-sectional area of the substantially parallel electron beam 2150.

In another embodiment of the invention, the quadrupole magnets 2270 result in an oblong cross-sectional shape of the electron beam 2250. A projection of the oblong cross-sectional shape of the electron beam 2250 onto the X-ray generation source 2248 results in an X-ray beam that has a small spot in cross-sectional view, which is preferably substantially circular in cross-sectional shape, that is then passed through the patient 1430. The small spot is used to yield an X-ray having enhanced resolution at the patient.

Figure 23:
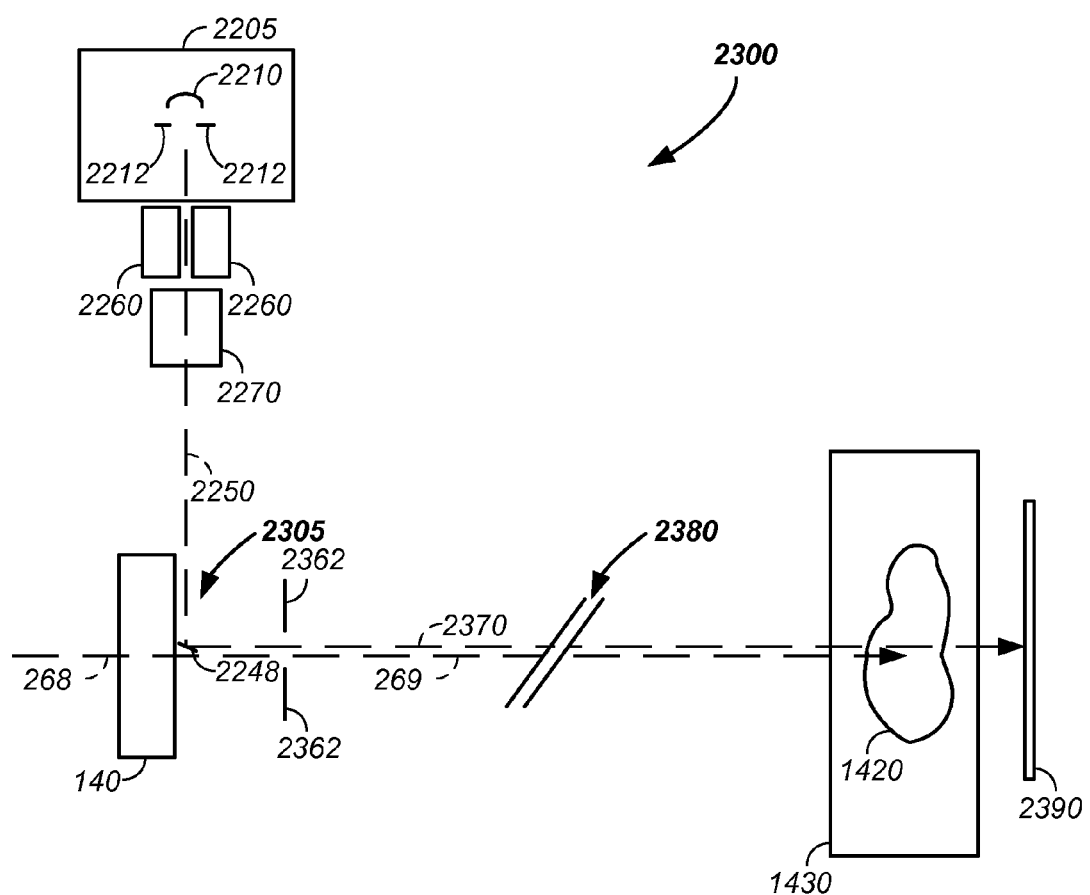
FIG. 23 illustrates an X-ray source proximate a particle beam path.

Referring now to FIG. 23, in one embodiment, an X-ray is generated close to, but not in, the proton beam path. A proton beam therapy system and an X-ray system combination 2300 is illustrated in FIG. 23. The proton beam therapy system has a proton beam 268 in a transport system after the Lamberson extraction magnet 292 of the synchrotron 130. The proton beam is directed by the scanning/targeting/delivery system 140 to a tumor 1420 of a patient 1430. The X-ray system 2305 includes an electron beam source 2205 generating an electron beam 2250. The electron beam is directed to an X-ray generation source 2248, such as a piece of tungsten. Preferably, the tungsten X-ray source is located about 1, 2, 3, 5, 10, 15, 20, or 40 millimeters from the proton beam path 268. When the electron beam 2250 hits the tungsten, X-rays are generated. In a case where the X-rays are generated in all directions, X-rays are preferably blocked with a port 2362 and are selected for an X-ray beam path 2370. In a second case, the geometry of the electron beam 2250 and X-ray generation source 2248 yield generated X-rays 2270 having a directionality, such as aligned with the proton beam 268. In either case, the X-ray beam path 2370 and proton beam path 268 run substantially in parallel as they progress to the tumor 1420. The distance between the X-ray beam path 2370 and proton beam path 269 preferably diminishes to near zero and/or the X-ray beam path 2370 and proton beam path 269 overlap by the time they reach the tumor 1420. Simple geometry shows this to be the case given the long distance, of at least a meter, between the tungsten and the tumor 1420. The distance is illustrated as a gap 2380 in FIG. 23. The X-rays are detected at an X-ray detector 2390, which is used to form an image of the tumor 1420 and/or position of the patient 1430.

As a whole, the system generates an X-ray beam that lies in substantially the same path as the proton therapy beam. The X-ray beam is generated by striking a tungsten or equivalent material with an electron beam. The X-ray generation source is located proximate to the proton beam path. Geometry of the incident electrons, geometry of the X-ray generation material, and geometry of the X-ray beam blocker 262 yield an X-ray beam that runs either in substantially in parallel with the proton beam or results in an X-ray beam path that starts proximate the proton beam path an expands to cover and transmit through a tumor cross-sectional area to strike an X-ray detector array or film allowing imaging of the tumor from a direction and alignment of the proton therapy beam. The X-ray image is then used to control the charged particle beam path to accurately and precisely target the tumor, and/or is used in system verification and validation.

Having an X-ray generation source 2248 that is proximate the proton beam path 268 allows for an X-ray of the patient 1430 to be collected close in time to use of the proton beam for tumor 1420 therapy as the X-ray generation source 2248 need not be mechanically moved prior to proton therapy. For instance, proton irradiation of the tumor 1420 occurs within about 1, 5, 10, 20, 30, or 60 seconds of when the X-ray is collected.

Patient Immobilization

Accurate and precise delivery of a proton beam to a tumor of a patient requires: (1) positioning control of the proton beam and (2) positioning control of the patient. As described, supra, the proton beam is controlled using algorithms and magnetic fields to a diameter of about 0.5, 1, or 2 millimeters. This section addresses partial immobilization, restraint, and/or alignment of the patient to insure the tightly controlled proton beam efficiently hits a target tumor and not surrounding healthy tissue as a result of patient movement.

In this section an x-, y-, and z-axes coordinate system and rotation axis is used to describe the orientation of the patient relative to the proton beam. The z-axis represent travel of the proton beam, such as the depth of the proton beam into the patient. When looking at the patient down the z-axis of travel of the proton beam, the x-axis refers to moving left or right across the patient and the y-axis refers to movement up or down the patient. A first rotation axis is rotation of the patient about the y-axis and is referred to herein as a rotation axis, bottom unit 1412 rotation axis, or y-axis of rotation. In addition, tilt is rotation about the x-axis, yaw is rotation about the y-axis, and roll is rotation about the z-axis. In this coordinate system, the proton beam path 269 optionally runs in any direction. As an illustrative matter, the proton beam path running through a treatment room is described as running horizontally through the treatment room.

In this section, a partial patient 1430 immobilization system 2400 is described. A semi-vertical partial immobilization system is used to illustrate key features, which are illustrative of a features in a sitting partial immobilization system or a laying positioning system.

Vertical Patient Positioning/Immobilization

Figure 24:
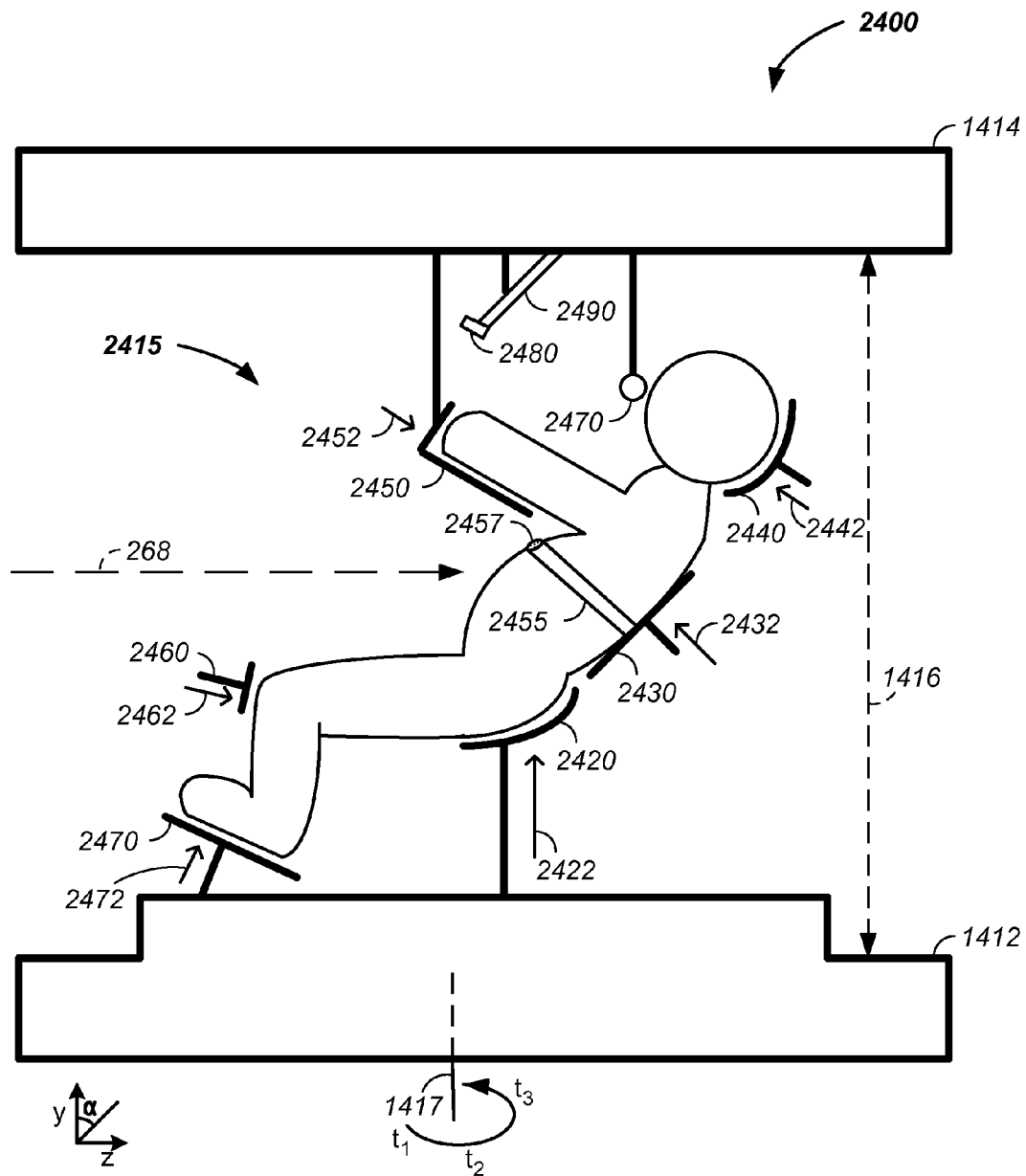
FIG. 24 illustrates a semi-vertical patient positioning system.

Referring now to FIG. 24, the semi-vertical patient positioning system 2400 is preferably used in conjunction with proton therapy of tumors in the torso. The patient positioning and/or immobilization system controls and/or restricts movement of the patient during proton beam therapy. In a first partial immobilization embodiment, the patient is positioned in a semi-vertical position in a proton beam therapy system. As illustrated, the patient is reclining at an angle alpha, $\alpha$, about 45 degrees off of the y-axis as defined by an axis running from head to foot of the patient. More generally, the patient is optionally completely standing in a vertical position of zero degrees off the of y-axis or is in a semi-vertical position alpha that is reclined about 5, 10, 15, 20, 25, 30, 35, 40, 45, 50, 55, 60, or 65 degrees off of the y-axis toward the z-axis.

Patient positioning constraints 2415 are used to maintain the patient in a treatment position, including one or more of: a seat support 2420, a back support 2430, a head support 2440, an arm support 2450, a knee support 2460, and a foot support 2470. The constraints are optionally and independently rigid or semi-rigid. Examples of a semi-rigid material include a high or low density foam or a visco-elastic foam. For example the foot support is preferably rigid and the back support is preferably semi-rigid, such as a high density foam material. One or more of the positioning constraints 2415 are movable and/or under computer control for rapid positioning and/or immobilization of the patient. For example, the seat support 2420 is adjustable along a seat adjustment axis 2422, which is preferably the y-axis; the back support 2430 is adjustable along a back support axis 2432, which is preferably dominated by z-axis movement with a y-axis element; the head support 2440 is adjustable along a head support axis 2442, which is preferably dominated by z-axis movement with a y-axis element; the arm support 2450 is adjustable along an arm support axis 2452, which is preferably dominated by z-axis movement with a y-axis element; the knee support 2460 is adjustable along a knee support axis 2462, which is preferably dominated by y-axis movement with a z-axis element; and the foot support 2470 is adjustable along a foot support axis 2472, which is preferably dominated by y-axis movement with a z-axis element.

If the patient is not facing the incoming proton beam, then the description of movements of support elements along the axes change, but the immobilization elements are the same.

An optional camera 2480 is used with the patient immobilization system. The camera views the patient/subject creating an video image. The image is provided to one or more operators of the charged particle beam system and allows the operators a safety mechanism for determining if the subject has moved or desires to terminate the proton therapy treatment procedure. Based on the video image, the operators may suspend or terminate the proton therapy procedure. For example, if the operator observes via the video image that the subject is moving, then the operator has the option to terminate or suspend the proton therapy procedure.

An optional video display 2490 is provided to the patient. The video display optionally presents to the patient any of: operator instructions, system instructions, status of treatment, or entertainment.

Motors for positioning the constraints 2415, the camera 2480, and video display 2490 are preferably mounted above or below the proton path.

Respiration control is optionally performed by using the video display. As the patient breathes, internal and external structures of the body move in both absolute terms and in relative terms. For example, the outside of the chest cavity and internal organs both have absolute moves with a breath. In addition, the relative position of an internal organ relative to another body component, such as an outer region of the body, a bone, support structure, or another organ, moves with each breath. Hence, for more accurate and precise tumor targeting, the proton beam is preferably delivered at point a in time where the position of the internal structure or tumor is well defined, such as at the bottom of each breath. The video display is used to help coordinate the proton beam delivery with the patient's breathing cycle. For example, the video display optionally displays to the patient a command, such as a hold breath statement, a breath statement, a countdown indicating when a breadth will next need to be held, or a countdown until breathing may resume.

The semi-vertical patient positioning system 2400 and sitting patient positioning system are preferentially used to treatment of tumors in the head or torso due to efficiency. The semi-vertical patient positioning system 2400, sitting patient positioning system, and laying patient positioning system are all usable for treatment of tumors in the patient's limbs.

Support System Elements

Positioning constraints 2415 include all elements used to position the patient, such as those described in the semi-vertical positioning system 2400, sitting positioning system, and laying positioning system. Preferably, positioning constraints or support system elements are aligned in positions that do not impede or overlap the proton beam path 269. However, in some instances the positioning constraints are in the proton beam path 269 during at least part of the time of treatment of the patient. For instance, a positioning constraint element may reside in the proton beam path 269 during part of a time period where the patient is rotated about the y-axis during treatment. In cases or time periods that the positioning constraints or support system elements are in the proton beam path, then an upward adjustment of proton beam energy is preferably applied that increases the proton beam energy to offset the positioning constraint element impedance of the proton beam. In one case, the proton beam energy is increased by a separate measure of the positioning constraint element impedance determined during a reference scan of the positioning constraint system element or set of reference scans of the positioning constraint element as a function of rotation about the y-axis.

For clarity, the positioning constraints 2415 or support system elements are herein described relative to the semi-vertical positioning system 2400; however, the positioning elements and descriptive x-, y-, and z-axes are adjustable to fit any coordinate system, to the sitting positioning system, or the laying positioning system.

An example of a head support system is described to support, align, and/or restrict movement of a human head. The head support system preferably has several head support elements including any of: a back of head support, a right of head alignment element, and a left of head alignment element. The back of head support element is preferably curved to fit the head and is optionally adjustable along a head support axis, such as along the z-axis. Further, the head supports, like the other patient positioning constraints, is preferably made of a semi-rigid material, such as a low or high density foam, and has an optional covering, such as a plastic or leather. The right of head alignment element and left of head alignment elements or head alignment elements, are primarily used to semi-constrain movement of the head. The head alignment elements are preferably padded and flat, but optionally have a radius of curvature to fit the side of the head. The right and left head alignment elements are preferably respectively movable along translation axes to make contact with the sides of the head. Restricted movement of the head during proton therapy is important when targeting and treating tumors in the head or neck. The head alignment elements and the back of head support element combine to restrict tilt, rotation or yaw, roll and/or position of the head in the x-, y-, z-axes coordinate system.

Figure 25:
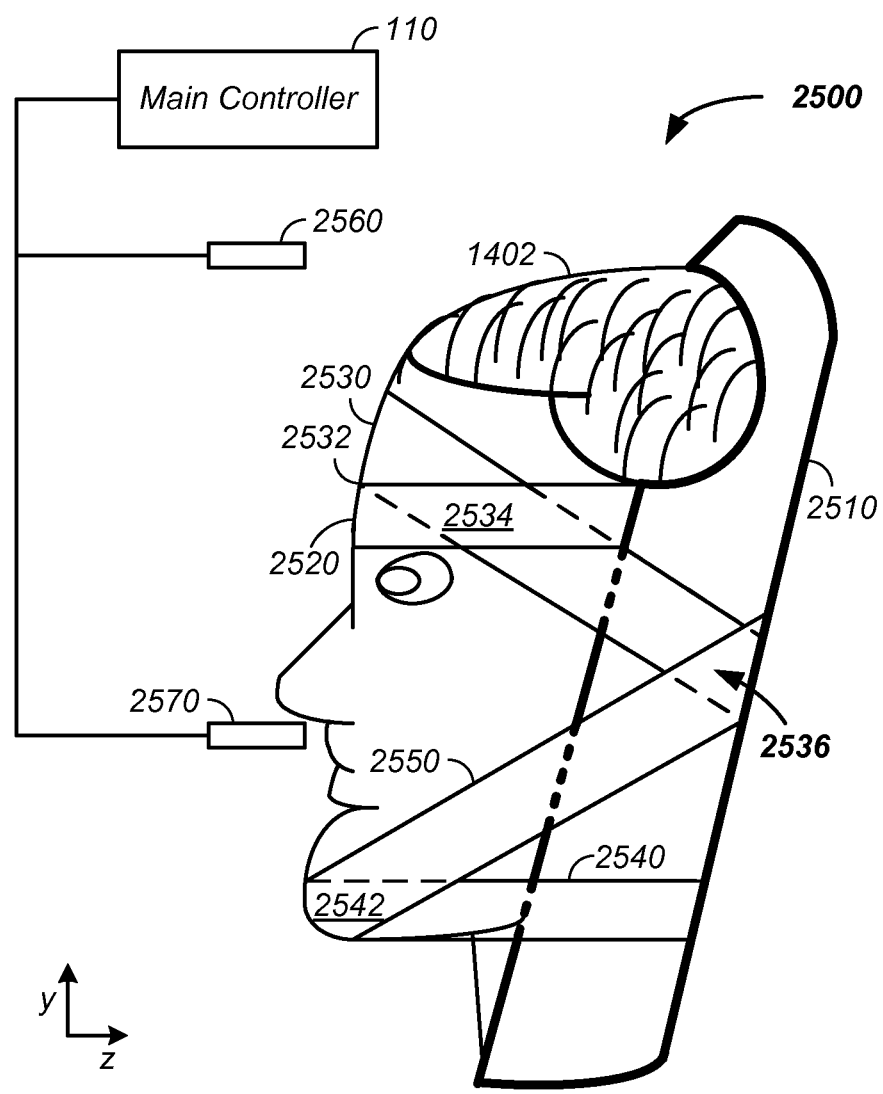
FIG. 25 illustrates respiration monitoring.

Referring now to FIG. 25 another example of a head support system 2500 is described for positioning and/or restricting movement of a human head 1402 during proton therapy of a solid tumor in the head or neck. In this system, the head is restrained using 1, 2, 3, 4, or more straps or belts, which are preferably connected or replaceably connected to a back of head support element 2510. In the example illustrated, a first strap 2520 pulls or positions the forehead to the head support element 2510, such as by running predominantly along the z-axis. Preferably a second strap 2530 works in conjunction with the first strap 2520 to prevent the head from undergoing tilt, yaw, roll or moving in terms of translational movement on the x-, y-, and z-axes coordinate system. The second strap 2530 is preferably attached or replaceable attached to the first strap 2520 at or about: (1) the forehead 2532; (2) on one or both sides of the head 2534; and/or (3) at or about the support element 2510. A third strap 2540 preferably orientates the chin of the subject relative to the support element 2510 by running dominantly along the z-axis. A fourth strap 2550 preferably runs along a predominantly y- and z-axes to hold the chin relative to the head support element 2510 and/or proton beam path. The third 2540 strap preferably is attached to or is replaceably attached to the fourth strap 2550 during use at or about the patient's chin 2542. The second strap 2530 optionally connects 2536 to the fourth strap 2550 at or about the support element 2510. The four straps 2520, 2530, 2540, 2550 are illustrative in pathway and interconnection. Any of the straps optionally hold the head along different paths around the head and connect to each other in separate fashion. Naturally, a given strap preferably runs around the head and not just on one side of the head. Any of the straps 2520, 2530, 2540, and 2550 are optionally used independently or in combinations and permutations with the other straps. The straps are optionally indirectly connected to each other via a support element, such as the head support element 2510. The straps are optionally attached to the head support element 2510 using hook and loop technology, a buckle, or fastener. Generally, the straps combine to control position, front-to-back movement of the head, side-to-side movement of the head, tilt, yaw, roll, and/or translational position of the head.

The straps are preferably of known impedance to proton transmission allowing a calculation of peak energy release along the z-axis to be calculated. For example, adjustment to the Bragg peak energy is made based on the slowing tendency of the straps to proton transport.

Positioning System Computer Control

One or more of the patient positioning unit components and/or one or more of the patient positioning constraints are preferably under computer control, where the computer control positioning devices, such as via a series of motors and drives, to reproducibly position the patient. For example, the patient is initially positioned and constrained by the patient positioning constraints. The position of each of the patient positioning constraints is recorded and saved by the main controller 110, by a sub-controller or the main controller 110, or by a separate computer controller. Then, medical devices are used to locate the tumor 1420 in the patient 1430 while the patient is in the orientation of final treatment. The imaging system 170 includes one or more of: MRI's, X-rays, CT's, proton beam tomography, and the like. Time optionally passes at this point where images from the imaging system 170 are analyzed and a proton therapy treatment plan is devised. The patient may exit the constraint system during this time period, which may be minutes, hours, or days. Upon return of the patient to the patient positioning unit, the computer can return the patient positioning constraints to the recorded positions. This system allows for rapid repositioning of the patient to the position used during imaging and development of the treatment plan, which minimizes setup time of patient positioning and maximizes time that the charged particle beam system 100 is used for cancer treatment.

Patient Placement

Preferably, the patient 1430 is aligned in the proton beam path 269 in a precise and accurate manner. Several placement systems are described. The patient placement systems are described using the laying positioning system, but are equally applicable to the semi-vertical and sitting positioning systems.

In a first placement system, the patient is positioned in a known location relative to the platform. For example, one or more of the positioning constraints position the patient in a precise and/or accurate location on the platform. Optionally, a placement constraint element connected or replaceably connected to the platform is used to position the patient on the platform. The placement constraint element(s) is used to position any position of the patient, such as a hand, limb, head, or torso element.

In a second placement system, one or more positioning constraints, or support element, such as the platform, is aligned versus an element in the patient treatment room. Essentially a lock and key system is optionally used, where a lock fits a key. The lock and key elements combine to locate the patient relative to the proton beam path 269 in terms of any of the x-, y-, and z-position, tilt, yaw, and roll. Essentially the lock is a first registration element and the key is a second registration element fitting into, adjacent to, or with the first registration element to fix the patient location and/or a support element location relative to the proton beam path 269. Examples of a registration element include any of a mechanical element, such as a mechanical stop, and an electrical connection indicating relative position or contact.

In a third placement system, the imaging system, described supra, is used to determine where the patient is relative to the proton beam path 269 or relative to an imaging marker placed in an support element or structure holding the patient, such as in the platform. When using the imaging system, such as an X-ray imaging system, then the first placement system or positioning constraints minimize patient movement once the imaging system determines location of the subject. Similarly, when using the imaging system, such as an X-ray imaging system, then the first placement system and/or second positioning system provide a crude position of the patient relative to the proton beam path 269 and the imaging system subsequently determines a fine position of the patient relative to the proton beam path 269.

X-Ray Synchronization with Patient Respiration

In one embodiment, X-ray images are collected in synchronization with patient respiration or breathing. The synchronization enhances X-ray image clarity by removing position ambiguity due to the relative movement of body constituents during a patient breathing cycle.

In a second embodiment, an X-ray system is orientated to provide X-ray images of a patient in the same orientation as viewed by a proton therapy beam, is synchronized with patient breathing, is operable on a patient positioned for proton therapy, and does not interfere with a proton beam treatment path. Preferably, the synchronized system is used in conjunction with a negative ion beam source, synchrotron, and/or targeting method apparatus to provide an X-ray timed with patient breathing and performed immediately prior to and/or concurrently with particle beam therapy irradiation to ensure targeted and controlled delivery of energy relative to a patient position resulting in efficient, precise, and/or accurate noninvasive, in-vivo treatment of a solid cancerous tumor with minimization of damage to surrounding healthy tissue in a patient using the proton beam position verification system.

An X-ray delivery control algorithm is used to synchronize delivery of the X-rays to the patient 1430 within a given period of each breath, such as at the top or bottom of a breath when the subject is holding their breath. For clarity of combined X-ray images, the patient is preferably both accurately positioned and precisely aligned relative to the X-ray beam path 2370. The X-ray delivery control algorithm is preferably integrated with the breathing control module. Thus, the X-ray delivery control algorithm knows when the subject is breathing, where in the breath cycle the subject is, and/or when the subject is holding their breath. In this manner, the X-ray delivery control algorithm delivers X-rays at a selected period of the breathing cycle. Accuracy and precision of patient alignment allow for (1) more accurate and precise location of the tumor 1420 relative to other body constituents and (2) more accurate and precise combination of X-rays in generation of a 3-dimensional X-ray image of the patient 1430 and tumor 1420.

Patient Respiration Monitoring

Preferably, the patient's respiration pattern is monitored. When a subject or patient 1430 is breathing many portions of the body move with each breath. For example, when a subject breathes the lungs move as do relative positions of organs within the body, such as the stomach, kidneys, liver, chest muscles, skin, heart, and lungs. Generally, most or all parts of the torso move with each breath. Indeed, the inventors have recognized that in addition to motion of the torso with each breath, various motion also exists in the head and limbs with each breath. Motion is to be considered in delivery of a proton dose to the body as the protons are preferentially delivered to the tumor and not to surrounding tissue. Motion thus results in an ambiguity in where the tumor resides relative to the beam path. To partially overcome this concern, protons are preferentially delivered at the same point in each of a series of breathing cycles.

Initially a rhythmic pattern of respiration or breathing of a subject is determined. The cycle is observed or measured. For example, an X-ray beam operator or proton beam operator can observe when a subject is breathing or is between breaths and can time the delivery of the protons to a given period of each breath. Alternatively, the subject is told to inhale, exhale, and/or hold their breath and the protons are delivered during the commanded time period.

Preferably, one or more sensors are used to determine the breathing cycle of the individual. Two examples of a breath monitoring system are provided: (1) a thermal monitoring system and (2) a force monitoring system.

A first example of the thermal breath monitoring system is provided. In the thermal breath monitoring system, a sensor 2470 is placed by the nose and/or mouth of the patient. As the jaw of the patient is optionally constrained, as described supra, the thermal breath monitoring system is preferably placed by the patient's nose exhalation path. To avoid steric interference of the thermal sensor system components with proton therapy, the thermal breath monitoring system is preferably used when treating a tumor not located in the head or neck, such as a when treating a tumor in the torso or limbs. In the thermal monitoring system, a first thermal resistor 2570 is used to monitor the patient's breathing cycle and/or location in the patient's breathing cycle. Preferably, the first thermal resistor 2570 is placed by the patient's nose, such that the patient exhaling through their nose onto the first thermal resistor 2570 warms the first thermal resistor 2570 indicating an exhale. Preferably, a second thermal resistor 2560 operates as an environmental temperature sensor. The second thermal resistor 2560 is preferably placed out of the exhalation path of the patient but in the same local room environment as the first thermal resistor 2570. Generated signal, such as current from the thermal resistors 2570, is preferably converted to voltage and communicated with the main controller 110 or a sub-controller of the main controller. Preferably, the second thermal resistor is used to adjust for the environmental temperature fluctuation that is part of a signal of the first thermal resistor 2570, such as by calculating a difference between values of the thermal resistors 2560, 2570 to yield a more accurate reading of the patient's breathing cycle.

A second example of the force/pressure breath monitoring system is provided. In the force breath monitoring system, a sensor is placed by the torso. To avoid steric interference of the force sensor system components with proton therapy, the force breath monitoring system is preferably used when treating a tumor located in the head, neck, or limbs. In the force monitoring system, a belt or strap 2455 is placed around an area of the patient's torso that expands and contracts with each breath cycle of the patient. The belt 2455 is preferably tight about the patient's chest and is flexible. A force meter 2457 is attached to the belt and senses the patients breathing pattern. The forces applied to the force meter 2457 correlate with periods of the breathing cycle. The signals from the force meter 2457 are preferably communicated with the main controller 110 or a sub-controller of the main controller.

Respiration Control

Once the rhythmic pattern of the subject's respiration or breathing is determined, a signal is optionally delivered to the subject to more precisely control the breathing frequency. For example, a display screen 2490 is placed in front of the subject directing the subject when to hold their breath and when to breath. Typically, a respiration control module uses input from one or more of the breathing sensors. For example, the input is used to determine when the next breath exhale is to complete. At the bottom of the breath, the control module displays a hold breath signal to the subject, such as on a monitor, via an oral signal, digitized and automatically generated voice command, or via a visual control signal. Preferably, a display monitor 2490 is positioned in front of the subject and the display monitor displays breathing commands to the subject. Typically, the subject is directed to hold their breath for a short period of time, such as about ½, 1, 2, 3, 5, or 10 seconds. The period of time the breath is held is preferably synchronized to the delivery time of the proton beam to the tumor, which is about ½, 1, 2, or 3 seconds. While delivery of the protons at the bottom of the breath is preferred, protons are optionally delivered at any point in the breathing cycle, such as upon full inhalation. Delivery at the top of the breath or when the patient is directed to inhale deeply and hold their breath by the respiration control module is optionally performed as at the top of the breath the chest cavity is largest and for some tumors the distance between the tumor and surrounding tissue is maximized or the surrounding tissue is rarefied as a result of the increased volume. Hence, protons hitting surrounding tissue is minimized. Optionally, the display screen tells the subject when they are about to be asked to hold their breath, such as with a 3, 2, 1, second countdown so that the subject is aware of the task they are about to be asked to perform.

Proton Beam Therapy Synchronization with Respiration

A proton delivery control algorithm is used to synchronize delivery of the protons to the tumor within a given period of each breath, such as at the top or bottom of a breath when the subject is holding their breath. The proton delivery control algorithm is preferably integrated with the respiration control module. Thus, the proton delivery control algorithm knows when the subject is breathing, where in the breath cycle the subject is, and/or when the subject is holding their breath. The proton delivery control algorithm controls when protons are injected and/or inflected into the synchrotron, when an RF signal is applied to induce an oscillation, as described supra, and when a DC voltage is applied to extract protons from the synchrotron, as described supra. Typically, the proton delivery control algorithm initiates proton inflection and subsequent RF induced oscillation before the subject is directed to hold their breath or before the identified period of the breathing cycle selected for a proton delivery time. In this manner, the proton delivery control algorithm can deliver protons at a selected period of the breathing cycle by simultaneously or nearly simultaneously delivering the high DC voltage to the second pair of plates, described supra, which results in extraction of the protons from the synchrotron and subsequent delivery to the subject at the selected time point. Since the period of acceleration of protons in the synchrotron is constant or known for a desired energy level of the proton beam, the proton delivery control algorithm is used to set an AC RF signal that matches the breathing cycle or directed breathing cycle of the subject.

Developing and Implementing a Tumor Irradiation Plan

A series of steps are performed to design and execute a radiation treatment plan for treating a tumor 1420 in a patient 1430. The steps include one or more of:
  positioning and immobilizing the patient;
  recording the patient position;
  monitoring patient breathing;
  controlling patient breathing;
  collecting multi-field images of the patient to determine tumor location relative to body constituents;
  developing a radiation treatment plan;
  repositioning the patient;
  verifying tumor location; and
  irradiating the tumor.

In this section, an overview of developing the irradiation plan and subsequent implementation of the irradiation plan is initially presented, the individual steps are further described, and a more detailed example of the process is then described.

Figure 26:
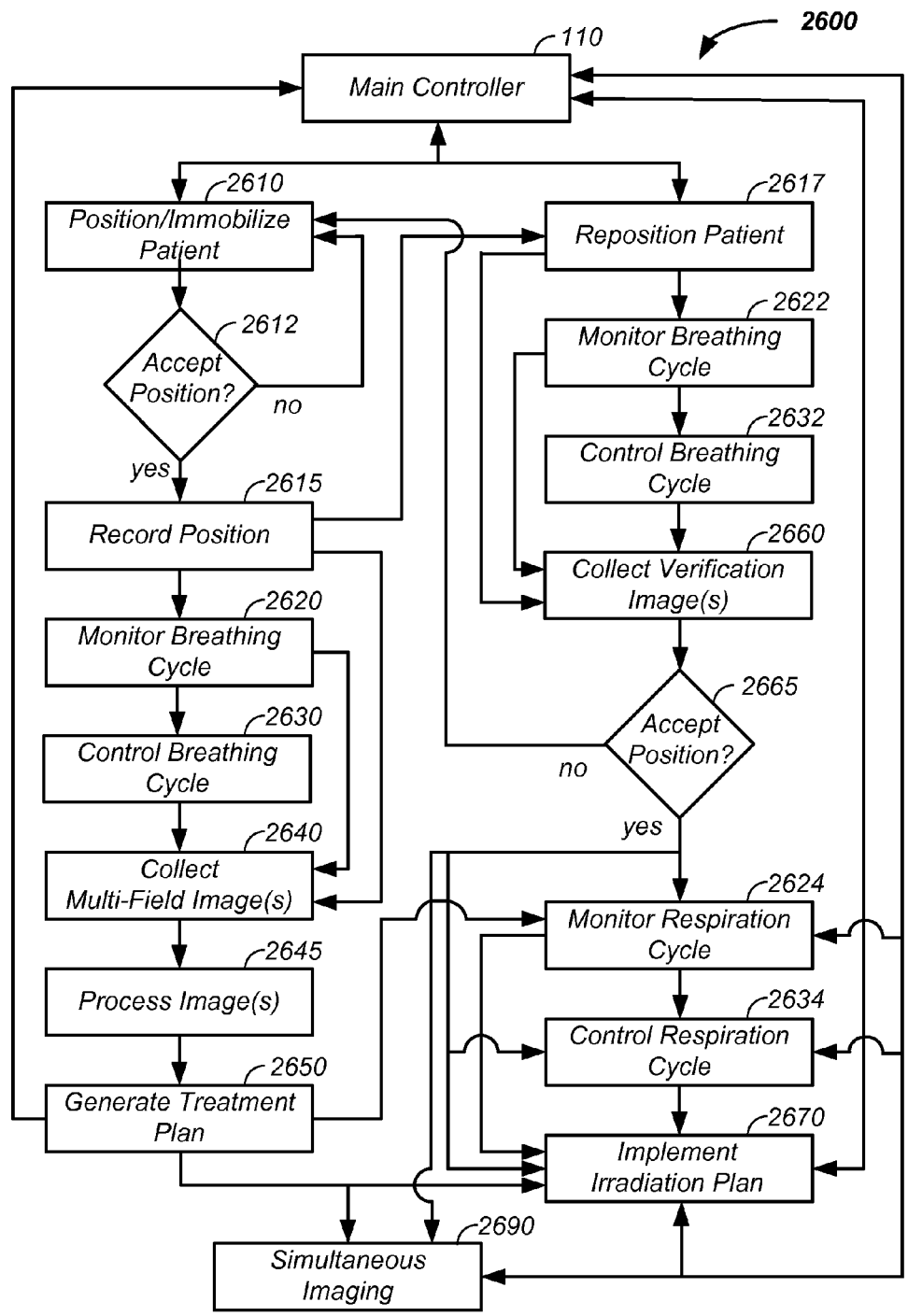
FIG. 26 illustrates a patient positioning, immobilization, and repositioning system.

Referring now to FIG. 26, an overview of a system for development of an irradiation plan and subsequent implementation of the irradiation plan 2600 is provided. Preferably, all elements of the positioning, respiration monitoring, imaging, and tumor irradiation system 2600 are under main controller 110 control.

Initially, the tumor containing volume of the patient 1430 is positioned and immobilized 2610 in a controlled and reproducible position. The process of positioning and immobilizing 2610 the patient 1430 is preferably iterated 2612 until the position is accepted. The position is preferably digitally recorded 2615 and is later used in a step of computer controlled repositioning of the patient 2617 in the minutes or seconds prior to implementation of the irradiation element 2670 of the tumor treatment plan. The process of positioning the patient in a reproducible fashion and reproducibly aligning the patient 1430 to the controlled position is further described, infra.

Subsequent to patient positioning 2610, the steps of monitoring 2620 and preferably controlling 2630 the respiration cycle of the patient 1430 are preferably performed to yield more precise positioning of the tumor 1420 relative to other body constituents, as described supra. Multi-field images of the tumor are then collected 2640 in the controlled, immobilized, and reproducible position. For example, multi-field X-ray images of the tumor 1420 are collected using the X-ray source proximate the proton beam path, as described supra. The multi-field images are optionally from three or more positions and/or are collected while the patient is rotated, as described supra.

At this point the patient 1430 is either maintained in the treatment position or is allowed to move from the controlled treatment position while an oncologist processes the multi-field images 2645 and generates a tumor treatment plan 2650 using the multi-field images. Optionally, the tumor irradiation plan is implemented 2670 at this point in time.

Typically, in a subsequent treatment center visit, the patient 1430 is repositioned 2617. Preferably, the patient's respiration cycle is again monitored 2622 and/or controlled 2632, such as via use of the thermal monitoring respiration sensors, force monitoring respiration sensor, and/or via commands sent to the display monitor 2490, described supra. Once repositioned, verification images are collected 2660, such as X-ray location verification images from 1, 2, or 3 directions. For example, verification images are collected with the patient facing the proton beam and at rotation angles of 90, 180, and 270 degrees from this position. At this point, comparing the verification images to the original multi-field images used in generating the treatment plan, the algorithm or preferably the oncologist determines if the tumor 1420 is sufficiently repositioned 2665 relative to other body parts to allow for initiation of tumor irradiation using the charged particle beam. Essentially, the step of accepting the final position of the patient 2665 is a safety feature used to verify that that the tumor 1420 in the patient 1430 has not shifted or grown beyond set specifications. At this point the charged particle beam therapy commences 2670. Preferably the patient's respiration is monitored 2624 and/or controlled 2634, as described supra, prior to commencement of the charged particle beam treatment 2670.

Optionally, simultaneous X-ray imaging 2690 of the tumor 1420 is performed during the multi-field proton beam irradiation procedure and the main controller 110 uses the X-ray images to adapt the radiation treatment plan in real-time to account for small variations in movement of the tumor 1420 within the patient 1430.

Herein the step of monitoring 2620, 2622, 2624 and controlling 2630, 2632, 2634 the patient's respiration is optional, but preferred. The steps of monitoring and controlling the patient's respiration are performed before and/or during the multi-filed imaging 2640, position verification 2660, and/or tumor irradiation 2670 steps.

The patient positioning 2610 and patient repositioning 2617 steps are further described, infra.

Coordinated Charged Particle Acceleration and Respiration Rate

In yet another embodiment, the charged particle accelerator is synchronized to the patient's respiration cycle. More particularly, synchrotron acceleration cycle usage efficiency is enhanced by adjusting the synchrotron's acceleration cycle to correlate with a patient's respiration rate. Herein, efficiency refers to the duty cycle, the percentage of acceleration cycles used to deliver charged particles to the tumor, and/or the fraction of time that charged particles are delivered to the tumor from the synchrotron. The system senses patient respiration and controls timing of negative ion beam formation, injection of charged particles into a synchrotron, acceleration of the charged particles, and/or extraction to yield delivery of the particles to the tumor at a predetermine period of the patient's respiration cycle. Preferably, one or more magnetic fields in the synchrotron 130 are stabilized through use of a feedback loop, which allows rapid changing of energy levels and/or timing of extraction from pulse to pulse. Further, the feedback loop allows control of the acceleration/extraction to correlate with a changing patient respiration rate. Independent control of charged particle energy and intensity is maintained during the timed irradiation therapy. Multi-field irradiation ensures efficient delivery of Bragg peak energy to the tumor while spreading ingress energy about the tumor.

In one example, a sensor, such as the first thermal sensor 2570 or the second thermal sensor 2560, is used to monitor a patient's respiration. A controller, such as the main controller 110, then controls charged particle formation and delivery to yield a charged particle beam delivered at a determined point or duration period of the respiration cycle, which ensures precise and accurate delivery of radiation to a tumor that moves during the respiration process. Optional charged particle therapy elements controlled by the controller include the injector 120, accelerator 132, and/or extraction 134 system. Elements optionally controlled in the injector system 120 include: injection of hydrogen gas into a negative ion source 310, generation of a high energy plasma within the negative ion source, filtering of the high energy plasma with a magnetic field, extracting a negative ion from the negative ion source, focusing the negative ion beam 319, and/or injecting a resulting positive ion beam 262 into the synchrotron 130. Elements optionally controlled in the accelerator 132 include: accelerator coils, applied magnetic fields in turning magnets, and/or applied current to correction coils in the synchrotron. Elements optionally controlled in the extraction system 134 include: radio-frequency fields in an extraction element and/or applied fields in an extraction process. By using the respiration sensor to control delivery of the charged particle beam to the tumor during a set period of the respiration cycle, the period of delivery of the charged particle to the tumor is adjustable to a varying respiration rate. Thus, if the patient breathes faster, the charged particle beam is delivered to the tumor more frequently and if the patient breathes slower, then the charged particle beam is delivered to the tumor less frequently. Optionally, the charged particle beam is delivered to the tumor with each breath of the patient regardless of the patient's changing respiration rate. This lies in stark contrast with a system where the charged particle beam delivers energy at a fixed time interval and the patient must adjust their respiration rate to match the period of the accelerator delivering energy and if the patient's respiration rate does not match the fixed period of the accelerator, then that accelerator cycle is not delivered to the tumor and the acceleration usage efficiency is reduced.

Typically, in an accelerator the current is stabilized. A problem with current stabilized accelerators is that the magnets used have memories in terms of both magnitude and amplitude of a sine wave. Hence, in a traditional system, in order to change the circulation frequency of the charged particle beam in a synchrotron, slow changes in current must be used. However, in a second example, the magnetic field controlling the circulation of the charged particles about the synchrotron is stabilized. The magnetic field is stabilized through use of: (1) magnetic field sensors sensing the magnetic field about the circulating charged particles and (2) a feedback loop through a controller or main controller 110 controlling the magnetic field about the circulating charged particles. The feedback loop is optionally used as a feedback control to the first winding coil 850 and the second winding coil 860. However, preferably the feedback loop is used to control the correction coils 852, 862, described supra. With the use of the feedback loop described herein using the magnetic field sensors, the frequency and energy level of the synchrotron are rapidly adjustable and the problem is overcome. Further, the use of the smaller correction coils 852, 862 allows for rapid adjustment of the accelerator compared to the use of the larger winding coils 850, 860, described supra. More particularly, the feedback control allows an adjustment of the accelerator energy from pulse to pulse in the synchrotron 130.

In this section, the first example yielded delivery of the charged particle beam during a particular period of the patient's respiration cycle even if the patient's respiration period is varying. In this section, the second example used a magnetic field sensor and a feedback loop to the correction coils 852, 862 to rapidly adjust the energy of the accelerator from pulse to pulse. In a third example, the respiration sensor of the first example is combined with the magnetic field sensor of the second example to control both the timing of the delivery of the charged particle beam from the accelerator and the energy of the charged particle beam from the accelerator. More particularly, the timing of the charged particle delivery is controlled using the respiration sensor, as described supra, and the energy of the charged particle beam is controlled using the magnetic filed sensors and feedback loop, as described supra. Still more particularly, a magnetic field controller, such as the main controller 110, takes the input from the respiration sensor and uses the input as: (1) a feedback control to the magnetic fields controlling the circulating charged particles energy and (2) as a feedback control to time the pulse of the charged particle accelerator to the breathing cycle of the patient. This combination allows delivery of the charged particle beam to the tumor with each breath of the patient even if the breathing rate of the patient varies. In this manner, the accelerator efficiency is increased as the cancer therapy system does not need to lose cycles when the patient's breathing is not in phase with the synchrotron charged particle generation rate.

Figure 27:
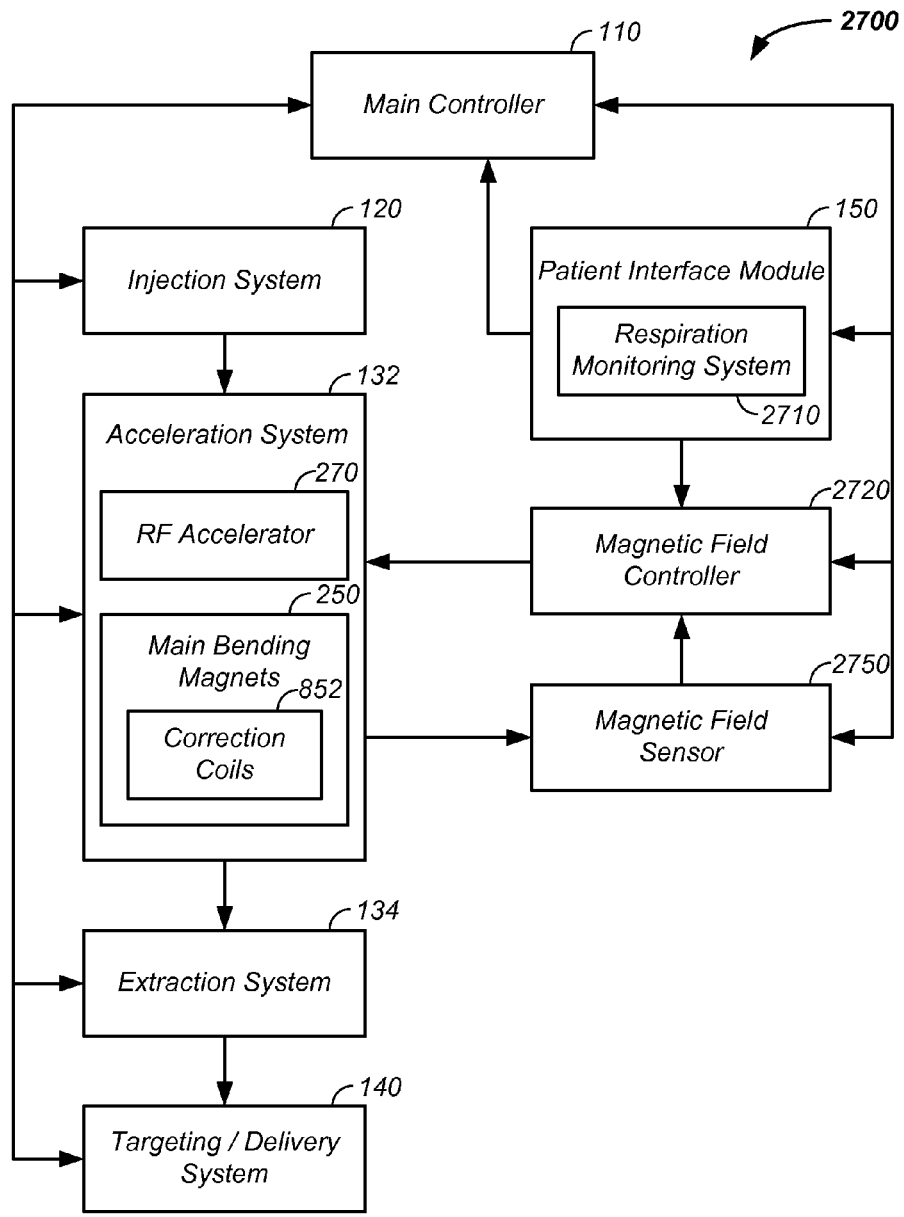
FIG. 27 shows particle field acceleration timed to a patient's respiration cycle.

Referring now to FIG. 27, the combined use of the respiration sensor and magnetic field sensor 2700 to deliver charged particles at varying energy and at varying time intervals is further described. The main controller 110 controls the injection system 120, charged particle acceleration system 132, extraction system 134, and targeting/delivery system 140. In this embodiment, a respiration monitoring system 2710 of the patient interface module 150 is used as an input to a magnetic field controller 2720. A second input to the magnetic field controller 2720 is a magnetic field sensor 2750. In one case, the respiration rates from the respiration monitoring system 2710 are fed to the main controller 130, which controls the injection system 120 and/or components of the acceleration system 132 to yield a charged particle beam at a chosen period of the respiration cycle, as described supra. In a second case, the respiration data from the respiration monitoring system is used as an input to the magnetic field controller 2720. The magnetic field controller also receives feedback input from the magnetic field sensor 2750. The magnetic field controller thus times charged particle energy delivery to correlate with sensed respiration rates and delivers energy levels of the charged particle beam that are rapidly adjustable with each pulse of the accelerator using the feedback loop through the magnetic field sensor 2750.

Figure 28:
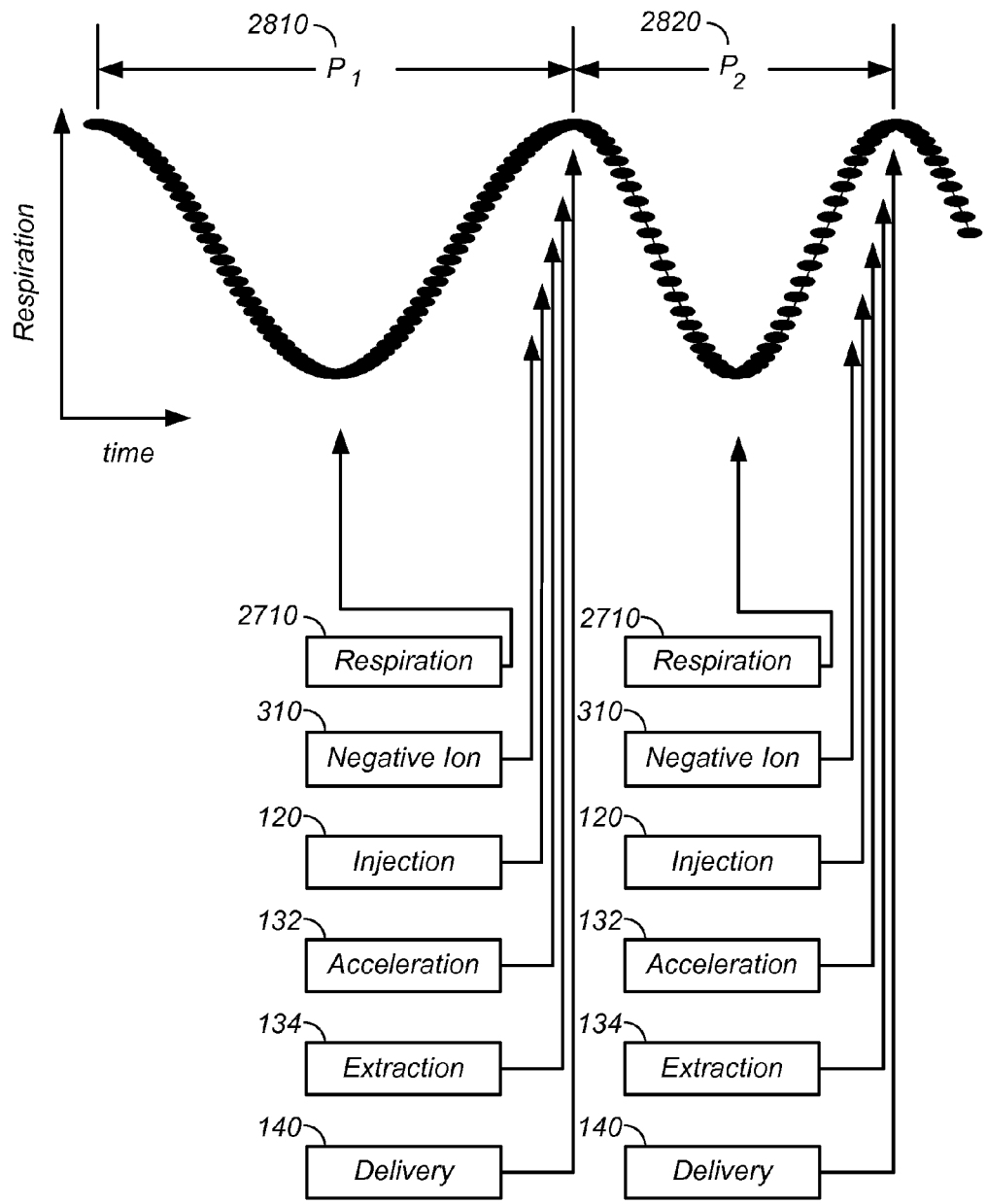
FIG. 28 illustrates adjustable particle field acceleration timing.

Referring still to FIG. 27 and now additionally referring to FIG. 28, a further example is used to clarify the magnetic field control using a feedback loop 2700 to change delivery times and/or periods of proton pulse delivery. In one case, a respiratory sensor 2710 senses the respiration cycle of the patient. The respiratory sensor sends the patient's breathing pattern or information to an algorithm in the magnetic field controller 2720, typically via the patient interface module 150 and/or via the main controller 110 or a subcomponent thereof. The algorithm predicts and/or measures when the patient is at a particular point in the breathing cycle, such as at the top or bottom of a breath. One or more magnetic field sensors 2750 are used as inputs to the magnetic field controller 2720, which controls a magnet power supply for a given magnetic, such as within a first turning magnet 420 of a synchrotron 130. The control feedback loop is thus used to dial the synchrotron to a selected energy level and to deliver protons with the desired energy at a selected point in time, such as at a particular point in the respiration cycle. The selected point in the respiration cycle is optionally anywhere in the respiration cycle and/or for any duration during the respiration cycle. As illustrated in FIG. 28, the selected time period is at the top of a breath for a period of about 0.1, 0.5, 1 seconds. More particularly, the main controller 110 controls injection of hydrogen into the injection system, formation of the negative ion 310, controls extraction of negative ions from negative ion source 310, controls injection 120 of protons into the synchrotron 130, and/or controls acceleration of the protons in a manner that combined with extraction 134 delivers the protons 140 to the tumor at a selected point in the respiration cycle. Intensity of the proton beam is also selectable and controllable by the main controller 130 at this stage, as described supra. The feedback control from the magnetic field controller 2720 is optionally to a power or power supplies for one or both of the main bending magnet 250, described supra, or to the correction coils 852, 862 within the main bending magnet 250. Having smaller applied currents, the correction coils 852, 862 are rapidly adjustable to a newly selected acceleration frequency or corresponding charged particle energy level. Particularly, the magnetic field controller 2720 alters the applied fields to the main bending magnets or correction coils that are tied to the patient's respiration cycle. This system is in stark contrast to a system where the current is stabilized and the synchrotron delivers pulses with a fixed period. Preferably, the feedback of the magnetic field design coupled with the correction coils allows for the extraction cycle to match the varying respiratory rate of the patient, such as where a first respiration period 2810, $P_1$, does not equal a second respiration period 2820, $P_2$.

Computer Controlled Patient Repositioning

One or more of the patient positioning unit components and/or one of more of the patient positioning constraints are preferably under computer control. For example, the computer records or controls the position of the patient positioning elements 2415, such as via recording a series of motor positions connected to drives that move the patient positioning elements 2415. For example, the patient is initially positioned 2610 and constrained by the patient positioning constraints 2415. The position of each of the patient positioning constraints is recorded and saved by the main controller 110, by a sub-controller of the main controller 110, or by a separate computer controller. Then, imaging systems are used to locate the tumor 1420 in the patient 1430 while the patient is in the controlled position of final treatment. Preferably, when the patient is in the controlled position, multi-field imaging is performed, as described herein. The imaging system 170 includes one or more of: MRI's, X-rays, CT's, proton beam tomography, and the like. Time optionally passes at this point while images from the imaging system 170 are analyzed and a proton therapy treatment plan is devised. The patient optionally exits the constraint system during this time period, which may be minutes, hours, or days. Upon, and preferably after, return of the patient and initial patient placement into the patient positioning unit, the computer returns the patient positioning constraints to the recorded positions. This system allows for rapid repositioning of the patient to the position used during imaging and development of the multi-field charged particle irradiation treatment plan, which minimizes setup time of patient positioning and maximizes time that the charged particle beam system 100 is used for cancer treatment.

Reproducing Patient Positioning and Immobilization

In one embodiment, using a patient positioning and immobilization system 2400, a region of the patient 1430 about the tumor 1420 is reproducibly positioned and immobilized, such as with the motorized patient translation and rotation positioning system and/or with the patient positioning constraints 1415. For example, one of the above described positioning systems 2400, such as (1) the semi-vertical partial immobilization system; (2) the sitting partial immobilization system; or (3) the laying position system is used in combination with the patient translation and rotation system to position the tumor 1420 of the patient 1430 relative to the proton beam path 268. Preferably, the position and immobilization system 2400 controls position of the tumor 1420 relative to the proton beam path 268, immobilizes position of the tumor 1420, and facilitates repositioning the tumor 1420 relative to the proton beam path 268 after the patient 1430 has moved away from the proton beam path 268, such as during development of the irradiation treatment plan 2650.

Preferably, the tumor 1420 of the patient 1430 is positioned in terms of 3-D location and in terms of orientation attitude. Herein, 3-D location is defined in terms of the x-, y-, and z-axes and orientation attitude is the state of pitch, yaw, and roll. Roll is rotation of a plane about the z-axis, pitch is rotation of a plane about the x-axis, and yaw is the rotation of a plane about the y-axis. Tilt is used to describe both roll and pitch. Preferably, the positioning and immobilization system 2400 controls the tumor 1420 location relative to the proton beam path 268 in terms of at least three of and preferably in terms of four, five, or six of: pitch, yaw, roll, x-axis location, y-axis location, and z-axis location.

Chair

The patient positioning and immobilization system 2400 is further described using a chair positioning example. For clarity, a case of positioning and immobilizing a tumor in a shoulder is described using chair positioning. Using the semi-vertical immobilization system, the patient is generally positioned using the seat support 2420, knee support 2460, and/or foot support 2470. To further position the shoulder, a motor in the back support 2430 pushes against the torso of the patient. Additional arm support 2450 motors align the arm, such as by pushing with a first force in one direction against the elbow of the patient and the wrist of the patient is positioned using a second force in a counter direction. This restricts movement of the arm, which helps to position the shoulder. Optionally, the head support is positioned to further restrict movement of the shoulder by applying tension to the neck. Combined, the patient positioning constraints 2415 control position of the tumor 1420 of the patient 1430 in at least three dimensions and preferably control position of the tumor 1420 in terms of all of yaw, roll, and pitch movement as well as in terms of x-, y-, and z-axis position. For instance, the patient positioning constraints position the tumor 1420 and restricts movement of the tumor, such as by preventing patient slumping. Optionally, sensors in one or more of the patient positioning constraints 2415 record an applied force. In one case, the seat support senses weight and applies a force to support a fraction of the patient's weight, such as about 50, 60, 70, or 80 percent of the patient's weight. In a second case, a force applied to the neck, arm, and/or leg is recorded.

Generally, the patient positioning and immobilization system 2400 removes movement degrees of freedom from the patient 1430 to accurately and precisely position and control the position of the tumor 1420 relative to the X-ray beam path 2370, proton beam path 268, and/or an imaging beam path. Further, once the degrees of freedom are removed, the motor positions for each of the patient positioning constraints are recorded and communicated digitally to the main controller 110. Once the patient moves from the immobilization system 2400, such as when the irradiation treatment plan is generated 2650, the patient 1430 must be accurately repositioned before the irradiation plan is implemented. To accomplish this, the patient 1430 sits generally in the positioning device, such as the chair, and the main controller sends the motor position signals and optionally the applied forces back to motors controlling each of the patient positioning constraints 2415 and each of the patient positioning constraints 2415 are automatically moved back to their respective recorded positions. Hence, re-positioning and re-immobilizing the patient 1430 is accomplished from a time of sitting to fully controlled position in less than about 10, 30, 60, or 120 seconds.

Using the computer controlled and automated patient positioning system, the patient is re-positioned in the positioning and immobilization system 2400 using the recalled patient positioning constraint 2415 motor positions; the patient 1430 is translated and rotated using the patient translation and rotation system relative to the proton beam 268; and the proton beam 268 is scanned to its momentary beam position 269 by the main controller 110, which follows the generated irradiation treatment plan 2650.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:
1. A method for irradiating a tumor of a patient with charged particles, comprising the steps of:
  delivering the charged particles with a charged particle therapy system, comprising:
    a synchrotron;
    an extraction foil;
    a charged particle beam path; and
    a rotatable platform, wherein said charged particle beam path runs through said synchrotron and above said rotatable platform;
  controlling intensity of the charged particles using a current originating at said extraction foil, said extraction foil positioned in the charged particle beam path after entry into said synchrotron and prior to a Lambertson extraction magnet, wherein electrons of said current originate in atoms of said extraction foil;
  actively scanning the charged particles along at least three axes, wherein said at least three axes comprise: a horizontal axis, a vertical axis, and an applied energy axis;
  during an irradiation period, rotating said rotatable platform to at least five irradiation positions covering at least ninety degrees of rotation of said rotatable platform;
  timing delivery of the charged to the tumor using a respiration signal, wherein a respiration command is sent to the patient using a display monitor, said display monitor configured to co-rotate with said rotatable platform, said respiration signal monitor respiration of the patient; and
  irradiating the tumor with the charged particles during each of said at least five irradiation positions.

2. The method of claim 1, further comprising the steps of:
  holding the patient with said rotatable platform during said irradiation period; and
  delivering the charged particles through said charged particle beam path, wherein said charged particle beam path circumferentially surrounds the charged particles at least in said synchrotron.

3. The method of claim 1, further comprising the step of:
  rotating said rotatable platform through about three hundred sixty degrees during said irradiation period.

4. The method of claim 3, said charged particle therapy system further comprising an irradiation control module, wherein the tumor comprises a distal region, wherein said irradiation control module further comprises the step of:
  terminating said charged particle beam path in said distal region of the tumor, using control of energy of the charged particles, in each of said at least five irradiation positions.

5. The method of claim 4, further comprising the step of:
  said irradiation control module controlling both rotation of said rotatable platform and said energy of the charged particles to irradiate, with Bragg peak energy of the charged particles, a changing distal position of the tumor as a function of position of said rotatable platform.

6. The method of claim 1, said charged particle therapy system further comprising the step of:
  distributing delivered distal energy of the charged particles about an outer perimeter of the tumor, wherein ingress energy of the charged particles comprises three hundred sixty degrees of circumferential distribution about a plane of the tumor.

7. The method of claim 1, further comprising the steps of:
  controlling energy of the charged particles during an extraction phase of the charged particles from said synchrotron using said extraction foil; and
  controlling said intensity of the charged particles during said extraction phase of the charged particles from said synchrotron using the electrons originating in the atoms of the extraction foil.

8. The method of claim 1, wherein said step of rotating said rotatable platform comprises rotation of said rotatable platform through about three hundred sixty degrees during said irradiation period, and wherein said step of irradiating the tumor occurs with the charged particles in at least thirty rotation positions of said rotatable platform during said irradiation period.

9. The method of claim 1, wherein said step of actively scanning occurs at each of said of said at least five irradiation positions.

10. The method of claim 9, wherein said active scanning system further comprises the step of:
controlling said intensity of the charged particles.

11. The method of claim 1, further comprising the steps of:
focusing ions using electric field lines terminating at metal conducting paths within the charged particle beam path, said metal conducting paths comprising a conductive mesh; and
injecting the ions as the charged particles into said synchrotron.

12. The method of claim 1, further comprising the step of:
turning the charged particles in said synchrotron about ninety degrees using a set of four turning magnets, said set of turning magnets wound by a coil, wherein said coil does not occupy space directly between any of said four magnets.

13. The method of claim 1, further comprising the step of:
accelerating the charged particles in an accelerator system in said synchrotron, said accelerator system comprising:
a set of at least ten coils;
a set of at least ten wire loops;
a set of at least ten microcircuits, each of said microcircuits integrated to one of said loops, wherein each of said loops completes at least one turn about at least one of said coils; and
timing said accelerator system with a radio-frequency synthesizer sending a low voltage signal to each of said microcircuits, each of said microcircuits amplifying said low voltage signal yielding an acceleration voltage.

14. The method of claim 1, further comprising the step of:
applying a radio-frequency field to the charged particles in said synchrotron to yield oscillating charged particles, wherein the current is used in control of the radio-frequency field;
extracting the oscillating charged particles from said synchrotron by slowing the oscillating charged particles with said extraction foil.

15. The method of claim 1, further comprising the step of:
monitoring both a horizontal position of the charged particles and a vertical position of the charged particles in a beam transport path using photons emitted from a coating on an output foil, said photons emitted from said coating when struck by the charged particles.

16. The method of claim 1, further comprising the steps of:
generating an image of the tumor using an X-ray system; and
said charged particle therapy system targeting the tumor using said image, wherein said X-ray system comprises a cathode comprising a first diameter and an electron beam path comprising a second diameter, said first diameter at least twice said second diameter, wherein electrons emitted at said cathode traverse said electron beam path before striking an X-ray generation source.

17. The method of claim 1, further comprising the steps of;
monitoring respiration of the patient using a respiration sensor; and
controlling said respiration, said step of controlling using a signal generated by said respiration sensor and feedback respiration instructions provided to the patient provided on a monitor.

18. The method of claim 1, further comprising the step of;
dynamically adjusting timing of said step of delivering the charged particles to occur in synchronization with a changing respiration rate of the patient.

19. A method for irradiating a tumor of a patient with charged particles, comprising the steps of:
delivering the charged particles with a charged particle therapy system, comprising:
a synchrotron;
an extraction foil;
a charged particle beam path: and
a rotatable platform, wherein said charged particle beam path runs through said synchrotron and above said rotatable platform;
maintaining a first vacuum in an on beam focusing system in the charged particle beam path prior to said synchrotron;
maintaining a second vacuum in said synchrotron, said first vacuum in said ion beam focusing system and said second vacuum in said synchrotron separated by a converting foil, said converting foil converting negative ions into positive ions, pressure of said first vacuum not equal to pressure of said second vacuum;
controlling intensity of the charged particles using a current originating at said extraction foil, said extraction foil positioned in the charged particle beam path after entry into said synchrotron and prior to a Lambertson extraction magnet, wherein electrons of said current originate in atoms of said extraction foil;
during an irradiation period, rotating said rotatable platform to at least five irradiation positions covering at least ninety degrees of rotation of said rotatable platform; and
irradiating the tumor with the charged particles during each of said at least five irradiation positions.

* * * * *